US009192601B2

(12) United States Patent
Evans et al.

(10) Patent No.: US 9,192,601 B2
(45) Date of Patent: Nov. 24, 2015

(54) METHODS FOR ENHANCING MUSCLE PERFORMANCE AND TONE

(75) Inventors: Ronald M. Evans, La Jolla, CA (US); Vihang A. Narkar, San Diego, CA (US); Reuben J. Shaw, San Diego, CA (US); Michael Downes, San Diego, CA (US); Ruth T. Yu, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 906 days.

(21) Appl. No.: 12/810,123

(22) PCT Filed: Dec. 29, 2008

(86) PCT No.: PCT/US2008/088466
§ 371 (c)(1),
(2), (4) Date: Dec. 14, 2010

(87) PCT Pub. No.: WO2009/086526
PCT Pub. Date: Jul. 9, 2009

(65) Prior Publication Data
US 2011/0112047 A1    May 12, 2011

Related U.S. Application Data

(63) Continuation-in-part of application No. 11/966,851, filed on Dec. 28, 2007, now abandoned, and a continuation-in-part of application No. PCT/US2007/089124, filed on Dec. 28, 2007.

(60) Provisional application No. 60/882,774, filed on Dec. 29, 2006.

(51) Int. Cl.
*A61K 31/4178* (2006.01)
*A61K 31/426* (2006.01)
*A61K 31/47* (2006.01)
*C12Q 1/68* (2006.01)

(52) U.S. Cl.
CPC ........... *A61K 31/426* (2013.01); *A61K 31/4178* (2013.01); *A61K 31/47* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 5,010,175 A | 4/1991 | Rutter et al. | 530/334 |
| 5,082,829 A | 1/1992 | Gruber et al. | 514/43 |
| 5,288,514 A | 2/1994 | Ellman | 435/4 |
| 5,506,337 A | 4/1996 | Summerton et al. | 506/15 |
| 5,519,134 A | 5/1996 | Acevedo et al. | 544/243 |
| 5,525,735 A | 6/1996 | Gallop et al. | 548/533 |
| 5,539,083 A | 7/1996 | Cook et al. | 530/333 |
| 5,549,974 A | 8/1996 | Holmes | 428/403 |
| 5,569,588 A | 10/1996 | Ashby et al. | 435/6 |
| 5,593,853 A | 1/1997 | Chen et al. | 435/29 |
| 5,719,060 A | 2/1998 | Hutchens et al. | 436/174 |
| 5,776,672 A | 7/1998 | Hashimoto et al. | 435/6 |
| 5,777,100 A | 7/1998 | Bullough et al. | 536/26.9 |
| 5,861,274 A | 1/1999 | Evans et al. | 435/69.1 |
| 5,972,602 A | 10/1999 | Hyland et al. | 435/6 |
| 5,972,692 A | 10/1999 | Hashimoto et al. | 435/285.2 |
| 6,090,556 A | 7/2000 | Kato | 435/6 |
| 6,203,988 B1 | 3/2001 | Kambara et al. | 435/6 |
| 6,806,049 B1 | 10/2004 | Maekawa et al. | 435/6 |
| 6,811,977 B2 | 11/2004 | Wold et al. | 435/6 |
| 6,816,790 B2 | 11/2004 | Grinstein et al. | 702/23 |
| 6,881,586 B2 | 4/2005 | Hutchens et al. | 506/5 |
| 6,893,824 B2 | 5/2005 | Ito | 435/6 |
| 6,897,072 B1 | 5/2005 | Rich et al. | 436/173 |
| 6,911,307 B1 | 6/2005 | Dautel et al. | 435/6 |
| 7,031,847 B1 | 4/2006 | Nozaki et al. | 702/20 |
| 2004/0259948 A1 | 12/2004 | Tontonoz et al. | 514/560 |
| 2005/0233328 A1 | 10/2005 | Berghs et al. | 435/6 |
| 2006/0154335 A1 | 7/2006 | Evans et al. | 435/69.1 |
| 2006/0287356 A1 | 12/2006 | Iyengar et al. | 514/301 |
| 2007/0015686 A1 | 1/2007 | Heuer et al. | 514/2 |
| 2007/0054965 A1* | 3/2007 | Murase et al. | |
| 2007/0203083 A1 | 8/2007 | Mootha et al. | 514/44 R |
| 2007/0248698 A1 | 10/2007 | Kwak et al. | 424/746 |
| 2007/0265223 A1 | 11/2007 | Tomaselli et al. | 514/46 |
| 2008/0187928 A1 | 8/2008 | Evans et al. | 435/6 |

FOREIGN PATENT DOCUMENTS

| | | |
|---|---|---|
| WO | WO 91/19735 | 12/1991 |
| WO | WO 92/00091 | 1/1992 |
| WO | WO 93/20242 | 10/1993 |
| WO | WO 97/00271 | 1/1997 |
| WO | WO 97/27847 | 8/1997 |
| WO | WO 97/27857 | 8/1997 |

(Continued)

OTHER PUBLICATIONS

Medical News Today, medicalnewstoday.com, "Mechanism discovered for muscle wasting seen in diabetes, AIDS and other diseases", Oct. 15, 2004, pp. 1-3 of 3.*
International Preliminary Report on Patentability for PCT/US2008/088466, mailed Jul. 8, 2010.
Achten et al. (2004), Nutrition, 20:716-727.
Adams (2002), Journal of Applied Physiology, 93:1159-1167.
Altschul et. al. (1990), Journal of Molecular Biology, 215:403-410.
Baldwin et al. (2002), Am. J. Phys. Med. Rehabil., 81:S40-S51.
Baldwin et al. (2001), Journal of Applied Physiology, 90:345-357.
Barish et al. (2006), The Journal of Clinical Investigation, 116:590-597.
Bassel-Duby et al. (2006), Annu. Rev. Biochem., 75:19-37.
Baum, (1993), C&EN, 71:33-34.

(Continued)

*Primary Examiner* — Savitha Rao
*Assistant Examiner* — Gregg Polansky
(74) *Attorney, Agent, or Firm* — Kilpatrick Townsend & Stockton LLP

(57) ABSTRACT

Provided herein are methods and compositions for improving muscle performance and increasing endurance. Agonists of AMP-activated protein kinase (AMPK) and agonists of peroxisome proliferator-activated receptor delta (PPARδ) can be used in such treatments.

14 Claims, 15 Drawing Sheets

(56) References Cited

FOREIGN PATENT DOCUMENTS

| | | |
|---|---|---|
| WO | WO 97/28115 | 8/1997 |
| WO | WO 97/28137 | 8/1997 |
| WO | WO 97/28149 | 8/1997 |
| WO | WO 98/27974 | 7/1998 |
| WO | WO 01/00603 | 1/2001 |
| WO | WO 01/93874 | 12/2001 |
| WO | WO 02/09726 A1 * | 2/2002 |
| WO | WO 02/092590 | 11/2002 |
| WO | WO 2005/105754 | 11/2005 |
| WO | WO 2005/113506 | 12/2005 |
| WO | WO 2006/018174 | 2/2006 |
| WO | WO 2006/032023 | 3/2006 |
| WO | WO 2006/033709 | 3/2006 |
| WO | WO 2006/041197 | 4/2006 |
| WO | WO 2008/016278 | 2/2008 |
| WO | WO 2008/083330 | 7/2008 |
| WO | WO 2009/086526 | 7/2009 |

OTHER PUBLICATIONS

Berg et al. (2002), Proc. Natl. Acad. Sci. USA, 99:3830-3835.
Boger et al. (1998), Bioorg. Med. Chem. Lett., 8:2339-2344.
Booth et al. (1991), Physiological Reviews, 71:541-585.
Bronner et al. (2004), Biochemical Journal, 384:295-305.
Buchwald et al. (1980), Surgery 88:507-516.
Campbell et al. (1994), J. Org. Chem., 59:658-660.
Centrella et al. (2004), Gene, 342:13-24.
Chawla et al. (2003), Proc. Natl. Acad. Sci., USA, 100:1268-1273.
Chen et al. (1994), J. Am. Chem. Soc., 116:2661-2662.
Chen et al. (2003), Diabetes, 52:2205-2212.
Cho et al. (1993), Science, 261:1303-1305.
Civitarese et al. (2006), Cell Metabolism, 4:75-87.
Committee on Sports Medicine and Fitness (2005), Reginald L. Washington, MD, Chairperson, Pediatrics, 115:1103-1106.
Cool et al. (2006), Cell Metabolism, 3:403-416.
Corpet et al. (1988), Nucleic Acids Research, 16:10881-10890.
Corton et al. (1995), European Journal of Biochemistry, 229:558-565.
Despres et al. (1984), Metabolism, 33:235-239.
DeWitt et al. (1993), Proc. Natl. Acad. Sci. USA, 90:6909-6913.
Dittrich et al. (1998), Bioorganic & Medicinal Chemistry Letters, 8:2351-2356.
Doriguzzi et al. (1983), Histochemistry, 79:289-294.
During et al. (1989), Ann. Neurol. 25:351-356.
Fitzsimons et al. (1981), Biochemical Journal, 193:229-233.
Fluck et al. (2003), Rev. Physiol. Biochem. Pharmacol., 146:159-216.
Freyssenet at al. (1996), Archives of Physiology and Biochemistry, 104:129-141.
Furka et al. (1991), Int. J. Peptide Protein Res., 37:487-493.
Garnier et al. (2005), The FASEB Journal, 19:43-52.
Gauthier et al. (1979), The Journal of Cell Biology, 81:10-25.
Gebeyehu et al. (1987), Nucleic Acids Research, 15:4513-4534.
Geysen, et al. (1984), Proc Natl. Acad. Sci., 81:3998-4002.
Gloffke (2002), The Scientist, 16:52.
Goodyear et al. (1996), Am. J. Physiol., 271:E403-E408.
Hagihara et al. (1992), J. Am. Chem. Soc., 114:6568-6570.
Higgins et al. (1988), Gene 73:237-244.
Higgins et al. (1989), Computer Applications in the Biosciences, 5:151-153.
Hirschmann et al. (1992), J. Am. Chem. Soc., 114:9217-9218.
Hittel et al. (2005), Journal of Applied Physiology, 98:168-179.
Holloszy et al. (1984), J. Appl. Physiol., 56:831-838.
Holloszy (1975), Medicine and Science in Sports, 7:155-164.
Houghten (1985), Proc Natl. Acad. Sci. USA, 82:5131-5135.
Houghton et al. (1991), Nature, 354:84-86.
Howard et al. (1989), J. Neurosurg., 71,105-112.
Hsiao et al. (2004), Bioinformatics, 20:3108-3127.
Huang, et al. (1992), Computer Applications in the Biosciences, 8:155-165.
Ikeda et al. (2002), Biochemical and Biophysical Research Communications, 296:395-400.
Jepsen et al. (2002), Journal of Cell Science, 115:689-698.
Jones et al. (2000), Sports Medicine, 29:373-386.
Kiens (2006), Physiological Reviews, 86:205-243.
Kliewer et al. (1994), Proc. Natl. Acad. Sci U SA, 91:7355-7359.
Koves et al. (2005), The Journal of Biological Chemistry, 280:33588-33598.
Krämer et al. (2005), Diabetes, 54:1157-1163.
Krämer et al. (2007), The Journal of Biological Chemistry, 282:19313-19320.
Lagouge et al. (2006), Cell, 127:1109-1122.
Lam et al. (1997), Chem. Rev., 97:411-448.
Landegren et al. (1988), Science 242:229-237.
Langer et al. (1981), Proc. Natl. Acad. Sci. USA, 78:6633-6637.
Langer et al. (1983), Rev. Macromol. Chem. Phys., C23:61-126.
Langer (1990), Science, 249:1527-1533.
Larsson et al. (1985), Muscle and Nerve, 8:714-722.
Leff (2003), Biochemical Society, 31:224-227.
Leibowitz et al. (2000), FEBS Letters, 473:333-336.
Levy et al. (1985), Science 228:190-192.
Liang et al. (1996), Science, 274:1520-1522.
Lundby et al. (2006), Eur. J. Appl. Physiol., 96:363-369.
Mader et al. (2001), Int. J. Sports Med., 22:344-349.
Mahoney et al. (2005) Physical Medicine and Rehabilitation Clinics of North America, 16:859-873.
Mahoney et al. (2005), The FASEB Journal, 19:1498-1500.
Man et al. (2008), Journal of Investigative Dermatology, 128:370-377.
Mauriege et al. (1997), Am. J. Physiol., 273:E497-E506.
Minnaard et al. (2005), Muscle Nerve, 31: 339-348.
Musi et al. (2002), Current Drug Targets—Immure, Endocrine and Metabolic Disorders, 2:119-127.
Nagase et al. (1996), Journal of Clinical Investigation, 97:2898-2904.
Narkar et al. (2008), Cell, 134:405-415.
Needleman et al. (1970), J. Mol. Biol., 48:443.
Ogilvie et al. (1990), Stain Technology, 65:231-241.
Ordentlich et al. (2001), Curr. Top. Microbiol. Immunol., 254:101-116.
Parry (2001), Exerc. Sport Sci. Rev., 29:175-179.
Pearson et al., (1988), Proc. Natl. Acad. Sci. USA, 85:2444-2448.
Pearson (1994), Methods in Molecular Biology, 24:307-331.
Pette et al. (2000), Microscopy Research and Technique, 50:500-509.
Privalsky (2004), Annu. Rev. Physiol, 66:315-360.
Ramakrishnan et al. (2005), The Journal of Biological Chemistry, 280:8651-8659.
Rando et al. (1994), The Journal of Cell Biology, 125:1275-1287.
Reznick et al. (2006), The Journal of Physiology, 574:33-39.
Saudek et al. (1989), The New England Journal of Medicine, 321:574-579.
Schmitt et al. (2003), Physiol. Genomics, 15:148-157.
Schrauwen-Hinderling et al. (2003), The Journal of Clinical Endocrinology & Metabolism, 88:1610-1616.
Scott et al. (1990), Science, 249:386-390.
Screaton et al. (2004), Cell, 119:61-74.
Sefton (1987), Critical Reviews in Biomedical Engineering, 14:201-240.
Short et al. (2005), Journal of Applied Physiology, 99:95-102.
Simoneau et al. (1995), The FASEB Journal, 9:1091-1095.
Singleton et al. (2001), Neurobiology of Disease, 8:541-554.
Siu et al. (2004), Journal of Applied Physiology, 97:277-285.
Smith et al. (1981), Advances in Applied Mathematics, 2:482-489.
Smith (2002), Biochemical Society Transactions, 30:1086-1090.
Songyang et al. (1993), Cell, 72:767-778.
Sprecher et al. (2007), Arteriosclerosis, Thrombosis, and Vascular Biology, 27:359-365.
Tatusova et al. (1999), FEMS Microbiology Letters, 174:247-250.
Timmons et al. (2005), The FASEB Journal, 19:750-760.
Treat et al. (1989), Liposomes in the Therapy of Infectious Disease and Cancer, pp. 353-365.
Vaughan (1996), Nature Biotechnology, 14:309-314.

(56) References Cited

OTHER PUBLICATIONS

Wang et al. (2003), Cell, 113:159-170.
Wang et al. (2004), PLoS. Biology, 2(e294):1532-1539.
Wolcott (1992), Clinical Microbiology Reviews, 5:370-386.
Yamauchi et al. (2006), Nature Medicine, 8:1288-1295.
Yoshioka et al. (2003), The FASEB Journal, 17:1812-1819.
European Search Report for EP 08 86 6040 mailed Feb. 7, 2011.

* cited by examiner

FIG. 1A
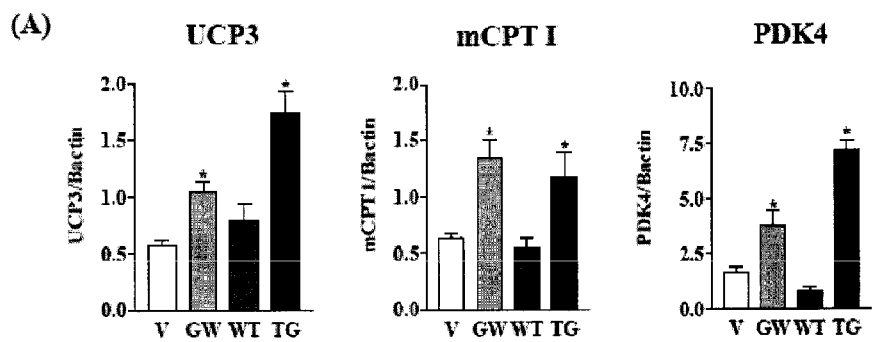
FIG. 1B  FIG. 1C  FIG. 1D
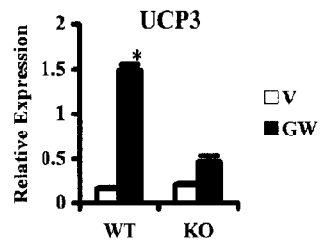 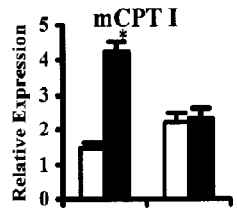 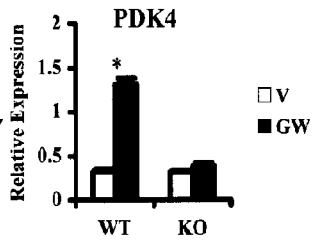
FIG. 1E
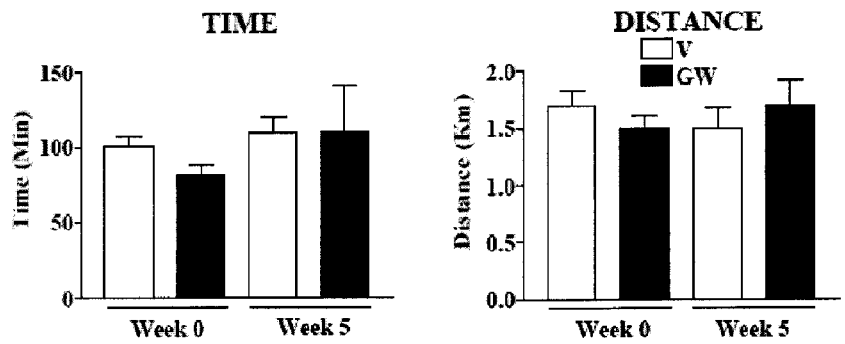
FIG. 1A-E

FIG. 2A-C

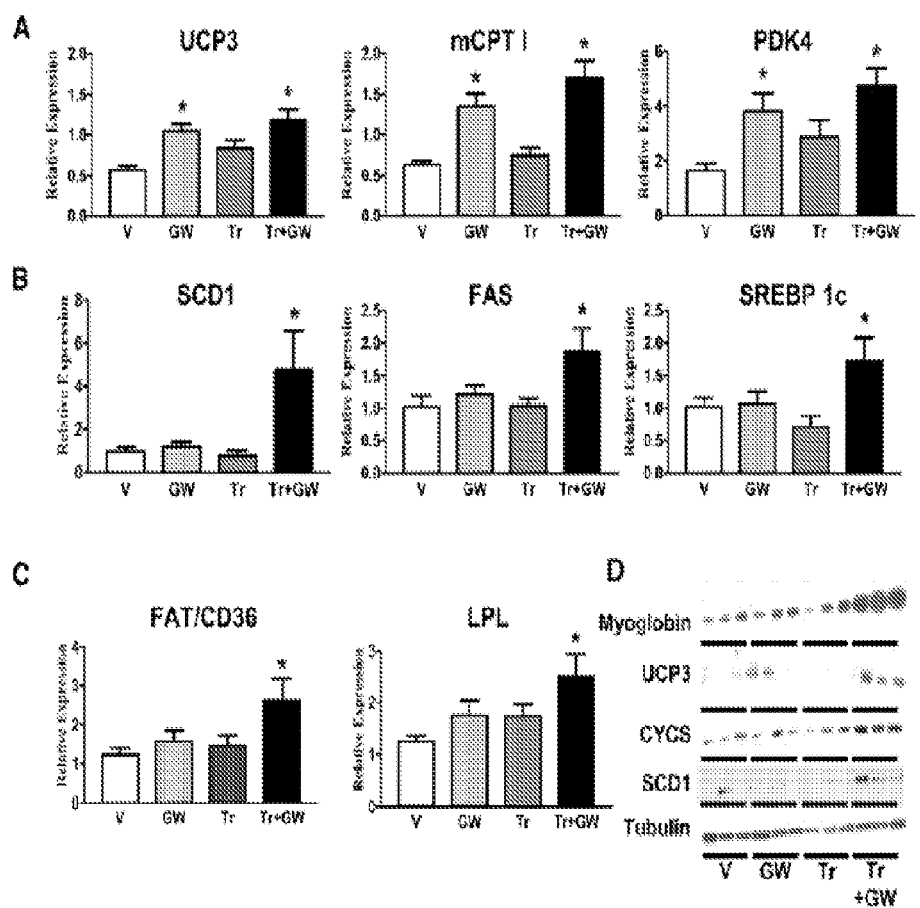
FIG. 3A-D

Fig. 6
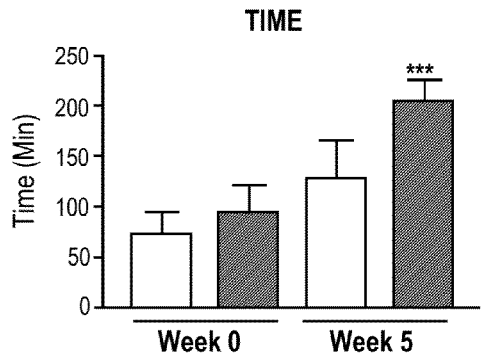
FIG. 6A
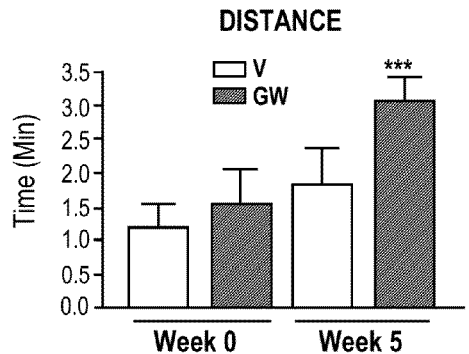
FIG. 6B
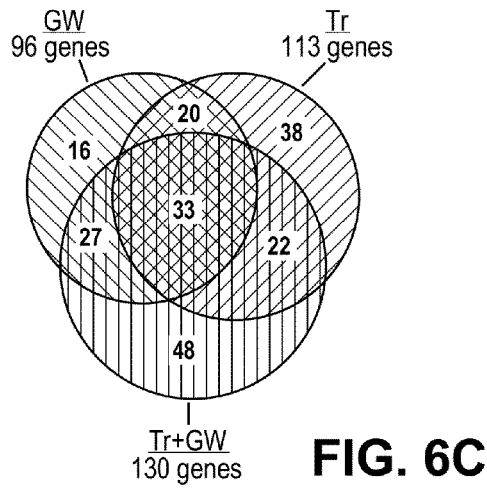
FIG. 6C
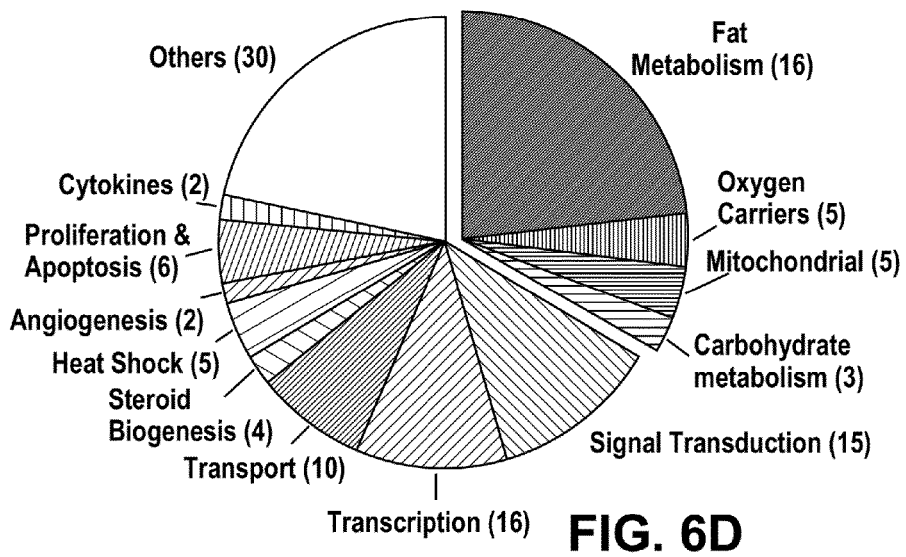
FIG. 6D

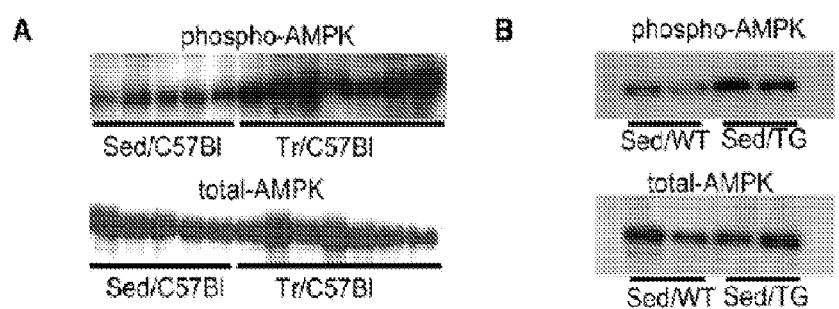
FIG. 7A-B

FIG. 8A-C

FIGS. 9A-H
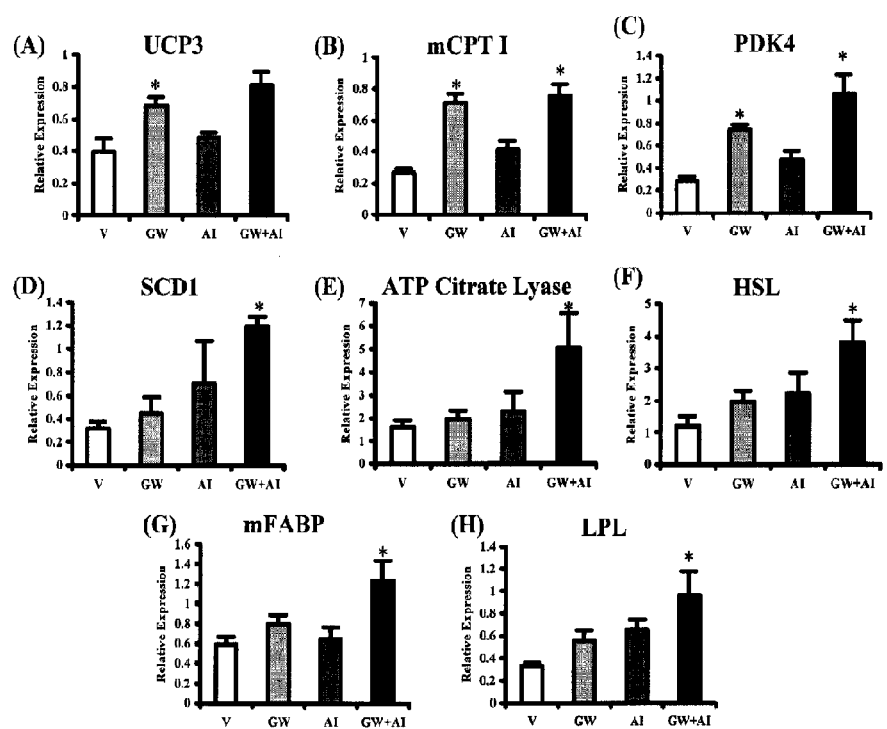

METHODS FOR ENHANCING MUSCLE PERFORMANCE AND TONE

CROSS-REFERENCE TO RELATED APPLICATIONS

This application is a national stage application, filed under 35 U.S.C. §371, of International Application No. PCT/US2008/088466, filed Dec. 29, 2008, which claims the benefit of U.S. Provisional Application No. 61/080,841, filed Jul. 15, 2008 and is a continuation-in-part of and claims priority to U.S. application Ser. No. 11/966,851 and International Application No. PCT/US2007/089124, both filed Dec. 28, 2007, the disclosures of all three of which are incorporated herein by reference.

ACKNOWLEDGEMENT OF GOVERNMENT SUPPORT

This work was supported by National Institutes of Health Grant No. 1 F32 AR053803-01 (NRSA Fellowship). Therefore, the Government of the United States has certain rights in this invention.

FIELD OF THE INVENTION

This disclosure concerns the use of agonists of AMP-activated protein kinase (AMPK) for improving exercise and modifying energy metabolism in a subject. The disclosure also provides methods of treating muscle wasting diseases and disorders and promoting muscle tone in sedentary subjects. The disclosure also relates to a combination of AMPK and peroxisome proliferator-activated receptor (PPAR)δ agonists for improving exercise performance in a subject, and methods for identifying compounds that modulate gene expression profiles associated with muscle tone, endurance or performance.

BACKGROUND

Skeletal muscle is an adaptive tissue composed of multiple myofibers that differ in their metabolic and contractile properties including oxidative slow-twitch (type I), mixed oxidative/glycolytic fast-twitch (type IIa) and glycolytic fast-twitch (type IIb) myofibers (Fluck et al., Rev. Physiol. Biochem. Pharmacol., 146:159-216, 2003; Pette and Staron, Microsc. Res. Tech., 50:500-509, 2000). Type I muscle fibers preferentially express enzymes that oxidize fatty acids, contain slow isoforms of contractile proteins and are more resistant to fatigue than are glycolytic muscle fibers (Fluck et al., Rev. Physiol. Biochem. Pharmacol., 146:159-216, 2003; Pette and Staron, Microsc. Res. Tech., 50:500-509, 2000). Type II fibers preferentially metabolize glucose and express the fast isoforms of contractile proteins (Fluck et al., Rev. Physiol. Biochem. Pharmacol, 146:159-216, 2003; Pette and Staron, Microsc. Res. Tech., 50:500-509, 2000).

Endurance exercise training triggers a complex remodeling program in skeletal muscle that progressively enhances performance in athletes such as marathon runners, mountain climbers and cyclists. This involves changes in metabolic programs and structural proteins within the myofibers that alter the energy substrate utilization and contractile properties that act to reduce muscle fatigue (Fluck et al., Rev. Physiol. Biochem. Pharmacol, 146:159-216, 2003; Pette and Staron, Microsc. Res. Tech., 50:500-509, 2000). Training based adaptations in the muscle are linked to increases in the expression of genes involved in the slow-twitch contractile apparatus, mitochondrial respiration and fatty acid oxidation (Holloszy and Coyle, J. Appl. Physiol., 56:831-838, 1984; Booth and Thomason, Physiol. Rev., 71:541-585, 1991; Schmitt et al., Physiol. Genomics, 15:148-157, 2003; Yoshioka et al., FASEB J., 17:1812-1819, 2003; Mahoney et al., FASEB J., 19:1498-1500, 2005; Mahoney and Tarnopolsky, Phys. Med. Rehabil Clin. N. Am., 16:859-873, 2005; Siu at al., J. Appl Physiol, 97:277-285, 2004; Garnier et al., FASEB J., 19:43-52, 2005; Short et al., J. Appl Physiol, 99:95-102, 2005; Timmons et al., FASEB J., 19:750-760, 2005). Such exercise training-related adaptations can improve performance and protect against obesity and related metabolic disorders (Wang at al., P. Biol, 2:e294, 2004; Koves at al., J. Biol. Chem., 280:33588-33598, 2005). Moreover, skeletal muscles rich in oxidative slow-twitch fibers are resistant to muscle wasting (Minnaard et al., Muscle Nerve. 31:339-48, 2005).

SUMMARY

The disclosure also provide a method of treating a muscle wasting disease, muscle atrophy or aging comprising administering to a subject a composition comprising an AMPK agonist, wherein the muscle tone, mass or endurance is promoted. In one embodiment, the method comprises treating a subject that may have an immobilized limb or which may be immobilized due to other medical treatments to promote or maintain muscle tone in the subject.

The disclosure demonstrates that unexpected finding that orally active AMPK agonists are sufficient as a single agent to improve exercise endurance by nearly 45% in non-exercised subjects.

The disclosure provides a method for enhancing an exercise effect in a subject, comprising administering to a subject an AMP kinase (AMPK) agonist wherein an exercise effect is enhanced. The AMPK agonist can be any AMPK agonist, derivatives, salts or esters thereof. In one embodiment, the AMPK agonist is AICAR. The method can further comprise administering to the subject an effective amount of a PPARδ agonist (e.g., GW1516), thereby further enhancing the exercise effect in the subject. The subject can be a racing animal including a human, equine, or canine.

The disclosure further comprises a method for identifying the use of performance-enhancing substances in an exercise-trained subject comprising determining in a biological sample taken from an exercise-trained subject the presence of an AMPK agonist and/or expression of one or more molecules listed in Tables 2, 4 or 6.

The disclosure also provides a composition comprising an AMPK agonist and a PPARδ agonist in a pharmaceutically acceptable carrier. The composition may be an energy supplement, beverage, food product or pharmaceutical. The AMPK agonist or PPAR agonist can be a salt, ester, prodrug, precursor or derivative thereof.

This disclosure illustrates that, despite expectations to the contrary, pharmacological activation of AMPK or endogenous PPARδ in adults, promote remodeling of skeletal muscle to an oxidative phenotype or increase running endurance in such subjects. In addition, agonist-induced activation of endogenous PPARδ in combination with exercise led to a unique "gene expression signature" in skeletal muscle, which was distinct from the gene expression profile obtained by either exercise or drug intake alone, and revealed direct interactions between PPARδ and exercise-induced kinases (such as AMPK α1 and/or AMPK 2).

These and other discoveries described herein serve as the basis for disclosed methods. For example, it can now be appreciated that PPARδ agonists (e.g., GW1516) used in combination with exercise can enhance exercise-induced effects, such as to improve exercise endurance (e.g., running endurance) even more than may be achieved by exercise alone. In another example, the expression of one or more genes and/or proteins that are uniquely regulated by the combination of exercise and PPARδ agonist administration can be used to identify subjects using drugs to enhance exercise performance. In still other examples, the newly identified protein complexes, including PPARδ and exercise-induced kinases (such as AMPK α1 and/or AMPK α2), can be used to identify agents that have potential to affect PPARδ-regulated gene networks and the corresponding downstream biochemical and/or physiological effects.

The foregoing and other features will become more apparent from the following detailed description of several embodiments, which proceeds with reference to the accompanying figures.

BRIEF DESCRIPTION OF THE FIGURES

FIG. 1A is a series of bar graphs showing the effects of orally administered PPARδ agonist (GW1516) on mRNA expression levels of three biomarkers of fatty acid oxidation, uncoupling protein 3 (UCP3), carnitine palmitoyltransferase I (mCPT I), and pyruvate dehydrogenase kinase, isoenzyme 4 (PDK4), in quadriceps muscle isolated from sedentary vehicle-treated (V), sedentary GW1516-treated (GW), sedentary VP16-PPARδ transgenic (TG), and sedentary wild-type littermates of VP16-PPARδ transgenic mice (WT). Data are presented as mean±SEM of N=4-9 mice each analyzed in triplicate. * Represents a statistically significant difference between V and GW1516 groups ($p<0.05$, unpaired student's t-test), or TG and WT groups ($p<0.05$, unpaired student's t-test).

FIG. 1B-D are a series of bar graphs showing the regulation of oxidative genes UCP3, mCPT I, and PDK4 by GW1516 (GW) in wild-type (WT) and PPARδ null (KO) primary muscle cells. * represents statistical significance between V and indicated groups ($p<0.05$, One Way ANOVA; post hoc: Dunnett's Multiple Comparison Test).

FIG. 1E is a series of bar graphs showing running endurance of vehicle-treated sedentary (V; open bars) and GW1516-treated sedentary (GW; black bars) mice before (Week 0) and after (Week 5) treatment. Running endurance is quantified by the amount of time for which (left panel) or the distance (right panel) animals in each group ran on the treadmill. Data is represented as mean±SD values from N=6 mice.

FIG. 2A shows digital images of representative meta-chromatically stained frozen cross-sections of gastrocnemius muscle from vehicle-treated, sedentary (V), GW1516-treated, sedentary (GW), vehicle-treated, exercised (Tr) and GW1516-treated, exercised (Tr+GW) mice. Type I (slow oxidative) fibers are darkly stained. FIG. 2B is a bar graph showing the percentage of type I fibers (as a percentage of the total fibers) in V, GW, Tr, and Tr+GW gastrocnemius (N=3). FIG. 2C is a bar graph showing the fold change in mitochondrial DNA to nuclear DNA ratio in V (left bar), GW (left center bar), Tr (right center bar), and Tr+GW (right bar) groups of mice (N=9). Data in (B) and (C) are presented as mean±SEM. In each bar graph, * represents a statistical difference between V and the group(s) indicated by asterisk ($p<0.05$, One-Way ANOVA; post hoc: Dunnett's Multiple Comparison Test).

FIGS. 3A-D are a series of bar graphs showing gene expression in quadriceps muscle isolated from V, GW, Tr and Tr+GW groups. FIG. 3A shows the relative gene expression levels of biomarkers for fatty acid oxidation (UCP3, mCPT I, PDK4; from left to right). (B) shows the relative gene expression levels of biomarkers for fatty acid storage (SCD1, FAS, SREBP1c). (C) shows the relative gene expression levels of biomarkers for fatty acid uptake (FAT/CD36, LPL). Data is presented as mean±SEM of N=9 mice, each analyzed in triplicate. * represents statistically significant difference between V and the group(s) indicated by asterisk ($p<0.05$, One Way ANOVA; post hoc: Dunnett's Multiple Comparison Test). (D) shows images of Western blots illustrating protein expression levels of oxidative biomarkers (myoglobin, UCP3, CYCS, SCD1) and loading control (tubulin) in protein lysates prepared from quadriceps (N=3).

FIG. 7A is a series of Western blot images showing AMPK activation by exercise. The levels of phospho-AMPK (phospho-AMPK) and total-AMPK in quadriceps muscle of sedentary (Sed/C57B1) and exercise-trained (Tr/C57B1) mice (N=5-7) are shown.

FIG. 7B is a series of Western blot images showing AMPK activation by VP16-VP16-PPARδ over-expression. The levels of phospho-AMPK (phospho-AMPK) and total-AMPK in quadriceps muscle of sedentary wild-type or transgenic mice (Sed/WT or Sed/TG) are shown.

FIGS. 9A-H show the expression of (A) UCP3, (B) mCPT I, (C) PDK4, (D) SCD1, (E) ATP citrate lyase, (F) HSL, (G) mFABP, and (H) LPL transcripts in quadriceps of mice treated with vehicle (V), GW 1516 (GW), AICAR (AI) and the combination of the two drugs (GW+AI) for 6 days. Data is presented as mean±SEM of N=6 mice in each group, analyzed in triplicate. * Indicates statistically significant difference between V and indicated groups ($p<0.05$, One Way ANOVA; post hoc: Dunnett's Multiple Comparison Test).

SEQUENCE INFORMATION

Figure 2A:
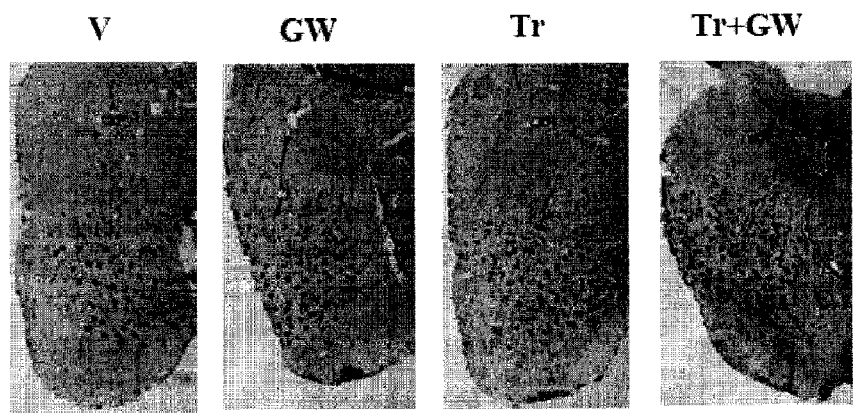
FIGS. 2A-C show the effects of administration of a PPARδ agonist, GW1516, on the gastrocnemius muscle of sedentary (V or GW) or trained (Tr or Tr+GW) mice.

Nucleic acid and amino acid sequences may be referred to herein by GenBank accession number. It is understood that the sequences given such GenBank accession numbers are incorporated by reference as they existed and were known as of Dec. 29, 2007.

DETAILED DESCRIPTION

Unless specifically noted otherwise herein, the definitions of the terms used are standard definitions used in the art of pharmaceutical sciences. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the disclosure. Nothing herein is to be construed as an admission that the inventors are not entitled to antedate such disclosure by virtue of prior disclosure.

Given the numerous benefits of exercise on general health, identification of orally active agents that mimic or potentiate the genetic effects of endurance exercise is a long-standing, albeit elusive, medical goal. High doses of certain natural extracts such as resveratrol can improve endurance (Lagouge et al., 2006). The aerobic effects of resveratrol are thought to depend on activation of SIRT1-PGC1a coactivator complex in skeletal muscle. However, the downstream transcriptional factor(s) targeted by SIRT1/PGC1a in mediating these effects are not known. More importantly, both SIRT1/PGC1a and resveratrol activate multiple targets, and thus whether there is a specific signaling pathway that can be selectively activated by a synthetic drug to improve endurance is not known.

Exercise training activates a number of transcriptional regulators and serine-threonine kinases in skeletal muscles that contribute to metabolic reprogramming (Bassel-Duby and Olson, 2006). Overexpression of a constitutively active PPARδ (VP16-PPARδ) in skeletal muscles of transgenic mice preprograms an increase in oxidative muscle fibers, enhancing running endurance by nearly 100% in untrained adult mice (Wang et al., 2004). One of the best understood serine-threonine kinases is AMP-activated protein kinase (AMPK), a master regulator of cellular and organism metabolism.

AMP kinase agonists such as AICAR have been studied for insulin regulation, diabetes and obesity. However, AMP kinases have not previously been demonstrated to promote muscle tone or to improve endurance or exercise. The disclosure provides that AMPK agonists provide a beneficial effect for muscle wasting diseases and disorders, benefits to sedentary subject or immobilized limbs and in combination with PPARd agonist an unexpected synergistic effect.

The disclosure demonstrates that PPARδ agonist such as, for example, GW1516 (shown to be bioactive in humans) enables mice to run 60%-75% longer and further than the nontreated controls only; however, such an effect is only seen when administration of a PPARδ agonist is combined with exercise training. This "super-endurance phenotype" is linked to a transcriptional boost provided by exercise-activated AMPK resulting in a novel endurance gene signature (see, e.g., FIG. 10L)

The disclosure also demonstrated that this super-endurance phenotype can be obtained, in the absence of exercise training, by orally active AMPK agonist and that such an AMPK agonist is sufficient as a single agent to improve running endurance by nearly 45% in nonexercised subjects.

AMP-activated protein kinase (AMPK) and AMPK kinase (AMPKK) comprise a protein kinase cascade. The AMPK cascade regulates fuel production and utilization intracellularly. For example, low cellular fuel (e.g., an increase in AMP concentration) increase AMPK activity. Once activated, AMPK functions either to conserve ATP or to promote alternative methods of ATP generation.

5'AMP-activated protein kinase or AMPK consists of three proteins (subunits) that together make a functional enzyme that plays a role in cellular energy homeostasis. It is expressed in a number of tissues, including the liver, brain, and skeletal muscle. Activation of AMPK has been shown to activate hepatic fatty acid oxidation and ketogenesis, inhibit cholesterol synthesis, lipogenesis, and triglyceride synthesis, inhibit adipocyte lipolysis and lipogenesis, stimulate skeletal muscle fatty acid oxidation and muscle glucose uptake, and modulate insulin secretion by pancreatic beta-cells.

Triggering the activation of AMPK can be carried out with increasing concentrations of AMP. The γ subunit of AMPK undergoes a conformational change so as to expose the active site (Thr-172) on the α subunit. The conformational change of the γ subunit of AMPK can be accomplished under increased concentrations of AMP. Increased concentrations of AMP will give rise to the conformational change on the γ subunit of AMPK as two AMP bind the two Bateman domains located on that subunit. This role of AMP is demonstrated in experiments that show AMPK activation via an AMP analogue 5-amino-4-imidazolecarboxamide ribotide (ZMP) which is derived from 5-amino-4-imidazolecarboxamide riboside (AICAR).

As muscles contract, ATP is hydrolyzed, forming ADP. ADP then helps to replenish cellular ATP by donating a phosphate group to another ADP, forming an ATP and an AMP. As more AMP is produced during muscle contraction, the AMP: ATP ratio dramatically increases, leading to the allosteric activation of AMPK.

Various AMPK agonist are known in the art. Methods and compositions comprising such AMPK agonist are provided herein. The use of such AMPK agonist improves muscle tone and muscle mass, as well as improve endurance compared to subjects not receiving such AMPK agonists. Various AMPK agonists are described herein and are known in the art. In one embodiment, the AMPK agonist comprises an AICAR compound. Other compounds useful in the method of the disclosure include analogs of AICAR (such as those disclosed in U.S. Pat. No. 5,777,100, hereby incorporated by reference herein) and prodrugs or precursors of AICAR (such as those disclosed in U.S. Pat. No. 5,082,829, hereby incorporated by reference herein), which increase the bioavailability of AICAR, all of which are well-known to those of ordinary skill in the art. Other activators of AMPK include those described in U.S. Patent Publication No. 20060287356 to Iyengar et al. (the disclosure of which is incorporated herein by reference). Conventionally known AMPK-activating compounds include, in addition to the aforementioned leptin, adiponectin, and metformin, AICAR (5-aminoimidazole-4-carboxamide). Other AMPK agonists include, but are not limited to, DRL-16536 (Dr. Reddy's/Perlecan Pharma), BG800 compounds (Betagenon), furan-2-carboxylic acid derivative (Hanall, K R; see also Int'l. Application Publ. WO/2008/016278, incorporated herein by reference), A-769662 (Abbott) (structure I; see also, Cool et al., Cell Metabol. 3:403-416, 2006); AMPK agonist under development by Metabasis as set forth in Int'l. Publication No. WO/2006/033709; MT-39 series of compounds (Mercury Therapeutics); and AMPK agonist under development by TransTech Pharma.

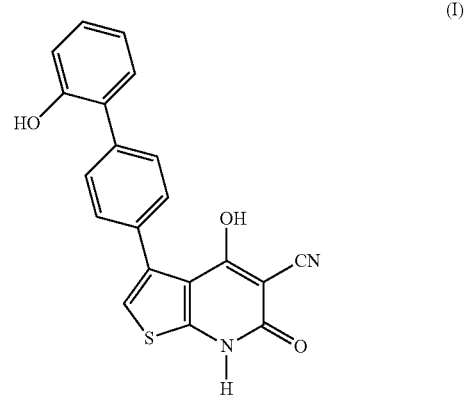 [SMILES: N#Cc1c(O)c2c(-c3ccc(-c4ccccc4O)cc3)csc2[nH]c1=O]

(I)

AICAR, for example, is taken into the cell and converted to ZMP, an AMP analog that has been shown to activate AMPK. ZMP acts as an intracellular AMP mimic, and, when accumulated to high enough levels, is able to stimulate AMPK activity (Corton, J. M. et. al. Eur. J. Biochem. 229: 558 (1995)). However, ZMP also acts as an AMP mimic in the regulation of other enzymes, and is therefore not a specific AMPK activator (Musi, N. and Goodyear, L. J. Current Drug Targets—Immune, Endocrine and Metabolic Disorders 2:119 (2002)).

The disclosure provides methods for stimulating an "exercise conditioned state" in a subject. The method includes administering to a subject an AMPK agonist in an amount sufficient to simulate an energy deficient state in a subject. By "energy deficient state" refers to a state in which the γ subunit of AMPK undergoes a conformation change, there is increased catabolism of fat stores in a subject or there is conservation of ATP energy stores or a metabolic state found in an exercising individual. The exercise conditioned state can be accomplished in the absence of exercise using the AMPK agonist of the disclosure (an "exercise-free conditioning"). However, it will be recognized, that although administration of an AMPK agonist can promote an exercise conditioned state, it may be desirable or appropriate for a subject to perform exercise conditioning even with the administration of an AMPK agonist.

Stimulating and exercise conditioned states not only has benefits to athletic training, but also provides benefits to subject who, do to injury, disease or disorder, are unable to exercise a limb/muscle or where the subject is sedentary or immobilized. By stimulating an exercise conditioned state the subject can maintain muscle tone and/or mass in the limb or muscle and promote health or recovery.

Exercise is known to have many effects on subjects that perform it. Exercise effects at the molecular, biochemical, and/or cellular levels (e.g., modified regulation of genes and/or gene networks and corresponding proteins involved in energy substrate utilization and contractile properties of muscle) form the basis of physiological effects that are observed at the tissue, organ, and/or whole body levels (e.g., increased cardiorespiratory endurance, muscular strength, muscular endurance, and/or flexibility, and/or improvements in body appearance).

In general terms, exercise is the performance of some physical activity. A single episode (also referred to as a bout) of physical activity is performed for a particular duration and at a particular intensity. If more than one bout of exercise is performed, separate bouts of exercise may have the same or different durations and/or the same or different intensities.

In some embodiments, a single bout of exercise may last for up to 30 minutes, up to 45 minutes, up to 60 minutes, up to 90 minutes, up to 2 hours, up to 2.5 hours, up to 3 hours, or even longer. Typically, in the absence of a prior exercise history, repeated episodes of physical activity are needed to achieve an exercise-induced effect (such as, increased aerobic capacity or increase running endurance) for a PPARδ agonist to be effective. However, the administration of an AMPK agonist eliminates that need for exercise to see an effective exercise-induced or promoting effect.

Thus, in some disclosed methods, no exercise is needed when an AMPK agonist is taken alone or prior to an PPARδ agonist. However, in some instances bouts of physical activity may be repeated within a single day; for instance, up to 2 bouts of exercise per day, up to 3 bouts of exercise per day, up to 4 bouts of exercise per day, up to 5 bouts of exercise per day, or even more bouts per day. Some professional athletes or racing mammals may exercise in repeated bouts for a total of 8 hours or more a day. In other method embodiments, bouts (or repeated bouts) of exercise are performed on a daily basis, 6 times per week, 5 times per week, 4 times per week or 3 times per week. In at least some of the disclosed methods, exercise may continue for at least 2 weeks, for at least 4 weeks, for at least 6 weeks, for at least 3 months, for at least 6 months, for at least 1 year, for at least 3 years, or indefinitely (for the lifetime of the subject).

Exercise generally is performed at an intensity that is more than the usual (e.g., average, median, normal standard, or normoactive) activity for a subject, and/or at or less than the maximum activity achievable by a subject performing a particular exercise. Any known indicator of physical performance can be used to determine whether a subject is performing more than a usual amount of activity, including, for instance, measuring heart rate, repetition rate (e.g., revolutions per second, minutes per mile, lifts per minute, and many others), and/or force output. In some methods, a bout of exercise is performed at sub-maximal intensity; for instance, at about 10% maximal intensity, 25% maximal intensity, 50% maximal intensity, or 75% maximal intensity. In other methods, a bout of exercise is performed at 40%-50% maximal heart rate, 50%-60% maximal heart rate, 60%-70% maximal heart rate, or 75%-80% maximal heart rate, where maximum heart rate for a human subject is calculated as: 220 bps−(age of the subject).

Exercise is generally grouped into three types: (i) flexibility exercise (such as, stretching), which is believed to, at least, improve the range of motion of muscles and joints; (ii) aerobic exercise; and (iii) anaerobic exercise (such as, weight training, functional training or sprinting) which is believed to, at least, increase muscle strength and mass.

Aerobic exercise refers to a physical activity in which oxidative or aerobic metabolism (as compared to glycolytic or anaerobic metabolism) substantially predominates in exercised skeletal muscles. In particular method embodiments, a subject performs one or more aerobic exercises. Exemplary aerobic exercises include, without limitation, aerobics, calisthenics, cycling, dancing, exercise machines (rowing machine, cycling machine (e.g., inclined or upright), climbing machine, elliptical trainers, and/or skiing machines), basketball, football, baseball, soccer, footbag, housework, jogging, martial arts, massage, pilates, rowing, running, skipping, swimming, walking, yoga, boxing, gymnastics, badminton, cricket, track and field, golf, ice hockey, lacrosse, rugby, tennis, or combinations thereof.

The disclosed methods contemplate enhancing any known or observable effect of exercise (such as an aerobic exercise, like walking or running). In particular methods, running endurance (e.g., running distance and/or running time) is enhanced. In another embodiment, the methods and compositions are useful for treating a subject having muscle immobility, muscle wasting disease or disorder or a sedentary subject. In one such embodiment, muscle tone or mass is improved or maintained in a subject having muscle immobility, muscle wasting disease or disorder or a sedentary activity compared to a subject that does not receive a composition of the disclosure (e.g., an AMPK agonist, or a combination of an AMPK agonist or PPAR agonist). In one embodiment, the compositions and methods of the disclosure can reduce muscle loss or the rate of muscle loss in a subject having a muscle wasting disease by 5%, 10%, 20%, 30%, 40%, 50%, 60%, 70%, 80%, 90% or more compared to a subject not receiving a composition of the disclosure.

Muscle weakness, tone, and atrophy result from a number of diseases and disorders including denervation or prolonged muscle disuse. When deprived of regular exercise, muscle fibers lose both bulk and length, producing a visible loss of muscle size and contour and apparent emaciation or deformity in the affected area. Even slight atrophy usually causes some loss of motion or power. Atrophy usually results from neuromuscular disease or injury. However, muscle tone, atrophy and weakness may also stem from certain metabolic, cardiovascular or endocrine disorders and prolonged immobility. Some muscle atrophy also occurs with aging. The compositions of the disclosure are useful for treating such muscle weakness, tone and atrophy comprising administering an AMPK agonist alone or in combination with a PPARd agonist.

Muscle wasting disease includes muscle weakness and atrophy that typically begin in a limb (e.g., hand, arm, or leg). Eventually, weakness and atrophy spread to the trunk, neck, tongue, larynx, pharynx, and legs; progressive respiratory muscle weakness leads to respiratory insufficiency. Other findings include muscle flaccidity, fasciculations, hyperactive deep tendon reflexes, slight leg muscle spasticity, dysphagia, impaired speech, excessive drooling, and depression.

Fibrous scar tissue formation, pain, and loss of serum proteins from severe burns can limit muscle movement, resulting in atrophy. Muscle atrophy is a late sign of irreversible ischemia, along with contractures, paralysis, and loss of pulses. Herniated disk can cause muscle weakness, disuse, and ultimately, atrophy. Hypercortisolism may cause limb weakness and eventually atrophy. Hypothyroidism can cause weakness and atrophy of proximal limb muscles. Injuries that result in immobilization of a limb can lead to muscle atropy and muscle wasting including, but not limited to, meniscal tears or broken bones or other cartilage injuries resulting from prolonged knee or limb immobility. Multiple sclerosis is a degenerative disease that cause arm and leg atrophy as a result of chronic progressive weakness; spasticity and contractures may also develop. Osteoarthritis eventually causes atrophy proximal to involved joints as a result of progressive weakness and disuse. Parkinson's disease causes muscle rigidity, weakness, and disuse producing muscle atrophy. Peripheral nerve trauma or injury to or prolonged pressure on a peripheral nerve leads to muscle weakness and atrophy. Peripheral neuropathy can lead to muscle weakness that progresses slowly to flaccid paralysis and eventually atrophy. Distal extremity muscles are generally affected first. Associated findings include loss of vibration sense; paresthesia, hyperesthesia, or anesthesia in the hands and feet; mild to sharp, burning pain; anhidrosis; glossy red skin; and diminished or absent deep tendon reflexes. Damaged spinal nerve roots can cause muscle atrophy as well as weakness. Rheumatoid arthritis causes muscle atrophy in the late stages of this disorder, as joint pain and stiffness decrease range of motion and discourage muscle use. Spinal cord injury or trauma can produce severe muscle weakness and flaccid, then spastic, paralysis, eventually leading to atrophy. Stroke may produce contralateral or bilateral weakness and eventually atrophy of the arms, legs, face, and tongue. Associated signs and symptoms depend on the site and extent of vascular damage and may include dysarthria, aphasia, ataxia, apraxia, agnosia, and ipsilateral paresthesia or sensory loss. Prolonged steroid therapy can interfere with muscle metabolism and can lead to atrophy, most prominently in the limbs. As mentioned above, prolonged immobilization from bed rest, casts, splints, or traction may cause muscle weakness and atrophy. Any of these diseases or disorder can be treated with a composition or combination of compositions of the disclosure. Other muscle wasting disease or disorders are recognized in the art.

The disclosure provides compositions and methods useful for treating such disease and disorders by promoting or maintaining muscle mass or tone. For example, administering an AMPK agonist such as AICAR alone or in combination with a PPARd agonist can promote muscle tone or mass. In healthy subjects this can contribute to an enhanced exercise effect. In subjects with a potential for losing muscle mass or having a muscle wasting disease or disorder the compositions and methods of the disclosure can slow or eliminate the rate of such muscle atrophy.

Enhancing an exercise effect (such as running endurance) means that such effect is improved in a subject more than would have occurred by exercise alone. In some method embodiments, an enhanced exercise effect is determined by discontinuing administration of an AMPK agonist or a PPARδ agonist in the subject and observing (e.g., qualitatively or quantitatively) a reduction in the exercise effect of interest (e.g., aerobic endurance, such as running endurance). In some instances, an exercise effect of interest such as a AMPK-agonist induced effect or the PPARδ-enhanced portion of which is lost upon discontinuance of an AMPK agonist or PPARδ agonist administration, will be reduced by at least about 5%, by at least about 10%, by at least about 20%, by at least about 30%, or by at least about 50% as compared to the magnitude of the effect with exercise alone.

The disclosed methods can be performed in any subject capable of performing physical activity {e.g., aerobic exercise). In some method embodiments, a subject is a living multi-cellular vertebrate organism {e.g., human and/or non-human animals). In other exemplary methods, a subject is a mammal (including humans and/or non-human mammals such as veterinary or laboratory mammals) or, in more particular examples, a racing mammal (such as a horse, a dog, or a human). In still other methods, a subject is an adult, an exercise-trained subject, or a healthy subject. Some representative adult, human subjects are 16 years old or older, 18 years old or older, or 21 years old or older. In some embodiment, the subject does not perform any routine exercise. In some embodiment, some representative exercised-trained subjects have performed physical activity (such described in detail above) for at least 4 weeks, for at least 6 weeks, for at least 3 months, or for at least 6 months. In some examples the subject is healthy, for example, is a subject in which no known disease or disorder has been diagnosed or would be apparent after reasonable inquiry to an ordinarily skilled physician in the field to which the disease or disorder pertains.

As described more fully below, the AMPK agonist may be administered orally, parenterally, intramuscularly, intravascularly or by any appropriate route. A subject can be any mammalian subject (e.g., equine, canine, or human). An AMPK agonist is particularly useful in combination with agents that promote muscle fiber development and growth. Examples of such agents include agonists of the PPAR family of proteins.

PPARs are members of the nuclear receptor superfamily of ligand-inducible transcription factors. They form heterodimers with retinoid X receptors (RXRs) and bind to consensus DNA sites composed of direct repeats of hexameric DNA sequences separated by 1 bp. In the absence of ligand, PPAR-RXR heterodimers recruit corepressors and associated histone deacetylases and chromatin-modifying enzymes, silencing transcription by so-called active repression (Ordentlich et al., Curr. Top. Microbiol. Immunol, 254:101-116, 2001; Jepsen and Rosenfeld, J. Cell Sci, 115:689-698, 2002; Privalsky, Ann. Rev. Physiol, 66:315-360, 2004). Ligand binding induces a conformational change in PPAR-RXR complexes, releasing repressors in exchange for coactivators. Ligand-activated complexes recruit the basal transcriptional machinery, resulting in enhanced gene expression. PPARs bind to lower-affinity ligands generated from dietary fat or intracellular metabolism. In keeping with their roles as lipid sensors, ligand-activated PPARs turn on feed-forward metabolic cascades to regulate lipid homeostasis via the transcription of genes involved in lipid metabolism, storage, and transport.

Three PPAR isotypes exist in mammals: α (also known as NR1C1), γ (also known as NR1C3), and δ (also known as β or NR1C2). PPARδ is expressed in most cell types with relative abundance (Smith, Biochem. Soc. Trans., 30(6): 1086-1090, 2002), which led to early speculation that it may serve a "general housekeeping role" (Kliewer et al., Proc. Natl. Acad. Sci. U.S. A, 91:7355-7359, 1994). More recently, PPARδ transgenic mouse models and discoveries aided by the development of high-affinity PPARδ agonists have revealed PPARδ as a key transcriptional regulator with effects in diverse tissues including fat, skeletal muscle, and the heart (for review see, e.g., Barish et al., J. Clin. Invest., 116(3):590-597, 2006).

Targeted expression of a constitutively active PPARδ receptor (VP16-PPARδ) transgene in rodent skeletal muscle promoted remodeling of skeletal muscle to an oxidative phenotype and increased running endurance in unexercised adult mice (PLoC Biol, 2:e294, 2004). The observed PPARδ-mediated reprogramming of muscle fibers involved the increased expression of genes related to fatty acid oxidation, mitochondrial respiration, oxidative metabolism, and slow-twitch contractile apparatus (Wang et al., PLoC. Biol., 2:e294, 2004). These VP16-PPARδ transgenic mice, who had a phenotype similar to endurance-trained athletes, but who had had no exercise training, suggest that pharmacological activation of endogenous PPARδ in an adult, sedentary subject might provide an exercise effect without the actual exercise. Given the numerous benefits of exercise on general health, identification of orally active agents that mimic the effects of exercise is a long standing, albeit elusive medical goal.

Disclosed herein are methods for enhancing an exercise effect or promote/maintain muscle tone or mass in a subject comprising administering an AMPK agonist sufficient to produce an exercise effect, enhance mitochondrial expression or activity. In one embodiment, the subject is a an exercising subject. In another embodiment, the subject is a sedentary subject. In another embodiment, the subject is immobilized or has an immobilized limb. The disclosure further includes administering to the subject an effective amount of a PPARδ agonist (e.g., GW1516). The exercise effect that is enhanced can be, for example, improved running endurance (such as, improved running distance or improved running time or a combination thereof, increased fatty acid oxidation in at least one skeletal muscle of the subject, and/or body fat {e.g., white adipose tissue) reduction). In some method embodiments, a subject is a mammal (such as a racing mammal, like a horse, a dog, or a human), and/or an adult, and/or an exercise-trained subject. In other exemplary methods, a PPARδ agonist is administered on the same day(s) on which the AMPK agonist is administered or on the same day upon which physical exertion will be performed. In another embodiment, the combination of an AMPK agonist and PPAR agonist are administered on the same day as a physical exertion will be performed. In some methods, administration of the AMPK agonist is by oral administration, intravenous injection, intramuscular injection, and/or subcutaneous injection. In other method embodiments, the effective amount of the AMPK agonist is from about 1 mg per day to about 20 mg per day in a single dose or in divided doses. In some methods, administration of the PPARδ agonist is by oral administration, intravenous injection, intramuscular injection, and/or subcutaneous injection. In other method embodiments, the effective amount of the PPARδ agonist is from about 1 mg per day to about 20 mg per day in a single dose or in divided doses.

The disclosed methods envision the use of any PPARδ agonist. Preferably such agonist would be non-toxic in the subject to which it is administered. Exemplary PPARδ agonists include GW1516, L-165041 (as described by, e.g., Leibowitz et al., FEBS Lett., 473(3):333-336, 2000), any one or more compounds described in PCT Publication Nos. WO/2006/018174, WO/2005/113506, WO/2005/105754, WO/2006/041197, WO/2006/032023, WO/01/00603, WO/02/092590, WO/97/28115, WO/97/28149, WO/97/27857, WO/97/28137, WO/97/27847, and/or WO/98/27974, and/or a published U.S. national phase application or issued U.S. patent corresponding to any of the foregoing (each of which is expressly incorporated herein by reference). Moreover, other PPARδ agonists can be identified using the methods described, for example, in PCT Publication No. WO/1998/049555 or any corresponding published U.S. national phase application or issued U.S. patent (each of which is expressly incorporated herein by reference).

In a specific example, the PPARδ agonist is GW1516 (also referred to in the art as GW501516). GW1516 is (2-methyl-4(((4-methyl-2-(4-trifluoromethylphenyl)-1,3-thiazol-5-yl)methyl)sulfanyl)phenoxy)acetic acid as has been shown to be is bioactive in humans (Sprecher et al., Arterioscler. Thromb. Vasc. Biol. 27(2): 359-65, 2007). In specific examples, GW1516 is administered orally, for example 1 mg-20 mg/day, such as 2.5 mg or 10 mg per day.

Disclosed herein are methods for enhancing or stimulating one or more exercise effects by combining, at least, an AMPK agonist with physical activity and/or administration of one or more PPARδ agonists.

The disclosed methods envision the use of any method of administration, dosage, and/or formulation of an AMPK agonist alone or in combination with a PPARδ agonist that has the desired outcome of enhancing an exercise effect in a subject receiving the formulation, including, without limitation, methods of administration, dosages, and formulations well known to those of ordinary skill in the pharmaceutical arts.

AMPK agonist of the disclosure may be administered in the form of a drug to a human or an animal. Alternatively, the AMPK agonist may be incorporated into a variety of foods and beverages or pet foods so as to be consumed by humans or animals. The AMPK agonist may be applied to a common food or beverage; or may be applied to a functional food or beverage, a food for a subject suffering a disease, or a food for specified health use, the food (or beverage) bearing a label thereon indicating that it has a physiological function; for example, energy supplement, exercise enhancer or the like.

The AMPK agonist alone or in combination with a PPARδ agonist may be formulated into a drug product; for example, a peroral solid product such as a tablet or a granule, or a peroral liquid product such as a solution or a syrup.

Modes of administering an AMPK agonist (or a formulation including a PPARδ agonist) in a disclosed method include, but are not limited to, intrathecal, intradermal, intramuscular, intraperitoneal (ip), intravenous (iv), subcutaneous, intranasal, epidural, intradural, intracranial, intraventricular, and oral routes. In a specific example, the AMPK agonist or AMPK agonist and PPARδ agonist is administered orally. Other convenient routes for administration of an AMPK agonist (or a formulation including a PPARδ agonist) include for example, infusion or bolus injection, topical, absorption through epithelial or mucocutaneous linings (for example, oral mucosa, rectal and intestinal mucosa, and the like) ophthalmic, nasal, and transdermal. Administration can be systemic or local. Pulmonary administration also can be employed (for example, by an inhaler or nebulizer), for instance using a formulation containing an aerosolizing agent.

In specific method embodiments, it may be desirable to administer an AMPK agonist or an AMPK agonist and PPARδ agonist locally. This may be achieved by, for example, local or regional infusion or perfusion, topical application (for example, wound dressing), injection, catheter, suppository, or implant (for example, implants formed from porous, non-porous, or gelatinous materials, including membranes, such as sialastic membranes or fibers), and the like.

In other embodiments, a pump (such as a transplanted minipump) may be used to deliver an AMPK agonist or a combination of an AMPK agonist and a PPARδ agonist (or a formulation including a PPARδ agonist) (see, e.g., Langer Science 249, 1527, 1990; Sefton Crit. Rev. Biomed. Eng. 14, 201, 1987; Buchwald et al., Surgery 88, 507, 1980; Saudek et al., N. Engl. J. Med. 321, 574, 1989). In another embodiment, an AMPK agonist (or a formulation including a PPARδ agonist) is delivered in a vesicle, in particular liposomes (see, e.g., Langer, Science 249, 1527, 1990; Treat et al., in Liposomes in the Therapy of Infectious Disease and Cancer, Lopez-Berestein and Fidler (eds.), Liss, N.Y., pp. 353-365, 1989).

In yet another method embodiment, an AMPK agonist alone or in combination with a PPARδ agonist can be delivered in a controlled-release formulation. Controlled-release systems, such as those discussed in the review by Langer (Science 249, 1527 1990), are known. Similarly, polymeric materials useful in controlled-released formulations are known (see, e.g., Ranger et al., Macromol. ScL Rev. Macromol. Chem. 23, 61, 1983; Levy et al., Science 228, 190, 1985; During et al., Ann. Neurol. 25, 351, 1989; Howard et al., J. Neurosurg. 71, 105, 1989). For example, an agonists may be coupled to a class of biodegradable polymers useful in achieving controlled release of a compound, including polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The disclosed methods contemplate the use of any dosage form of an AMPK agonist alone or in combination with a PPARδ agonist (or formulation containing the same) that delivers the agonist(s) and achieves a desired result. Dosage forms are commonly known and are taught in a variety of textbooks, including for example, Allen et al., Ansel's Pharmaceutical Dosage Forms and Drug Delivery Systems, Eighth Edition, Philadelphia, Pa.: Lippincott Williams & Wilkins, 2005, 738 pages. Dosage forms for use in a disclosed method include, without limitation, solid dosage forms and solid modified-release drug delivery systems (e.g., powders and granules, capsules, and/or tablets); semi-solid dosage forms and transdermal systems (e.g., ointments, creams, and/or gels); transdermal drug delivery systems; pharmaceutical inserts (e.g., suppositories and/or inserts); liquid dosage forms (e.g., solutions and disperse systems); and/or sterile dosage forms and delivery systems (e.g., parenterals, and/or biologies). Particular exemplary dosage forms include aerosol (including metered dose, powder, solution, and/or without propellants); beads; capsule (including conventional, controlled delivery, controlled release, enteric coated, and/or sustained release); caplet; concentrate; cream; crystals; disc (including sustained release); drops; elixir; emulsion; foam; gel (including jelly and/or controlled release); globules; granules; gum; implant; inhalation; injection; insert (including extended release); liposomal; liquid (including controlled release); lotion; lozenge; metered dose (e.g., pump); mist; mouthwash; nebulization solution; ocular system; oil; ointment; ovules; powder (including packet, effervescent, powder for suspension, powder for suspension sustained release, and/or powder for solution); pellet; paste; solution (including long acting and/or reconstituted); strip; suppository (including sustained release); suspension (including lente, ultre lente, reconstituted); syrup (including sustained release); tablet (including chewable, sublingual, sustained release, controlled release, delayed action, delayed release, enteric coated, effervescent, film coated, rapid dissolving, slow release); transdermal system; tincture; and/or wafer. Typically, a dosage form is a formulation of an effective amount (such as a therapeutically effective amount) of at least one active pharmaceutical ingredient (such as an AMPK agonist or PPARδ agonist) with pharmaceutically acceptable excipients and/or other components (such as one or more other active ingredients). An aim of a drug formulation is to provide proper administration of an active ingredient (such as an AMPK agonist alone or in combination with a PPARδ agonist) to a subject. A formulation should suit the mode of administration. The term "pharmaceutically acceptable" means approved by a regulatory agency of the federal or a state government or listed in the U.S. Pharmacopoeia or other generally recognized pharmacopoeia for use in animals, and, more particularly, in humans. Excipients for use in exemplary formulations include, for instance, one or more of the following: binders, fillers, disintegrants, lubricants, coatings, sweeteners, flavors, colorings, preservatives, diluents, adjuvants, and/or vehicles. In some instances, excipients collectively may constitute about 5%-95% of the total weight (and/or volume) of a particular dosage form.

Pharmaceutical excipients can be, for instance, sterile liquids, such as water and/or oils, including those of petroleum, animal, vegetable, or synthetic origin, such as peanut oil, soybean oil, mineral oil, sesame oil, and the like. Water is an exemplary carrier when a formulation is administered intravenously. Saline solutions, blood plasma medium, aqueous dextrose, and glycerol solutions can also be employed as liquid carriers, particularly for injectable solutions. Oral formulations can include, without limitation, pharmaceutical grades of mannitol, lactose, starch, magnesium stearate, sodium saccharine, cellulose, magnesium carbonate, and the like. A more complete explanation of parenteral pharmaceutical excipients can be found in Remington, The Science and Practice of Pharmacy, 19th Edition, Philadelphia, Pa.: Lippincott Williams & Wilkins, 1995, Chapter 95. Excipients may also include, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. Other examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. A formulation, if desired, can also contain minor amounts of wetting or emulsifying agents, or pH buffering agents.

A dosage regimen utilizing a PPARδ agonist is selected in accordance with a variety of factors including type, species, age, weight, sex and physical condition of the subject; the route of administration; and/or the particular PPARδ agonist formulation employed. An ordinarily skilled physician or veterinarian can readily determine an effective amount of a PPARδ agonist (or formulation thereof) useful for enhancing an exercise effect in a subject.

In some embodiments involving oral administration, oral dosages of an AMPK agonist alone or in combination with a PPARδ agonist will generally range between about 0.001 mg per kg of body weight per day (mg/kg/day) to about 100 mg/kg/day, and such as about 0.01-10 mg/kg/day (unless specified otherwise, amounts of active ingredients are on the basis of a neutral molecule, which may be a free acid or free base). For example, an 80 kg subject would receive between about 0.08 mg/day and 8 g/day, such as between about 0.8 mg/day and 800 mg/day. A suitably prepared medicament for once a day administration would thus contain between 0.08 mg and 8 g, such as between 0.8 mg and 800 mg. In some instance, formulation including an AMPK agonist alone or in combination with a PPARδ agonist may be administered in divided doses of two, three, or four times daily. For administration twice a day, a suitably prepared medicament as described above would contain between 0.04 mg and 4 g, such as between 0.4 mg and 400 mg. Dosages outside of the aforementioned ranges may be necessary in some cases. Examples of daily dosages that may be given in the range of 0.08 mg to 8 g per day include 0.1 mg, 0.5 mg, 1 mg, 2.5 mg, 5 mg, 10 mg, 25 mg, 50 mg, 100 mg, 200 mg, 300 mg, 400 mg, 500 mg, 600 mg, 800 mg, 1 g, 2 g, 4 g and 8 g. These amounts can be divided into smaller doses if administered more than once per day (e.g., one-half the amount in each administration if the drug is taken twice daily).

For some method embodiments involving administration by injection (e.g., intravenously or subcutaneous injection), a subject would receive an injected amount that would deliver the active ingredient in approximately the quantities described above. The quantities may be adjusted to account for differences in delivery efficiency that result from injected drug forms bypassing the digestive system. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, such as for example 0.1 mg/ml, 0.3 mg/ml, or 0.6 mg/ml, and administered in amounts per day equivalent to the amounts per day stated above. For example, an 80 kg subject, receiving 8 ml twice a day of an intravenous formulation having a concentration of active ingredient of 0.5 mg/ml, receives 8 mg of active ingredient per day.

In other method embodiments, an AMPK agonist (or a formulation thereof) can be administered at about the same dose throughout a treatment period, in an escalating dose regimen, or in a loading-dose regime (for example, in which the loading dose is about two to five times a maintenance dose). In some embodiments, the dose is varied during the course of an AMPK agonist formulation usage based on the condition of the subject receiving the composition, the apparent response to the composition, and/or other factors as judged by one of ordinary skill in the art. In some embodiments long-term administration of an AMPK agonist or combination therapy (or formulation thereof) is contemplated, for instance in order to effect sustained enhancement of an exercise effect (such as aerobic endurance, e.g., running endurance).

Also disclosed herein are methods for identifying the use of performance-enhancing substances in an exercise-trained subject, which include determining in a biological sample taken from an exercise-trained subject (e.g., a skeletal muscle biopsy) the presence of ZMP or other non-naturally occurring AMP analog and/or the expression of the molecules listed in Table 2 or listed in Table 4, or a subset thereof, such as expression of at least 1, at least 5, at least 10, at least 20, at least 40 of the molecules listed in Table 2 or in Table 4.

In some methods for identifying the use of performance-enhancing substances in an exercise-trained subject the presence of a ZMP or AMP analog will be measured alone or in combination with whether (i) expression is upregulated in one or more of (such as at least 5, at least 10, at least 20, at least 35, or all of) adipose differentiation related protein; stearoyl-Coenzyme A desaturase 2; acetyl-Coenzyme A acetyltransferase 2; ATP citrate lyase; adiponectin, C1Q and collagen domain containing; diacylglycerol O-acyltransferase 2; lipase, hormone sensitive; monoglyceride lipase; resistin; CD36 antigen; fatty acid binding protein 4, adipocyte; lipoprotein lipase; microsomal glutathione S-transferase 1; GPI-anchored membrane protein 1; dual specificity phosphatase 7; homeodomain interacting protein kinase 3; insulin-like growth factor binding protein 5; protein phosphatase 2 (formerly 2A), regulatory subunit A (PR 65), beta isoform; protein tyrosine phosphatase-like (proline instead of catalytic arginine); member b; CCAAT/enhancer binding protein (C/EBP), alpha; nuclear receptor subfamily 1, group D, member 2(Reverb-b); transferring; archain 1; solute carrier family 1 (neutral amino acid transporter), member 5; RIKEN cDNA 1810073N04 gene; haptoglobin; retinol binding protein 4, plasma; phosphoenolpyruvate carboxykinase 1, cytosolic; cell death-inducing DFFA-like effector c; interferon, alpha-inducible protein 27; carbonic anhydrase 3; cysteine dioxygenase 1, cytosolic; DNA segment, Chr 4, Wayne State University 53, expressed; dynein cytoplasmic 1 intermediate chain 2; Kruppel-like factor 3 (basic); thyroid hormone responsive SPOT14 homolog (Rattus); cytochrome P450, family 2, subfamily e, polypeptide 1; complement factor D (adipsin); and/or transketolase; and/or (ii) expression is downregulated in one or more of gamma-glutamyl carboxylase; 3-oxoacid CoA transferase 1; solute carrier family 38, member 4; annexin A7; CD55 antigen; RIKEN cDNA 1190002H23 gene; fusion, derived from t(12; 16) malignant liposarcoma (human); lysosomal membrane glycoprotein 2; and/or neighbor of Punc E1 1, such as 1, 2, 3, 4, 5, 6, 7, 8 or 9 of these molecules.

Exemplary methods for identifying the use of performance-enhancing substances in an exercise-trained subject involve determining protein expression and/or determining expression of a gene encoding the protein. Such methods are routine in the art. In some examples, the level of protein or nucleic acid expression is quantified. Methods of identifying an agent having potential to enhance exercise performance in a subject also are disclosed herein. Such methods can include (i) providing a first component comprising a PPARδ receptor or an AMPK-binding fragment thereof; (ii) providing a second component comprising an AMP-activated protein kinase (AMPK), AMPKα1, AMPKα2, or a PPARδ-binding fragment of any thereof; (iii) contacting the first component and the second component with at least one test agent under conditions that would permit the first component and the second component to specifically bind to each other in the absence of the at least one test agent; and (iv) determining whether the at least one test agent affects the specific binding of the first component and the second component to each other. An effect on specific binding of the first component and the second component to each other identifies the at least one test agent as an agent having potential to enhance exercise performance in a subject.

The use of performance-enhancing substances (PES), particularly by children and professional athletes, has been in the news because of potential adverse health consequences and the arguable effects that such practices have on moral development of the individual and on fair athletic competition for all (Committee on Sports Medicine and Fitness, Reginald L. Washington, MD, Chairperson, Pediatrics, 115(4): 1103-1106, 2005). One of the discoveries provided herein is that certain genes (and/or the proteins encoded thereby) are uniquely regulated by a combination of exercise and a pharmaceutical agent (a PPARδ agonist) that results in enhanced physical performance (see Table 2). In some cases, the particular genes (and/or proteins encoded thereby) were up- or down-regulated by the combined treatment but were not affected by either intervention alone. In other cases, the particular genes (and/or proteins encoded thereby) were not affected by the combined treatment but were up- or down-regulated by one or both intervention when practiced alone. The unique regulation of these genes (and/or the encoded proteins) makes them useful markers (either alone or in any combination) for identifying exercising subjects who are taking (or receiving) PES.

A PES is any substance taken in nonpharmacologic doses specifically for the purpose of improving sports performance (e.g., by increasing strength, power, speed, or endurance (ergogenic) or by altering body weight or body composition). Exemplary PES include the following: (i) pharmacologic agents (prescription or nonprescription) taken in doses that exceed the recommended therapeutic dose or taken when the therapeutic indication(s) are not present (e.g., using decongestants for stimulant effect, using bronchodilators when exercise-induced bronchospasm is not present, increasing baseline methylphenidate hydrochloride dose for athletic competition); (ii) agents used for weight control, including stimulants, diet pills, diuretics, and laxatives, when the user is in a sport that has weight classifications or that rewards leanness; (iii) agents used for weight gain, including over-the-counter products advertised as promoting increased muscle mass; (iv) physiologic agents or other strategies used to enhance oxygen-carrying capacity, including erythropoietin and red blood cell transfusions (blood doping); (v) any substance that is used for reasons other than to treat a documented disease state or deficiency; (vi) any substance that is known to mask adverse effects or detectability of another performance-enhancing substance, and/or (vii) nutritional supplements taken at super physiologic doses or at levels greater than required to replace deficits created by a disease state, training, and/or participation in sports. In one example the PES is as AMPK agonist (e.g., one that provides an MP analog) or GW1516.

For example, to quantify the levels of an AMPK agonist such as AICAR in a sample of body fluid such as serum, as sensitive LC-MS/MS assay can be used. The assay utilizes a structurally related analog to the AMPK activator as an internal standard. For example, the adenosine analog tubercidin (4-amino-7-beta-D-ribufuranosyl-7H-pyrrolo[2,3-d]pyrimindine; 7-beta-D-riburuanosyl-7H-pyrrolo[2,3-d]pyrimindin-4-amine; 7-deazaadenosine) is structurally related to AICAR and can be used as the internal standard when assaying for AICAR. Samples containing a known concentration of the internal standard can be directly analyzed by LC-MS/MS. The substance of interest and the internal standard can be resolved on a LC-MS/MS (tandem mass spec) system, for example, suing a hydrophobic column with a solvent or acidified solvent gradient, and detected as positive ions using selective reaction monitoring. Other analyzers and detection methods known in the art can be used. A standard curve over one two, three or four orders of magnitude constructed using agonist-spiked serum can be constructed to facilitate quantification of AICAR levels.

The biomarkers of substance-induced performance enhancement identified herein and useful in a disclosed method include one or more (or any combination of) of an AMP analog or the genes (and/or proteins encoded thereby) listed in Table 2, and in some examples listed in Table 4. In particular method embodiments, at least 2, at least 3, at least 5, at least 7, at least 10, at least 15, at least 20, at least 30, or at least 40 of the genes (and/or proteins encoded thereby) listed in Table 2 (or Table 4) are detected in a disclosed method. In one example at least one gene (and/or protein encoded thereby) from each class listed in Table 2 (e.g., cytokines, fat metabolism) is analyzed.

In one embodiment, upregulated expression is detected for one or more of the following genes (or proteins encoded thereby): adipose differentiation related protein; stearoyl-Coenzyme A desaturase 2; acetyl-Coenzyme A acetyltransferase 2; ATP citrate lyase; adiponectin, C1Q and collagen domain containing; diacylglycerol O-acyltransferase 2; lipase, hormone sensitive; monoglyceride lipase; resistin; CD36 antigen; fatty acid binding protein 4, adipocyte; lipoprotein lipase; microsomal glutathione S-transferase 1; GPI-anchored membrane protein 1; dual specificity phosphatase 7; homeodomain interacting protein kinase 3; insulin-like growth factor binding protein 5; protein phosphatase 2 (formerly 2A), regulatory subunit A (PR 65), beta isoform; protein tyrosine phosphatase-like (proline instead of catalytic arginine); member b; CCAAT/enhancer binding protein (C/EBP), alpha; nuclear receptor subfamily 1, group D, member 2 (Reverb-b); transferring; archain 1; solute carrier family 1 (neutral amino acid transporter), member 5; RIKEN cDNA 1810073N04 gene; haptoglobin; retinol binding protein 4, plasma; phosphoenolpyruvate carboxykinase 1, cytosolic; cell death-inducing DFFA-like effector c; interferon, alpha-inducible protein 27; carbonic anhydrase 3; cysteine dioxygenase 1, cytosolic; DNA segment, Chr 4, Wayne State University 53, expressed; dynein cytoplasmic 1 intermediate chain 2; Kruppel-like factor 3 (basic); thyroid hormone responsive SPOT14 homolog (Rattus); cytochrome P450, family 2, subfamily e, polypeptide 1; complement factor D (adipsin); and/or transketolase. In particular method embodiments, upregulation of at least 2, at least 3, at least 5, at least 7, at least 10, at least 15, at least 20, at least 30, or at least 38 of the foregoing genes (and/or proteins encoded thereby) are detected in a disclosed method. In other method embodiments, downregulated expression is detected in one or more of the following genes (and/or proteins encoded thereby): gamma-glutamyl carboxylase; 3-oxoacid CoA transferase 1; solute carrier family 38, member 4; annexin A7; CD55 antigen; RIKEN cDNA 1190002H23 gene; fusion, derived from t(12; 16) malignant liposarcoma (human); lysosomal membrane glycoprotein 2; and/or neighbor of Punc El 1. In particular method embodiments, downregulation of at least 2, at least 3, at least 5, or at least 7 of the foregoing genes (and/or proteins encoded thereby) are detected in a disclosed method.

In still other method embodiments, a combination of upregulated genes (and/or proteins encoded thereby) and downregulated genes (and/or proteins encoded thereby) as described above is detected in a sample from a subject (such as, an exercised or exercise-trained subject).

Yet other method embodiments involve the detection in a sample of a combination of an AMP analog (e.g., ZMP) and one or more of the above-described upregulated genes (and/or proteins encoded thereby) and/or the above-described downregulated genes (and/or proteins encoded thereby), and/or the above-described exercise-regulated genes that are not affected by exercise combined with PPARδ administration.

Disclosed methods may be used for detecting PES use in any subject capable of taking or receiving one or more such PES. In some method embodiments, a subject is a living multi-cellular vertebrate organism (e.g., human and/or non-human animals). In other exemplary methods, a subject is a mammal (including humans and/or non-human mammals) or, in more particular examples, a racing mammal (such as a horse, a dog, or a human). In still other methods, a subject is an exercise-trained subject. Some representative exercised-trained subjects have performed physical activity (such described in detail above) for at least 4 weeks, for at least 6 weeks, for at least 3 months, or for at least 6 months. Other exercise-trained subjects may be student athletes and/or professional athletes (including, in some examples, non-human professional athletes, such as race horses and/or racing dogs).

Any sample from a subject (e.g., a biological sample) in which can be detected an AMP analog and/or one or more genes and/or proteins uniquely regulated by exercise in combination with PPARδ agonist intake (as described in detail throughout this specification) is contemplated for use in a disclosed method. Exemplary samples for use in a disclosed method include blood, saliva, urine, muscle biopsy (e.g., skeletal muscle biopsy), cheek swab, fecal sample, sweat, and/or sperm.

Methods of detecting the expression of genes and/or proteins in a sample (e.g., biological sample) are very well known (see, e.g., U.S. Pat. Nos. 6,911,307; 6,893,824; 5,972,692; 5,972,602; 5,776,672; 7,031,847; 6,816,790; 6,811,977; 6,806,049; 6,203,988; and/or 6,090,556). In particular embodiments, expression of one or more genes identified herein can be detected by any method of nucleic acid amplification (such as, polymerase chain reaction (PCR) or any adaptation thereof, ligase chain reaction, transcription-based amplification systems, cycling probe reaction, Qβ replicase amplification, strand displacement amplification, and/or rolling circle amplification), solid-surface hybridization assays (such as Northern blot, dot blot, gene chips, and/or reversible target capture), solution hybridization assays (such as MAP technology (which uses a liquid suspension array of 100 sets of 5.5 micron probe-conjugated beads, each internally dyed with different ratios of two spectrally distinct fluorophores to assign it a unique spectral address)), and/or in situ hybridization. Various of the foregoing nucleic acid detection methods are described in detail in the review by Wolcott (Clin. Microbiol. Rev., 5(4):370-386, 1992). Other detailed and long-established protocols for practicing some such nucleic acid detection methods are found in Sambrook et al., Molecular Cloning: A Laboratory Manual, 2nd edition, Cold Spring Harbor Laboratory Press, 1989; Sambrook et al., Molecular Cloning: A Laboratory Manual, 3rd edition, Cold Spring Harbor Press, 2001; Ausubel et al., Current Protocols in Molecular Biology, Greene Publishing Associates, 1992 (and Supplements to 2000); and/or Ausubel et al., Short Protocols in Molecular Biology: A Compendium of Methods from Current Protocols in Molecular Biology, 4th edition, Wiley & Sons, 1999.

In other embodiments, expression of one or more proteins encoded by corresponding genes identified herein can be detected by Western blot, immunohistochemistry, immunoprecipitation, antibody microarrays, ELISA, and/or by functional assay (e.g., kinase assay, ATPase assay, substrate (or ligand) binding assay, protein-protein binding assay, or other assay suitable for measuring a particular protein function).

If the pattern of expression identified in the test subject is similar to that shown in Table 2 (e.g., the genes shown as upregulated and downregulated in Table 2 are observed in the subject to be upregulated and downregulated, respectively), this indicates that the subject is taking a PES, such as a PPARδ agonist (e.g., GW1516). In contrast, if the pattern of expression identified in the test subject is different to that shown in Table 2 (e.g., the genes shown as upregulated and downregulated in Table 2 are observed in the subject to be not differentially expressed or show a different pattern of regulation), this indicates that the subject is not taking a PES, such as a PPARδ agonist (e.g., GW 1516).

This disclosure identifies a previously unknown protein-protein interaction between PPARδ and particular exercise-induced kinases (e.g., AMPK, such as the AMPKα1 and/or AMPKα2 subunit(s) of AMPK). The interaction between PPARδ and AMPK may have important functional outcomes, such as enhancing exercise performance (e.g., aerobic exercise performance, such as running endurance) in a subject.

The foregoing discoveries enable methods for identify agents, e.g., having potential to enhance exercise performance (e.g., aerobic exercise performance, such as running endurance) in a subject. In some such methods, agents that affect (e.g., enhance, weaken, or substantially disrupt) the protein-protein interaction are identified. In other such methods, agents that affect (e.g., increase, decrease, or substantially eliminate) AMPK-dependent phosphorylation of a PPARδ complex are identified.

An "agent" is any substance or any combination of substances that is useful for achieving an end or result; for example, a substance or combination of substances useful for modulating a protein activity associated with AMPK activation cascade (e.g., AMPK-dependent phosphorylation of a PPARδ complex), or useful for modifying or affecting a protein-protein interaction (e.g., PPARδ-AMPK interaction) or ATP metabolism. Any agent that has potential (whether or not ultimately realized) to modulate any aspect of the PPARδ-AMPK interaction disclosed herein is contemplated for use in the screening methods of this disclosure.

Exemplary agents include, but are not limited to, peptides such as, for example, soluble peptides, including but not limited to members of random peptide libraries (see, e.g., Lam et al., Nature, 354:82-84, 1991; Houghten et al., Nature, 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., Cell, 72:767-778, 1993), antibodies (including, but not limited to, polyclonal, monoclonal, humanized, anti-idiotypic, chimeric or single chain antibodies, and Fab, F(ab')2 and Fab expression library fragments, and epitope-binding fragments thereof), small organic or inorganic molecules (such as, so-called natural products or members of chemical combinatorial libraries), molecular complexes (such as protein complexes), or nucleic acids.

Libraries (such as combinatorial chemical libraries) useful in the disclosed methods include, but are not limited to, peptide libraries (see, e.g., U.S. Pat. No. 5,010,175; Furka, Int. J. Pept. Prot. Res., 37:487-493, 1991; Houghton et al., Nature, 354:84-88, 1991; PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Natl. Acad. Sci. USA, 90:6909-6913, 1993), vinylogous polypeptides (Hagihara et al., J. Am. Chem. Soc, 114:6568, 1992), nonpeptidal peptidomimetics with glucose scaffolding (Hirschmann of al., J. Am. Chem. Soc, 114:9217-9218, 1992), analogous organic syntheses of small compound libraries (Chen et al., J. Am. Chem. Soc, 116:2661, 1994), oligocarbamates (Cho et al., Science, 261: 1303, 1003), and/or peptidyl phosphonates (Campbell et al., J. Org. Chem., 59:658, 1994), nucleic acid libraries (see Sambrook et al. Molecular Cloning, A Laboratory Manual, Cold Springs Harbor Press, N.Y., 1989; Ausubel et al., Current Protocols in Molecular Biology, Green Publishing Associates and Wiley Interscience, N.Y., 1989), peptide nucleic acid libraries (see, e.g., U.S. Pat. No. 5,539,083), antibody libraries (see, e.g., Vaughn of al., Nat. Biotechnol, 14:309-314, 1996; PCT App. No. PCT/US96/10287), carbohydrate libraries (see, e.g., Liang et al., Science, 274:1520-1522, 1996; U.S. Pat. No. 5,593,853), small organic molecule libraries (see, e.g., benzodiazepines, Baum, C&EN, January 18, page 33, 1993; isoprenoids, U.S. Pat. No. 5,569,588; thiazolidionones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514) and the like.

Libraries useful for the disclosed screening methods can be produce in a variety of manners including, but not limited to, spatially arrayed multipin peptide synthesis (Geysen, et al., Proc Natl. Acad. Sci., 81(13):3998-4002, 1984), "tea bag" peptide synthesis (Houghten, Proc Natl. Acad. Sci., 82(15): 5131-5135, 1985), phage display (Scott and Smith, Science, 249:386-390, 1990), spot or disc synthesis (Dittrich et al., Bioorg. Med. Chem. Lett., 8(17):2351-2356, 1998), or split and mix solid phase synthesis on beads (Furka et al., Int. J. Pept. Protein Res., 37(6):487-493, 1991; Lam et al., Chem. Rev., 97 (2):411-448, 1997). Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one embodiment, high throughput screening methods involve providing a combinatorial chemical or peptide library containing a large number of potential therapeutic compounds (e.g., affectors of AMPK-PPARδ protein-protein interactions). Such combinatorial libraries are then screened in one or more assays as described herein to identify those library members (particularly chemical species or subclasses) that display a desired characteristic activity (such as increasing or decreasing an AMPK-PPARδ protein-protein interaction). The compounds thus identified can serve as conventional "lead compounds" or can themselves be used as potential or actual therapeutics. In some instances, pools of candidate agents may be identify and further screened to determine which individual or subpools of agents in the collective have a desired activity. PPARδ forms a protein-protein interaction with AMPK or one or more of its subunits (such as AMPKα1 and/or AMPKcc2). Agents that affect (e.g., increase or decrease) an AMPK-PPARδ interaction or AMP-dependent phosphorylation of a PPARδ complex may have the effect of enhancing exercise performance (e.g., aerobic exercise performance, such as running endurance) in a subject and, therefore, are desirable to identify.

In screening methods described here, tissue samples, isolated cells, isolated polypeptides, and/or test agents can be presented in a manner suitable for high-throughput screening; for example, one or a plurality of isolated tissue samples, isolated cells, or isolated polypeptides can be inserted into wells of a microtitre plate, and one or a plurality of test agents can be added to the wells of the microtitre plate. Alternatively, one or a plurality of test agents can be presented in a high-throughput format, such as in wells of microtitre plate (either in solution or adhered to the surface of the plate), and contacted with one or a plurality of isolated tissue samples, isolated cells, and/or isolated polypeptides under conditions that, at least, sustain the tissue sample or isolated cells or a desired polypeptide function and/or structure. Test agents can be added to tissue samples, isolated cells, or isolated polypeptides at any concentration that is not lethal to tissues or cells, or does not have an adverse effect on polypeptide structure and/or function. It is expected that different test agents will have different effective concentrations. Thus, in some methods, it is advantageous to test a range of test agent concentrations.

Disclosed methods envision, as appropriate, the use of PPARδ or AMPK (such as AMPKα1 or AMPKcc2) or functional fragments of any thereof as contained, independently, in a subject, one or a plurality of cells or cellular extracts, one or a plurality of tissue or tissue extracts, or as an isolated polypeptide. PPARδ ligand optionally is included (or is omitted) in disclosed methods.

A "direct association" between two or more polypeptides (such as, PPARδ and AMPK (such as AMPKα1 or AMPKα2) is characterized by physical contact between at least a portion of the interacting polypeptides that is of sufficient affinity and specificity that, for example, immunoprecipitation of one of the polypeptides also will specifically precipitate the other polypeptide; provided that the immunoprecipitating antibody does not also affect the site(s) involved in the interaction. A direct association between polypeptides also may be referred to as a "protein-protein interaction." The binding of one polypeptide to another in a protein-protein interaction {e.g., PPARδ to AMPK (or AMPKα1 and/or AMPKα2) and vice versa) is considered "specific binding". Agents that affect an AMPK-PPARδ interaction can be identified by a variety of assays, including solid-phase or solution-based assays. In an exemplary solid-phase assay, PPARδ or an AMPK-binding fragment thereof and AMPK or a subunit thereof (such as AMPKα1 and/or AMPKα2) or a PPARδ-binding fragment thereof are mixed under conditions in which PPARδ and AMPK (or its subunit(s) or functional fragments) normally interact {e.g., co-immunoprecipitate). One of the binding partners is labeled with a marker such as biotin, fluorescein, EGFP, or enzymes to allow easy detection of the labeled component. The unlabeled binding partner is adsorbed to a support, such as a microtiter well or beads. Then, the labeled binding partner is added to the environment where the unlabeled binding partner is immobilized under conditions suitable for interaction between the two binding partners. One or more test compounds, such as compounds in one or more of the above-described libraries, are separately added to individual microenvironments containing the interacting binding partners. Agents capable of affecting the interaction between the binding partners are identified, for instance, as those that increase or decrease (e.g., increase) retention or binding of the signal (i.e., labeled binding partner) in the reaction microenvironment, for example, in a microtiter well or on a bead for example. As discussed previously, combinations of agents can be evaluated in an initial screen to identify pools of agents to be tested individually, and this process is easily automated with currently available technology.

In other embodiments, solution phase selection can be used to screen large complex libraries for agents that specifically affect protein-protein interactions (see, e.g., Boger et al., Bioorg. Med. Chem. Lett., 8(17):2339-2344, 1998); Berg et al., Proc. Natl. Acad. Sci., 99(6):3830-3835, 2002). In one such example, each of two proteins that are capable of physical interaction (for example, PPARδ (or AMPK-binding fragments thereof) and AMPK or AMPKα1 or AMPKα2 (or PPARδ-binding fragments of any thereof) are labeled with fluorescent dye molecule tags with different emission spectra and overlapping adsorption spectra. When these protein components are separate, the emission spectrum for each component is distinct and can be measured. When the protein components interact, fluorescence resonance energy transfer (FRET) occurs resulting in the transfer of energy from a donor dye molecule to an acceptor dye molecule without emission of a photon. The acceptor dye molecule alone emits photons (light) of a characteristic wavelength. Therefore, FRET allows one to determine the kinetics of two interacting molecules based on the emission spectra of the sample. Using this system, two labeled protein components are added under conditions where their interaction resulting in FRET emission spectra. Then, one or more test compounds, such as compounds in one or more of the above-described libraries, are added to the environment of the two labeled protein component mixture and emission spectra are measured. An increase in the FRET emission, with a concurrent decrease in the emission spectra of the separated components indicates that an agent (or pool of candidate agents) has affected (e.g., enhanced) the interaction between the protein components.

Interactions between PPARδ (or AMPK-binding fragments thereof) and AMPK or AMPKα1 or AMPKα2 (or PPARδ-binding fragments of any thereof) also can be determined (e.g., quantified) by co-immunoprecipitation of the relevant component polypeptides (e.g., from cellular extracts), by GST-pull down assay (e.g., using purified GST-tagged bacterial proteins), and/or by yeast two-hybrid assay, each of which methods is standard in the art. Conducting any one or more such assays in the presence and, optionally, absence of a test compound can be used to identify agents that improve or enhance (or, in other embodiments, decrease or inhibit) the interaction between PPARδ (or AMPK-binding fragments thereof) and AMPK or AMPKα1 or AMPKα2 (or PPARδ-binding fragments of any thereof) in the presence of a test compound as compared to in the absence of the test compound or as compared to some other standard or control.

In certain embodiments, one or more AMPK (such as AMPKα1 and/or AMPKcc2)-binding fragments of PPARδ and/or one or more PPARδ-binding fragments of AMPK (such as AMPKα1 and/or AMPKα2) are used. Polypeptide fragments having the desired binding activities can be identified by making a series of defined PPARδ fragments and/or AMPK (such as AMPKα1 or AMPKα2) fragments using methods standard in the art. For example, cDNA encoding the protein(s) of interest (e.g., PPARδ or AMPK) can be serially truncated from the 3' or 5' end (provided that a start codon is engineered into 5' truncations) using conveniently located restriction enzyme sites (or other methods) and leaving intact (or otherwise correcting) the proper reading frame. Conveniently, a nucleic acid sequence encoding an epitope tag (such as a FLAG tag) is placed in frame with (and substantially adjacent to) the truncated protein-encoding sequence to produce a nucleic acid sequence encoding an epitope-tagged protein fragment. The epitope-tagged protein fragment can be expressed in any convenient expression system (such as a bacterial expression system), isolated or not, and mixed with a sample containing a protein or other protein fragment to which the epitope-tagged protein fragment may bind. An antibody specific for the tag (or other region of the protein fragment) can be used to immunoprecipitate the fragment of interest together with any protein(s) or protein fragment(s) that bind to it. Protein(s) or protein fragment(s) that bind to the epitope-tagged protein fragment of interest can be particular identified, e.g., by Western blot.

In particular methods, the formation of a PPARδ-AMPK (such as AMPKα1 and/or AMPKcc2) complex (including complexes including one or both of PPARδ-binding AMPK fragments and/or AMPK-binding PPARδ fragments) or the affinity of PPARδ (or AMPK-binding fragments thereof) and AMPK (or PPARδ-binding fragments thereof) for each other is increased when the amount of such complex or the binding affinity is at least 5%, at least 10%, at least 20%, at least 30%, at least 50%, at least 100% or at least 250% higher than a control measurement (e.g., in the same test system prior to addition of a test agent, or in a comparable test system in the absence of a test agent). In other particular methods, the formation of a PPARδ-AMPK (such as AMPKα1 and/or AMPKcc2) complex (including complexes including one or both of PPARδ-binding AMPK fragments and/or AMPK-binding PPARδ fragments) or the affinity of PPARδ (or AMPK-binding fragments thereof) and AMPK (or PPARδ-binding fragments thereof) for each other is decreased when the amount of such complex or the binding affinity is at least 5%, at least 10%, at least 20%, at least 30%, at least 50%, at least 100% or at least 250% lower than a control measurement (e.g., in the same test system prior to addition of a test agent, or in a comparable test system in the absence of a test agent).

Disclosed are methods of screening test agents for those that affect (e.g., increase or decrease) AMPK (e.g., AMPKα1 and/or AMPKα2)-dependent phosphorylation of the PPARδ complex. Agents that affect AMPK-dependent phosphorylation of the PPARδ complex can be identified by a variety of assays, such adaptations of solid-phase- or solution-based assays described above, where the end point to be detected is phosphorylation of one or more components of the PPARδ complex.

Methods for detecting protein phosphorylation are conventional (see, e.g., Gloffke, The Scientist, 16(19):52, 2002; Screaton et al., Cell, 119:61-74, 2004) and detection kits are available from a variety of commercial sources (see, e.g., Upstate (Charlottesville, Va., USA), Bio-Rad (Hercules, Calif., USA), Marligen Biosciences, Inc. (Ijamsville, Md., USA), Calbiochem (San Diego, Calif., USA). Briefly, phosphorylated protein (e.g., phosphorylation of one or more components of the PPARδ complex) can be detected using stains specific for phosphorylated proteins in gels. Alternatively, antibodies specific phosphorylated proteins can be made or commercially obtained. Antibodies specific for phosphorylated proteins can be, among other things, tethered to the beads (including beads having a particular color signature) or used in ELISA or Western blot assays.

In one example, a PPARδ complex (or a fragment thereof containing an AMPK phosphorylation site) and AMPK or one or more of it subunits (such as AMPKα1 and/or AMPKcc2) or functional fragments thereof that are capable of phosphorylation are mixed under conditions whereby a PPARδ complex is phosphorylated by AMPK. A PPARδ complex is adsorbed to a support, such as a microtiter well or beads. Then, AMPK (or its one or more subunits (such as AMPKα1 and/or AMPKcc2) or phosphorylation-capable fragments thereof) is added to the environment where the complex is immobilized. A phosphate donor typically is also included in the environment. The phosphate to be donated, optionally, can be labeled. One or more test compounds, such as compounds in one or more of the above-described libraries, are separately added to the individual microenvironments. Agents capable of affecting AMPK-dependent phosphorylation are identified, for instance, as those that enhance (or inhibit) phosphorylation of immobilized PPARδ complex. In embodiments involving a labeled phosphate donor, phosphorylation of immobilized PPARδ complex can be determined by retention or binding of a labeled phosphate in the reaction microenvironment, for example, in a microtiter well or on a bead for example. In other embodiments, such reactions can take place in solution (i.e., with no immobilized components), PPARδ complex can be isolated from the solution (e.g., by immunoprecipitation with PPARδ-specific or phosphate-specific antibodies), and its level of phosphorylation in the presence (and, optionally, absence) of one of more test agents determined as previously discussed. In yet another embodiment, the phosphorylation of an AMPK is measured, wherein an agent that modulates AMPK activity is thus identified as an AMPK agonist.

In particular methods, the phosphorylation of a PPARδ complex is increased when such posttranslational modification is detectably measured or when such posttranslational modification is at least 20%, at least 30%, at least 50%, at least 100% or at least 250% higher than control measurements (e.g., in the same test system prior to addition of a test agent, or in a comparable test system in the absence of a test agent, or in a comparable test system in the absence of AMPK).

In particular methods, the phosphorylation of PPARδ complex is decreased when such posttranslational modification is detectably reduced or when such posttranslational modification is at least 20%, at least 30%, at least 50%, at least 100% or at least 250% lower than control measurements (e.g., in the same test system prior to addition of a test agent, or in a comparable test system in the absence of a test agent, or in a comparable test system in the absence of AMPK).

A PPARδ polypeptide useful in a disclosed screening method is any known PPARδ receptor. Also useful in the disclosed screening methods are homologs, functional fragments, or functional variants of a PPARδ that retains at least AMPK-binding activity as described herein for a prototypical PPARδ polypeptide (see Example 6).

The amino acid sequences of prototypical PPARδ polypeptides (and PPARδ-encoding nucleic acid sequences) are well known. Exemplary PPARδ amino acid sequences and PPARδ-encoding nucleic acid sequences are described, for instance, in U.S. Pat. No. 5,861,274, and U.S. Pat. Appl. Pub. No. 20060154335 (each of which is expressly incorporated herein by reference), and in GenBank Accession Nos. NP_035275 (GI:33859590) (*Mus musculus* amino acid sequence); NM_011145.3 (GI:89001112) (*Mus musculus* nucleic acid sequence); NP_006229 (GI:5453940) (*Homo sapiens* amino acid sequence); NM_006238.3 (GI: 89886454) (*Homo sapiens* nucleic acid sequence); NP_037273 (GI:69S13S4) (*Rattus norvegicus* amino acid sequence); NM_013141.1 (GL6981383) (*Rattus norvegicus* nucleic acid sequence); NP_990059 (gi45382025) (*Gallus gallus* amino acid sequence) or NM_204728.1 (GI: 45382024) (*Gallus gallus* nucleic acid sequence). In some method embodiments, a PPARδ homolog or functional variant shares at least 60% amino acid sequence identity with a prototypical PPARδ polypeptide; for example, at least 75%, at least 80%, at least 85%, at least 90%, at least 95%, or at least 98% amino acid sequence identity with an amino acid sequence as set forth in U.S. Pat. No. 5,861,274, U.S. Pat. Appl. Pub. No. 20060154335, or GenBank Accession No. NP_035275 (GI:33859590) (*Mus musculus* amino acid sequence); NP_006229 (GI:5453940) (*Homo sapiens* amino acid sequence); NP_037273 (Gï0.69$13$4) (*Rattus norvegicus* amino acid sequence); or NP_990059 (gi45382025) {*Gallus gallus* amino acid sequence). In other method embodiments, a PPARδ homolog or functional variant has one or more conservative amino acid substitutions as compared to with a prototypical PPARδ polypeptide; for example, no more than 3, 5, 10, 15, 20, 25, 30, 40, or 50 conservative amino acid changes compared to an amino acid sequence as set forth in U.S. Pat. No. 5,861,274, U.S. Pat. Appl. Pub. No. 20060154335, or GenBank Accession No. NP_035275 (GI: 33859590) (M*Unknown: *s musculus amino acid sequence); NP_006229 (GI:5453940) (*Homo sapiens* amino acid sequence); NP_037273 (Gi.69$13$4) (*Rattus norvegicus* amino acid sequence); or NP_990059 (gi45382025) (*Gallus gallus* amino acid sequence).

Some method embodiments involve a PPARδ functional fragment (such as an AMPK-binding fragment), which can be any portion of a full-length known PPARδ polypeptide, including, e.g., about 20, about 30, about 40, about 50, about 75, about 100, about 150 or about 200 contiguous amino acid residues of same; provided that the fragment retains a PPARδ function of interest (e.g., AMPK binding). PPARδ encompasses known functional motifs (such as ligand-binding domain, a DNA-binding domain, and a transactivation domain).

Mammalian AMP-activated kinase (AMPK) is a heterotrimeric protein composed of 1 alpha subunit, 1 beta subunit, and 1 gamma subunit. There are, at least, two known isoforms of the alpha subunit (α1 and α2). AMPKα1 and AMPKα2 have 90% amino acid sequence identity within their catalytic cores but only 61% in their C-terminal tails (see Online Mendelian Inheritance in Man (OMIM) Database Accession No. 602739; publicly available at the following website: ncbi.nlm.nih.gov/entrez/dispomim.cgi?id=602739).

An AMPK (such as AMPKα1 and/or AMPKα2) polypeptide useful in a disclosed screening method is any known AMPK protein or subunit thereof (such as AMPKα1 and/or AMPKα2). Also useful in the disclosed screening methods are homologs, functional fragments, or functional variants of an AMPK protein or subunit thereof (such as AMPKα1 and/or AMPKα2) that retains at least PPARδ-binding activity as described herein (see Example 6). The amino acid sequences of prototypical AMPK subunits (such as AMPKα1 and/or AMPKα2) (and nucleic acids sequences encoding prototypical AMPK subunits (such as AMPKα1 and/or AMPKα2)) are well known. Exemplary AMPKα1 amino acid sequences and the corresponding nucleic acid sequences are described, for instance, in GenBank Accession Nos. NM_206907.3 (GI: 94557298) (*Homo sapiens* transcript variant 2 REFSEQ including amino acid and nucleic acid sequences); NM_006251.5 (GI:94557300) (*Homo sapiens* transcript variant 1 REFSEQ including amino acid and nucleic acid sequences); NM_001013367.3 (GI:94681060) (*Mus musculus* REFSEQ including amino acid and nucleic acid sequences); NMJ) 01039603.1 (GI:88853844) (*Gallus gallus* REFSEQ including amino acid and nucleic acid sequences); and NM_019142.1 (GI: 11862979XRaJfWS norvegicus REFSEQ including amino acid and nucleic acid sequences). Exemplary AMPKα2 amino acid sequences and the corresponding nucleic acid sequences are described, for instance, in GenBank Accession Nos. NM_006252.2 (GI:46877067) (*Homo sapiens* REFSEQ including amino acid and nucleic acid sequences); NM_178143.1 (GI:54792085) (*Mus musculus* REFSEQ including amino acid and nucleic acid sequences); NM_001039605.1 (GI:88853850) (*Gallus gallus* REFSEQ including amino acid and nucleic acid sequences); and NM_214266.1 (GI:47523597) (*Mus musculus* REFSEQ including amino acid and nucleic acid sequences).

In some method embodiments, a homolog or functional variant of an AMPK subunit shares at least 60% amino acid sequence identity with a prototypical AMPKα1 and/or AMPKα2 polypeptide; for example, at least 75%, at least 80%, at least 85%, at least 90%, at least 95%, or at least 98% amino acid sequence identity with an amino acid sequence as set forth in the GenBank Accession Nos. NM_206907.3; NM_006251.5; NMJ) 01013367.3; NM_001039603.1; NM_019142.1; NM_006252.2; NM_178143.1; NM_001039605.1; or NM_214266.1. In other method embodiments, a homolog or functional variant of an AMPK subunit has one or more conservative amino acid substitutions as compared to a prototypical AMPKα1 and/or AMPKα2 polypeptide; for example, no more than 3, 5, 10, 15, 20, 25, 30, 40, or 50 conservative amino acid changes compared to an amino acid sequence as set forth in as set forth in GenBank Accession Nos. NM_206907.3; NM_006251.5; NM_001013367.3; NM_001039603.1; NM_019142.1; NM_006252.2; NM_178143.1; NM_001039605.1; or NM_214266.1. Exemplary conservative amino acid substitutions have been previously described herein.

Some method embodiments involve a functional fragment of AMPK or a subunit thereof (such as AMPKα1 and/or AMPKα2), including a PPARδ-binding fragment or a fragment with PPARδ phosphorylation activity. Functional fragments of AMPK or a subunit thereof (such as AMPKα1 and/or AMPKα2) can be any portion of a full-length or intact AMPK polypeptide complex or subunit thereof (such as AMPKα1 and/or AMPKα2), including, e.g., about 20, about 30, about 40, about 50, about 75, about 100, about 150 or about 200 contiguous amino acid residues of same; provided that the fragment retains at least one AMPK (or AMPKα1 and/or AMPKα2) function of interest (e.g., PPARδ binding and/or PPARδ phosphorylation activity). Protein-protein interactions between PPARδ and AMPK are believed to involve, at least, an AMPKα subunit (such as AMPKα1 and/or AMPKα2). Moreover, because PPARδ specifically binds both AMPKα1 and AMPKα2 (see Example 6), such interaction likely is mediated by the portions of these AMPKα isoforms that share the most sequence homology (as discussed above). Accordingly, in some method embodiments, an AMPK PPARδ-binding fragment includes a functional fragment encompassing (or consisting of) the catalytic core domain of an alpha subunit of AMPK (such as AMPKα1 and/or AMPKα2).

An "isolated" biological component (such as a polynucleotide, polypeptide, or cell) has been purified away from other biological components in a mixed sample (such as a cell or tissue extract). For example, an "isolated" polypeptide or polynucleotide is a polypeptide or polynucleotide that has been separated from the other components of a cell in which the polypeptide or polynucleotide was present (such as an expression host cell for a recombinant polypeptide or polynucleotide).

The term "purified" refers to the removal of one or more extraneous components from a sample. For example, where recombinant polypeptides are expressed in host cells, the polypeptides are purified by, for example, the removal of host cell proteins thereby increasing the percent of recombinant polypeptides in the sample. Similarly, where a recombinant polynucleotide is present in host cells, the polynucleotide is purified by, for example, the removal of host cell polynucleotides thereby increasing the percent of recombinant polynucleotide in the sample.

Isolated polypeptides or nucleic acid molecules, typically, comprise at least 50%, at least 60%, at least 70%, at least 80%, at least 90%, at least 95% or even over 99% (w/w or w/v) of a sample.

Polypeptides and nucleic acid molecules are isolated by methods commonly known in the art and as described herein. Purity of polypeptides or nucleic acid molecules may be determined by a number of well-known methods, such as polyacrylamide gel electrophoresis for polypeptides, or agarose gel electrophoresis for nucleic acid molecules.

The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. ScL USA 85:2444, 1988; Higgins and Sharp, Gene 73:237-244, 1988; Higgins and Sharp, CABIOS 5:151-153, 1989; Corpet et al., Nucleic Acids Research 16:10881-10890, 1988; Huang, et al., Computer Applications in the Biosciences 8:155-165, 1992; Pearson et al., Methods in Molecular Biology 24:307-331, 1994; Tatiana et al., (1999), FEMS Microbiol. Lett., 174:247-250, 1999. Altschul et al. present a detailed consideration of sequence alignment methods and homology calculations (J. Mol. Biol. 215:403-410, 1990). The National Center for Biotechnology Information (NCBI) Basic Local Alignment Search Tool (BLAST™, Altschul et al., J. Mol. Biol. 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method.

Specific binding refers to the particular interaction between one binding partner (such as a binding agent) and another binding partner (such as a target). Such interaction is mediated by one or, typically, more noncovalent bonds between the binding partners (or, often, between a specific region or portion of each binding partner). In contrast to non-specific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites, specific binding partners involved in a direct association with each other (e.g., a protein-protein interaction) can be competitively removed (or displaced) from such association (e.g., protein complex) by excess amounts of either specific binding partner. Such competition assays (or displacement assays) are very well known in the art.

The disclosure also provides methods for identifying agents useful for effecting muscle tone or mass. The disclosure provides endurance gene signatures (see, e.g., Table 2 and Table 4) comprising genes that are modulated in the presence of AICAR or GW1516, or a combination of AICAR and GW1516. Such gene signature are useful for identifying agents that provides an increase in muscle tone or mass and thereby can modulate physical endurance. A GW-AI endurance gene signature refers to a set of genes described in Table 4 or a subset thereof. A GW-TR endurance gene signature refers to a set of genes described in Table 2 or a subset thereof.

Figures 6, 6E:
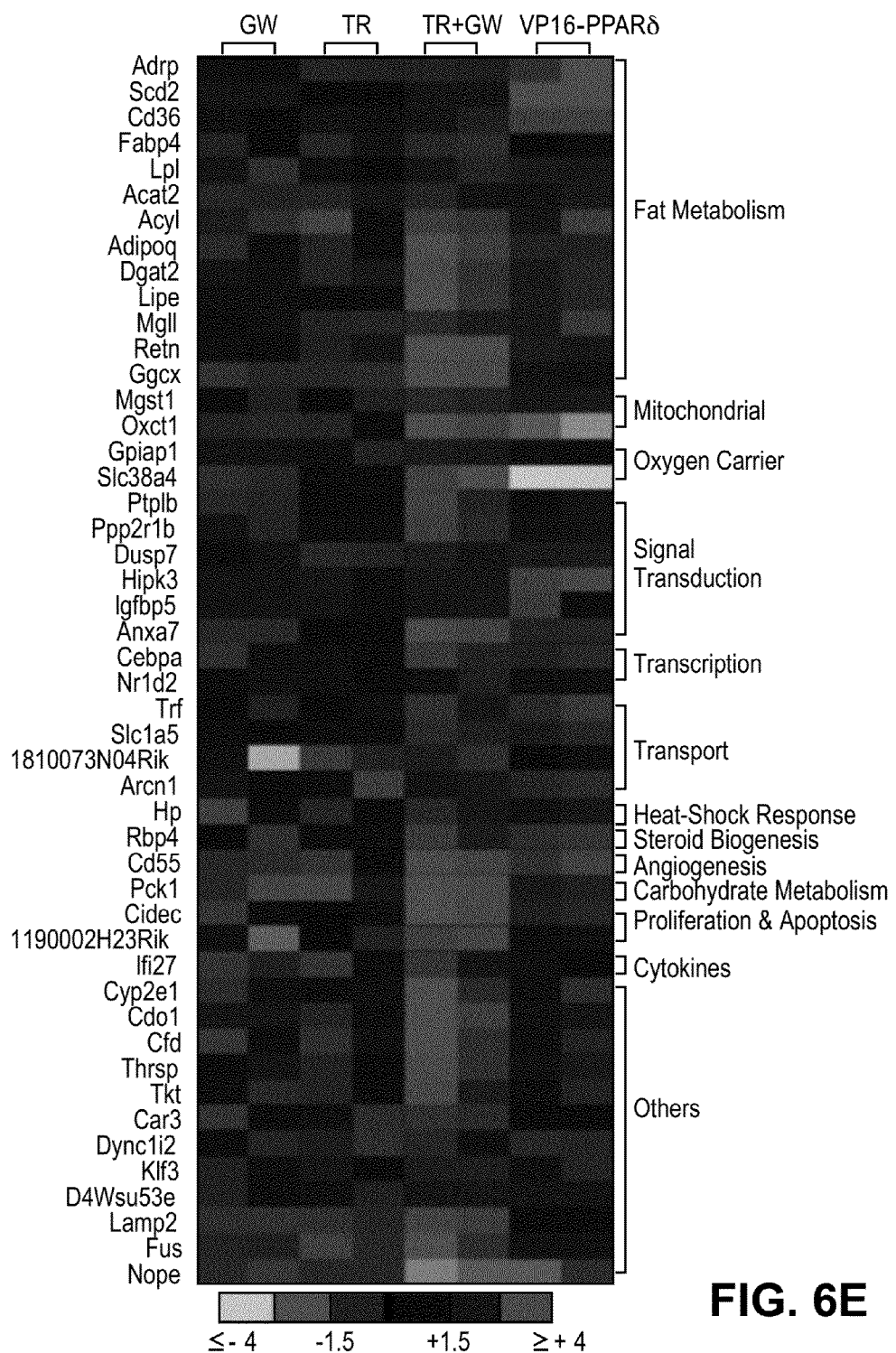
FIG. 6 shows a Venn diagram comparing GW, Tr and Tr+GW target genes identified in microarray analysis of quadriceps. Also shown are a classification of target genes in Tr+GW mice and relative expression of 48 unique TR+GW target genes in GW, TR, TR+GW, and VP16-PPARdelta muscles. Data is an average of N=3 samples in each group. The selection criteria used a $p<0.05$ on Bonferroni's multiple comparison test and a fold change greater than 1.5.
Figure 8A:
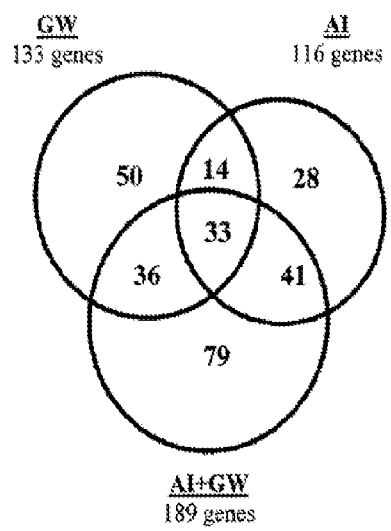
FIGS. 8A-C show the synergistic regulation of muscle gene expression by PPARδ and AMPK. (A) Venn diagram comparing GW, AI, and AI+GW target genes identified in microarray analysis of quadriceps. Data is an average of N=3 samples in each group. The selection criteria used a $p<0.05$ on Bonferroni's multiple comparison test and fold change greater than 1.5. (B) Comparison of Tr+GW and AI+GW dependent gene signatures identified in quadriceps. Data is an average of N=3 samples in each group. The selection criteria used is similar to one used in FIG. 8A. (C) Classification of 52 targets that were common to Tr+GW and AI+GW gene signatures.
Figure 8C:
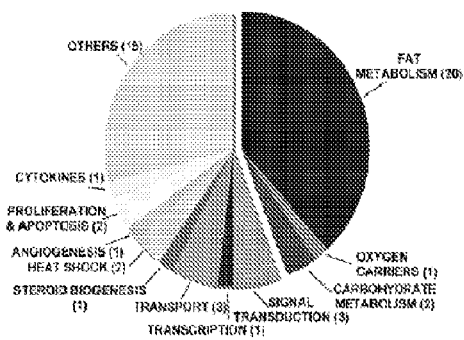

As depicted in FIGS. 6 and 8, an overlap of gene expression profile for each of the agonists is provided. An agent to be tested can be administered to a subject and the gene expression profile measure in a muscle sample (e.g., a biopsy) or other biological sample. Where the gene expression profile comprises a set of the endurance gene signatures (e.g., the overlapping 52 genes associated with GW1516 and AICAR administration, see Table 4) or a subset thereof such an agent can be identified as an agent or drug useful for treating or modifying muscle activity.

EXAMPLES

The following examples are provided to illustrate certain particular features and/or embodiments. These examples should not be construed to limit the invention to the particular features or embodiments described.

Example 1

Administration of PPARδ agonist does not enhance physical performance in non-exercised subjects. Wang et al. previously demonstrated that skeletal muscle-specific expression of a constitutively active form of PPARδ receptor resulted in transgenic mice with skeletal muscles that had an increased number of slow, oxidative (type I) muscle fibers and markedly increased running endurance (Wang et al., PLoC Biol., 2:e294, 2004). This Example demonstrates that administration of a PPARδ agonist (GW1516) to non-transgenic mice also results in the expression in skeletal muscle of some biomarkers of oxidative metabolism. However, in unexpected contrast to the results obtained by genetic activation of the PPARδ pathway, PPARδ activation by pharmacological treatment did not modify fiber-type composition of skeletal muscle, nor improve running endurance in non-transgenic, sedentary (also referred to as "non-exercised" or "untrained") mice. Male C57B/6J mice (8 wks old) were obtained from Jackson Laboratory and housed in the Salk Institute animal care facility. The animals were acclimated to their surroundings for one week prior to experimentation, and had access at all times to standard mouse chow and water ad libitum.

Mice were acclimated to moderate treadmill running (10 m/min for 15 min) every other day for 1 week. After acclimation, basal running endurance was determined by placing each mouse on a treadmill, gradually increasing the speed from 0 to 15 m/min, and maintaining 15 m/min until the mouse was exhausted. The time and distance run until exhaustion were recorded as the basal endurance values (Week 0).

Mice then were treated once per day for 4 weeks with vehicle or the PPARδ agonist, GW 1516 (5 mg/kg). Treatments were administered orally. During the treatment period, mice were housed in standard laboratory cages and received only the amount of physical activity that could be had by normal movements about such cage.

Animals were euthanized by carbon dioxide asphyxiation 72 hours after the final treatment. Gastrocnemius and quadriceps muscles were isolated, frozen and stored at −80° C. for future analysis. Total RNA was prepared from quadriceps muscle using TRIzoL™ reagent (Invitrogen, Carlsbad, Calif., USA) in conformance with manufacturer's instructions. Real time quantitative PCR (QPCR) was used to determine expression levels of uncoupling protein 3 (UCP3), muscle carnitine palmitoyl transferase I (mCPT I) and pyruvate dehydrogenase kinase 4 (PDK4) using primers known to those of ordinary skill in the art.

As shown in FIG. 1A, four weeks of GW1516 treatment induced the expression of UCP3, mCPT I, and PDK4, in quadriceps muscle of treated mice (compare V to GW). These changes in gene expression were detected as early as 4 days after treatment and with drug concentrations ranging from 2-5 mg/kg/day.

Moreover, in the gene expression studies, maximal effects of PPARδ activation were detected in pre-dominantly fast-twitch (quadricep and gastrocnemius) but not slow-twitch (soleus) muscles.

Using primary muscle cells cultured from wild type and PPARδ null mice (Chawla et al., Proc. Natl. Acad. ScL USA. 100(3): 1268-73, 2003; Man et al., J. Invest. Dermatol. 2007; Rando and Blau, J. Cell. Biol. 125(6): 1275-87, 1994), it was confirmed that the induction of oxidative genes by GW1516 is mediated via activation of PPARδ in skeletal muscles (FIGS. 1B-D). Moreover, this is similar to the expression changes found in the same gene set in muscles from mice expressing the constitutively active VP1β-PPARδ transgene (Wang et al., PLoC Biol, 2:e294, 2004) (FIG. 1A, see TG). Collectively, these results indicate that pharmacological activation of PPARδ can initiate an oxidative response in adult skeletal muscle.

Expression of biomarkers characteristic of an oxidative phenotype in skeletal muscle, typically, has been correlated with increased oxidative performance (e.g., increased running endurance) of such skeletal muscle. This correlation was observed, for instance, in the VP1β-PPARδ transgenic mouse (Wang et al., PLoC Biol., 2:e294, 2004). For this and other reasons, it was expected that GW1516 treatment similarly would increase running performance. Accordingly, to determine the functional effects of ligand, age and weight matched cohorts of treated and control mice were subjected to an endurance treadmill performance test before (week 0) and after (week 5) treatment. Following four weeks of treatment and housing in standard laboratory cages without additional exercise, the running endurance of GW1516-treated and control mice again was determined as described above. Remarkably, and despite expectations for improvement, GW1516-treated mice did not significantly differ from controls in either the time spent or distance run on the treadmill prior to exhaustion (FIG. 1E). Furthermore, long-term drug treatment of up to 5 months also did not change running endurance.

These results indicate that although in non-trained adult muscle pharmacological activation of PPARδ induces some transcriptional changes, it fails to alter either fiber type composition or endurance. In summary, pharmacologic activation of the PPARδ genetic program in adult C57B1/6J mice is insufficient to promote a measurable enhancement of treadmill endurance.

Example 2

Administration of PPARδ agonist remodels skeletal muscle in exercised-trained subjects. Fiber type proportions in skeletal muscle are believed to be determined by heredity and environmental factors, such as physical activity level (Simoneau and Bouchard, FASEB J., 9(11): 1091-1095, 1995; Larsson and Ansved, Muscle Nerve, 8(8):714-722, 1985). Endurance exercise training is known to remodel the skeletal muscle by increasing type I slow-twitch fibers, oxidative enzymes, and mitochondrial density, which progressively alter performance (Holloszy et al., J. Appl. Physiol. 56:831-8, 1984; Booth et al., Physiol Rev. 71:541-85, 1991; Schmitt et al., Physiol. Genomics. 15:148-57, 2003; Yoshioka et al., FASEB J. 17:1812-9, 2003; Mahoney et al., Phys. Med. Rehabil Clin. N. Am. 16:859-73, 2005; Mahoney et al., FASEB J. 19:1498-500, 2005; Siu et al., J. Appl Physiol. 97:277-85, 2004; Garnier et al., FASEB J. 19:43-52, 2005; Short et al., J Appl Physiol. 99:95-102, 2005; Timmons et al., FASEB J. 19: 750-60, 2005). This example demonstrates that PPARδ agonist treatment influences skeletal muscle on a molecular level.

To determine whether co-administration of GW1516 in the context of endurance exercise can enhance changes in fiber type composition and mitochondrial biogenesis, the effect of GW1516 treatment on muscle fiber-type composition was determined by meta-chromatic staining of cryo-sections of gastrocnemius as described by Wang et al (Phys Biol, 2:e294, 2004). Meta-chromatic staining was used, following a routine myofibrillar ATPase reaction, to demonstrate quantitative differences in phosphate deposition among different skeletal muscle fiber types and, thereby, differentiate skeletal muscle fiber types (Doriguzzi et al., Histochem., 79(3):289-294, 1983; Ogilvie and Feeback, Stain Technol, 65(5):231-241, 1990). In this assay, muscle fibers with high ATPase activity {e.g., type I (slow oxidative) muscle fibers) are darkly stained.

Figure 2B:
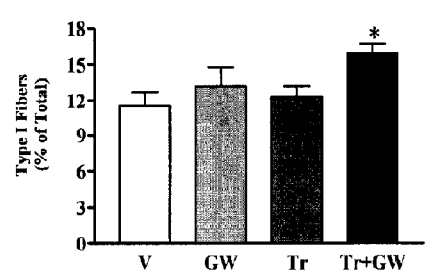

As shown in FIG. 2A, there was no significant difference in the proportion of type I (slow, oxidative) muscle fibers in the gastrocnemius muscles of vehicle- and GW1516-treated sedentary mice. In contrast, hind limb muscles of VP16-PPARδ transgenic mice exhibited an increased number of type I muscle fibers when assayed by monochromatic staining. In trained mice, GW1516 increased the proportion of type I fibers (by ~38%) compared to the vehicle-treated sedentary mice (FIGS. 2A and 2B). Therefore, administration of a PPARδ agonist (e.g., GW1516) alone to sedentary subjects does not significantly affect the number of type I (slow-twitch, oxidative) muscle fibers in hind limb muscles, but can increase the number of type I muscle fibers in hind limb muscles of trained subjects.

Figure 2C:
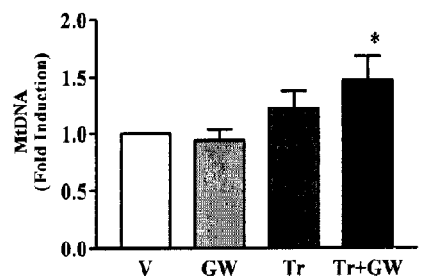

In addition to its effects on the fiber type, exercise training increased skeletal muscle mitochondrial biogenesis, which can be measured as a function of mitochondrial DNA expression levels using quantitative real time PCR (QPCR). Mitochondrial DNA expression levels were determined in muscles of V, GW, Tr, and GW+Tr subjects using quantitative real time PCR. As shown in FIG. 2C, similar to type I fiber changes, mitochondrial DNA expression was not changed by drug alone but was increased by approximately 50% with the combination of exercise and GW1516 treatment (FIG. 2C). Such an increase is known to contribute to enhanced endurance capacity (e.g., Holloszy, Med. Sci. Sports 7:155-64, 1975). Slow-twitch and fast-twitch muscle fiber types also can be distinguished by myosin isoform expression (Gauthier and Lowey, J. Cell Biol. 81:10-25, 1979; Fitzsimons and Hoh, Biochem. J. 193:229-33, 1981). Myosin isoform expression in skeletal muscle adapts to various conditions, such as changes in muscle mechanics, muscle innervation, or exercise paradigm (for review, see, e.g., Baldwin and Haddad, J. Appl. Physiol., 90(1):345-57, 2001; Baldwin and Haddad, Am. J. Phys. Med. Rehabil., 81(11 Suppl):S40-51, 2002; Parry, Exerc. Sport Sci Rev., 29(4): 175-179, 2001). The effect of GW1516 administration on myosin heavy chain (MHC) expression (MHC I, MHC IIa, MHC IIb) was determined by methods known to those of ordinary skill in the art. GW1516 treatment in sedentary mice increased the expression of MHC I (a marker of slow-twitch, oxidative muscle fibers) and decreased the expression of MHC IIb (a marker of fast-twitch, glycolytic muscle fibers) as compared to vehicle-treated, control mice. In comparison, GW1516 treatment did not alter the expression of MHC IIa (a marker of fast-twitch oxidative/glycolytic muscle fibers) in sedentary mice. Therefore, at least at the transcriptional level, the PPARδ agonist was capable of inducing some proteins characteristic of a slow-twitch muscle fiber phenotype.

Expression of constitutively active PPARδ in the skeletal muscles of VP1β-PPARδ transgenic mice resulted in a "long-distance running phenotype" with "profound and coordinated increases in oxidative enzymes, mitochondrial biogenesis and production of specialized type I fiber contractile proteins—the three hallmarks of muscle fiber type switching" (Wang at al., PLoC Biol., 2:e294, 2004). In contrast, pharmacological activation of PPARδ in normal subjects only partially recapitulated VP1β-PPARδ transgenesis by regulating some metabolic genes. Markedly, administration of a PPARδ agonist to sedentary subjects did not lead to a change in fiber type specification (as measured by monochromatic staining) or enhance exercise endurance. Transgenic over-expression of activated PPARδ at birth pre-programs the nascent myofibers to trans-differentiate into slow-twitch fibers, thus imparting a high basal endurance capacity to adult transgenic mice. In contrast, since fiber type specification is completed prior to exposure of adults to PPARδ agonist, the potential plasticity of muscle to drug treatment alone is virtually non-existent.

This example illustrates that the genetic or pharmacologic activation of the PPARδ regulatory program in skeletal muscles of adult, sedentary subjects does not have the same outcome. The ability to genetically manipulate skeletal muscle specification by activation of the PPARδ receptor in a transgenic mouse from early development in the absence of exercise is not necessarily predictive of the result of pharmacologically activating the PPARδ program in the sedentary, normal adult. The cellular "template" for PPARδ effects on skeletal muscle is very different in a normal subject as compared to a genetically engineered transgenic subject. For example, in a normal adult, muscle fiber specification of individual muscle groups is already determined and the connections between muscle fibers and spinal motor neurons are established prior to pharmacological activation of the PPARδ-regulated program. In the transgenic mouse, the constitutively active PPARδ transgene is active all the while muscle fiber specification is being determined and connections between muscle fibers and motor neurons are being made. In addition, the effects of activation of endogenous PPARδ receptor by a single daily dose of a PPARδ agonist, which is expect to have a transient peak exposure followed by clearance, likely are much different from the effects of the constitutive activation of a VP1β-PPARδ transgene.

Example 3

The combination of PPARδ agonist treatment and exercise training significantly affected fatty acid metabolism and markers of fatty acid oxidation. In addition to affecting the contractile apparatus of skeletal muscle, exercise training also increases skeletal muscle mitochondrial density (e.g., Freyssenet et al., Arch. Physiol. Biochem., 104(2): 129-141, 1996). This Example illustrates that PPARδ agonist treatment (e.g., GW1516) in exercise-trained subjects affected fatty acid metabolism in exercised muscle. The effects of GW1516 treatment and exercise, alone or in combination, on components of the oxidative metabolism of fatty acids were determined by measuring gene expression levels of selective biomarkers for fatty acid β-oxidation (FAO). Male C57B/6J mice (8-10 wks old) were randomly divided into four groups (nine per group): (i) vehicle-treated and sedentary (V), (ii) GW1516-treated and sedentary (GW), (iii) vehicle-treated and exercise trained (Tr) and (iv) GW1516-treated and exercise trained (GW+Tr). Mice in all groups were acclimated to moderate treadmill running and basal running endurance was determined as described in Example 1. Thereafter, mice in the exercise-trained groups received four weeks (5 days/week) of exercise training on a treadmill inclined at 5 degrees. Intensity and time of training were gradually increased. At the end of four weeks, all exercise-trained mice were running for 50 min/day at 18 m/min. Vehicle or GW1516 was administered to the respective exercise-treated or sedentary groups as described in Example 1. Unless otherwise noted, V, GW, Tr and GW+Tr subjects described in this and the examples below were similarly treated. At the end of the drug treatment and/or training protocol (Week 5) 6 mice per group were subjected to the running test. These interventions do not affect body weight and food intake in mice. RNA was prepared real time quantitative PCR performed as described in Example 1.

Confirming the results obtained in Example 1, UCP3, mCPT I, and PDK4 were upregulated by GW1516 but showed no further induction with exercise (see FIGS. 1A and 3A). Unexpectedly, a second set of genes were identified that showed no response to exercise or GW1516 alone but were robustly induced by the combination. This intriguing response profile includes a series of genes involved in the regulation of fatty acid storage (such as steroyl-CoA-desaturase (SCD1), fatty acyl coenzyme A synthase (FAS) and serum response element binding protein Ic (SREBPIc)) and fatty acid uptake [such as the fatty acid transporter (FAT/CD36) and lipoprotein lipase (LPL)] adding a new set of target genes to exercise and drug treated mice (FIGS. 3B, 3C and 6A-C).

In addition to gene expression, protein expression was determined for selective oxidative biomarkers including myoglobin, UCP3, cytochrome c (CYCS) and SCD1, using Western blotting. Protein homogenates were prepared from quadriceps muscle, separated by SDS polyacrylamide gel electrophoresis, transferred to blotting membrane and probed with antibodies specific for myoglobin (Dako), UCP3 (Affinity Bioreagents), cytochrome c (Santacruz) SCD1 (Santacruz), and, as a loading control, tubulin (Sigma). A robust up regulation of myoglobin, UCP3, cytochrome c, and SCD1 protein expression was observed with combined exercise and GW1516 treatment in comparison to treatment with the PPARδ agonist or exercise alone (FIG. 3D).

Figure 4:
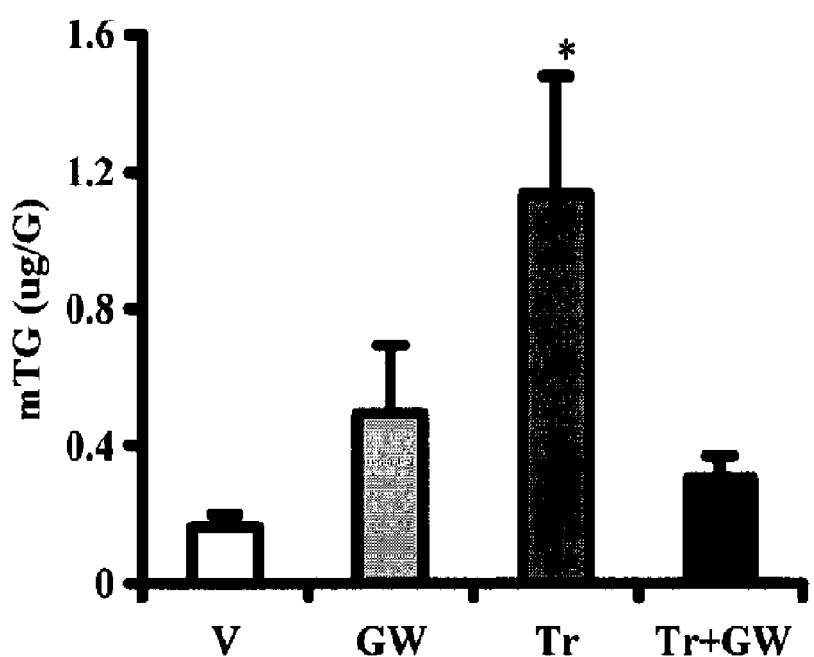
FIG. 4 shows a graph of muscle triglyceride levels in gastrocnemius muscle of V, GW, Tr and Tr+GW mice. Data is presented as mean±SEM of N=9 mice, each analyzed in triplicate. * represents statistical significance between V and group(s) indicated by asterisk (*$p<0.05$, One Way ANOVA; post hoc: Dunnett's Multiple Comparison Test).

Altered triglycerides can be used to access changes in muscle oxidative capacity. Muscle triglyceride (mTG) content was measured as previously described (Wang et al., PLoC Biol, 2:e294, 2004) using a kit from Thermo Electron Corporation. As shown in FIG. 4, mTG content was comparable between vehicle and GW1516-treated sedentary mice and was substantially increased in muscle of mice receiving only exercise training. In contrast, dramatic increase in triglycerides in exercised muscle was completely reversed in GW1516-treated exercise trained mice, indicating increased fat utilization (FIG. 4). Gene and/or protein expression that is induced by a combination of exercise and drug treatment (e.g., PPARδ agonist administration) but not by either input alone is believed to be a new discovery. This type of response can be used to further characterize the intersection of pharmacologic and physiologic genetic networks. For example, one or more genes and/or proteins uniquely regulated by one or more drugs {e.g., PPARδ agonists) and exercise can be used as markers, for instance, of illicitly boosting performance in professional and/or amateur athletes.

Example 4

Administration of PPARδ agonist enhances the physical performance of exercise-trained subjects. As described in Example 1, although GW1516 treatment induces widespread genomic changes associated with oxidative metabolism, nonetheless alone it failed to increase running endurance. This finding was unexpected because it was known that constitutive activation of the PPARδ gene network (in the VP1β-PPARδ transgenic mouse) lead to a distance-running phenotype (familiarly, a "marathon mouse"). On the other hand, as surprisingly shown in Example 3, PPARδ agonist (e.g., GW1516) treatment in conjunction with exercise produced an enriched remodeling program that included a series of transcriptional and post-translational adaptations in the skeletal muscle. This indicates that exercise training serves as a trigger to unmask a set of PPARδ target genes. This Example provides methods used to demonstrate that administration of a PPARδ agonist (e.g., GW1516) surprisingly improves physical performance in exercised (trained) subjects.

Male C57B/6J mice (8-10 wks old) were randomly divided into four groups (nine per group): (i) vehicle-treated and sedentary (V), (ii) GW1516-treated and sedentary (GW), (iii) vehicle-treated and exercise trained (Tr) and (iv) GW1516-treated and exercise trained (GW+Tr), acclimated to moderate treadmill running as described in Example 1, and exercise-trained as described in Example 3. At the end of the drug treatment and/or training protocol (Week 5) 6 mice per group were subjected to the running test.

At the end of the drug treatment and/or training protocol (Week 5), running endurance of six mice per group was determined in the same manner as was basal running endurance. No follow-up endurance tests were performed on three mice in each group to confirm that changes observed in the skeletal muscle were not due to the acute run, but were related to the exercise training.

Figure 5A:
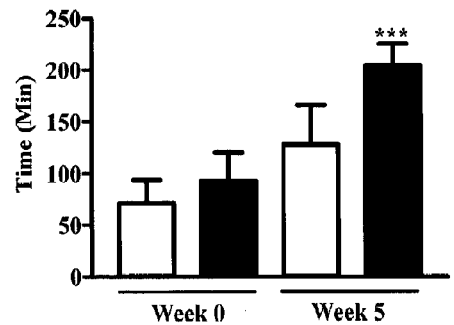
FIGS. 5A-C are bar graphs showing the effects of GW1516 treatment on running endurance in exercise-trained mice. Bar graphs of the (A) time and (B) distance that vehicle-(V; open bars) and GW1516-treated (GW; black bars) mice ran on a treadmill before (Week 0) and after (Week 5) exercise training. Data is represented as mean±SD of N=6 mice. *** represents statistically significant difference between V and GW groups ($p<0.001$; One Way ANOVA; post hoc: Tukey's Multiple Comparison Test). (C) is a bar graph showing epididymal white adipose to body weight ratio in V, GW, Tr and Tr+GW mice. Data is presented as mean±SEM of N=9 mice, each analyzed in triplicate. * represents statistical significance between V and group(s) indicated by asterisk (*$p<0.05$, One Way ANOVA; post hoc: Dunnett's Multiple Comparison Test).
Figure 5B:
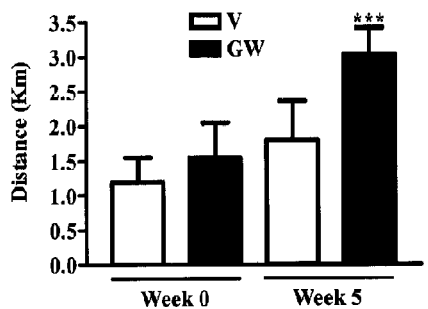
Figure 5C:
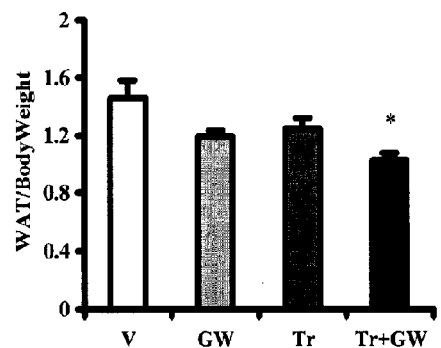
Figure 5D:
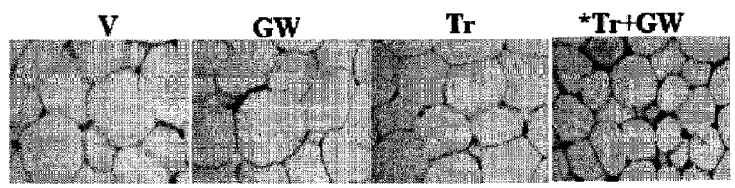
FIG. 5D shows digital images of H&E-stained cross-sections of epididymal white adipose from V, GW, Tr and Tr+GW mice. Similar results were obtained from N=3 mice. * represents statistical significance between V and group(s) indicated by asterisk (*$p<0.05$, One Way ANOVA; post hoc: Dunnett's Multiple Comparison Test).

As shown in FIGS. 5A and 5B, the same dose and duration of GW1516 treatment that failed to alter running endurance in sedentary mice, when paired with 4 weeks of exercise training, increases running time by 68% and running distance by 70% over vehicle-treated trained mice (FIGS. 5A and 5B, compare Week 5). Comparison of running time and distance before (week 0) and after (week 5) exercise and drug treatment revealed a 100% increment in endurance capacity for individual mice, underscoring the robustness of the combination paradigm (FIGS. 5 A and 5B). In contrast, the same exercise protocol without concurrent GW1516 treatment did not significantly increase running endurance in C57B1/6J mice. Hematoxylin and eosin (H&E) staining of white adipose tissue paraffin sections was performed as previously described (Wang et al., PLoS Biol., 2:e294, 2004; Wang et al., Cell, 113:159-70, 2003). As shown in FIG. 5C, GW1516 treatment in combination with exercise produced a significant (32%) reduction in the epididymal fat to body weight ratio, which was further evident in the decreased cross-sectional area of the adipocytes in the same group (FIG. 5D). Therefore, the combined effects of GW1516 and exercise are not restricted to muscle.

Using the methods described in Example 2, it was also demonstrated that the combination of GW1516 treatment and exercise training significantly increased the number of type I muscle fibers in exercised muscle. However, combining GW1516 treatment with exercise did not induce additional changes in MHC I and MHC IIb expression. Therefore, although orally administered PPARδ agonist (GW1516) alone is capable of inducing the expression of at least some of the contractile proteins in the PPARδ-regulated gene network (see Example 5) the transcriptional effect observed was not sufficient to induce a post-transcriptional change in fiber-type composition as was observed by meta-chromatic staining in GW1516-treated, exercised mice.

This Example illustrates that PPARδ agonist (e.g., GW1516) treatment unexpectedly augments the performance of aerobic exercise (e.g., running distance and endurance) in an exercised subject. Endurance exercise is known to channel extra-muscular fat to muscle triglyceride stores by inducing adipose tissue lipolysis to meet increased oxidative demands (Despres et al., Metabolism, 33:235-9, 1984; Mauriege et al., Am. J. Physiol, 273:E497-506, 1997; Mader et al., Int. J. Sports Med., 22:344-9, 2001; Schmitt et al., Physiol. Genomics, 15:148-57, 2003; Schrauwen-Hinderling et al., J. Clin. Endocrinol. Metab., 88:1610-6, 2003). In addition, the induction of FAO components and selective up-regulation of fatty acid storage and up-take components in GW1516-treated, exercised mice described in Example 3 indicate enhanced mobilization of fat as fuel in skeletal muscle.

Therefore, combined exercise and GW1516 treatment dramatically increases muscle oxidative capacity in subjects, for example by increasing local fatty acid synthesis and/or mobilizing fatty acid stores from adipose tissue.

This is the first demonstration of how an orally active PPARδ agonist and exercise can co-operatively re-program the muscle genome and raise endurance limits.

Example 5

The combination of PPARδ agonist treatment and exercise training produced a unique gene expression signature. A comprehensive study of the skeletal muscle transcriptional program in V, GW, Tr and Tr+GW mice was conducted using microarray analysis. Affymetrix™ high-density oligonucleotide array mouse genome 430A 2.0 chips were used.

Preparation of in vitro transcription products, oligonucleotide array hybridization, and scanning were performed in conformance with Affymetrix™-provided protocols. To minimize discrepancies due to variables, the raw expression data were scaled by using Affymetrix™ MICROARRAY SUITE™ 5.0 software, and pairwise comparisons were performed. The trimmed mean signal of all probe sets was adjusted to a user-specified target signal value (200) for each array for global scaling. No specific exclusion criteria were applied. Additional analyses were performed using the freeware program BULLFROG 7 (available on the internet Barlow-LockhartBrainMapNIMHGrant.org) and the Java-based statistical tool VAMPIRE (Hsiao et al., Bioinformatics, 20:3108-3127, 2004).

Genome-wide analysis of the quadriceps muscle revealed that GW1516 treatment, exercise, and the combination regulated 96, 113 and 130 genes, respectively (FIG. 6). Approximately 50% of the target genes regulated by GW1516 or exercise alone were the same, demonstrating that PPARδ activation of the gene network partially mimics exercise effects on the same network.

The 130 genes regulated by the combination of GW1516 treatment and exercise training and a classification of each such gene are shown in Table 1. The 130 regulated genes included 30 fat metabolism genes, 5 oxygen carriers, 5 mitochondrial genes, 3 carbohydrate metabolism genes, 15 signal transduction genes, 16 transcription genes, 10 transport genes, 3 steroid biogenesis genes, 5 heat shock genes, 2 angiogenesis genes, 5 proliferation and apoptosis genes, 2 cytokines, and 29 others. The majority of the genes in the exercise-trained/GW1516-treated (GW+Tr) gene signature shown in Table 1 were induced (109/130). The 109 upregulated genes are shown in non-bold font in Table 1 (final column >1). Down-regulated genes are shown in bold italics in Table 1 (final column <1).

TABLE 1

Genes regulated by GW1516 treatment and exercise training

| FEATURE | LOCUS | DESCRIPTION | GW + Tr |
|---|---|---|---|
| ANGIOGENESIS | | | |
| 1417130_s_at | Angptl4 | angiopoietin-like 4 | 5.495 |
| *1418762_at* | *Cd55* | *CD55 antigen* | *0.56* |
| CARBOHYDRATE METABOLISM | | | |
| 1449088_at | Fbp2 | fructose bisphosphatase 2 | 2.808 |
| 1423439_at | Pck1 | phosphoenolpyruvate carboxykinase 1, cytosolic | 3.518 |
| 1434499_a_at | Ldhb | lactate dehydrogenase B | 2.541 |
| PROLIFERATION & APOPTOSIS | | | |
| 1425621_at | Trim35 | tripartite motif-containing 35 | 1.856 |
| *1418003_at* | *1190002H23Rik* | *RIKEN cDNA 1190002H23 gene* | *0.543* |
| 1448272_at | Btg2 | B-cell translocation gene 2, anti-proliferative | 1.601 |
| 1452260_at | Cidec | cell death-inducing DFFA-like effector c | 4.771 |
| 1417956_at | Cidea | cell death-inducing DNA fragmentation factor, alpha subunit-like effector A | 49.625 |
| CYTOKINES | | | |
| 1426278_at | Ifi27 | interferon, alpha-inducible protein 27 | 1.714 |
| 1421239_at | Il6st | interleukin 6 signal transducer | 1.972 |
| FAT METABOLISM | | | |
| 1448318_at | Adfp | adipose differentiation related protein | 2.009 |
| 1424729_at | BC054059 | cDNA sequence BC054059 | 5.08 |
| 1424937_at | 2310076L09Rik | RIKEN cDNA 2310076L09 gene | 1.868 |
| 1450010_at | Hsd17b12 | hydroxysteroid (17-beta) dehydrogenase 12 | 2.376 |
| 1415965_at | Scd1 | stearoyl-Coenzyme A desaturase 1 | 6.494 |
| 1415822_at | Scd2 | stearoyl-Coenzyme A desaturase 2 | 1.849 |
| 1423828_at | Fasn | fatty acid synthase | 6.323 |
| 1455061_a_at | Acaa2 | acetyl-Coenzyme A acyltransferase 2 (mitochondrial 3-oxoacyl-Coenzyme A thiolase) | 1.926 |
| 1448987_at | Acadl | acetyl-Coenzyme A dehydrogenase, long-chain | 2.549 |
| 1422651_at | Adipoq | adiponectin, C1Q and collagen domain containing | 3.082 |
| 1422820_at | Lipe | lipase, hormone sensitive | 3.032 |
| 1449964_a_at | Mlycd | malonyl-CoA decarboxylase | 1.781 |
| 1426785_s_at | Mgl1 | monoglyceride lipase | 1.907 |
| 1420658_at | Ucp3 | uncoupling protein 3 (mitochondrial, proton carrier) | 2.943 |
| 1425326_at | Acly | ATP citrate lyase | 2.606 |
| 1460409_at | Cpt1a | carnitine palmitoyltransferase 1a, liver | 2.753 |
| 1422677_at | Dgat2 | diacylglycerol O-acyltransferase 2 | 2.784 |
| *1456702_x_at* | *Ggcx* | *gamma-glutamyl carboxylase* | *0.575* |
| 1425834_a_at | Gpam | glycerol-3-phosphate, acyltransferase mitochondrial | 2.207 |
| 1417273_at | Pdk4 | pyruvate dehydrogenase kinase, isoenzyme 4 | 2.27 |
| 1449182_at | Retn | resistin | 4.114 |

TABLE 1-continued

Genes regulated by GW1516 treatment and exercise training

| FEATURE | LOCUS | DESCRIPTION | GW + Tr |
|---|---|---|---|
| 1435630_s_at | Acat2 | acetyl-Coenzyme A acetyltransferase 2 | 1.625 |
| 1425829_a_at | Abcb1a | ATP-binding cassette, sub-family B (MDR/TAP), member 1A | 10.322 |
| 1423166_at | Cd36 | CD36 antigen | 1.584 |
| 1422811_at | Slc27a1 | solute carrier family 27 (fatty acid transporter), member 1 | 3.58 |
| 1416023_at | Fabp3 | fatty acid binding protein 3, muscle and heart | 1.833 |
| 1424155_at | Fabp4 | fatty acid binding protein 4, adipocyte | 2.189 |
| 1431056_a_at | Lpl | lipoprotein lipase | 1.659 |
| 1422432_at | Dbi | diazepam binding inhibitor | 1.936 |
| 1422811_at | Slc27a1 | solute carrier family 27 (fatty acid transporter), 1 | 3.58 |
| | | HEAT SHOCK RESPONSE | |
| 1448881_at | Hp | haptoglobin | 1.679 |
| 1427126_at | Hspa1b | heat shock protein 1B | 8.845 |
| 1438902_a_at | Hsp90aa1 | heat shock protein 90 kDa alpha (cytosolic), class A member 1 | 1.513 |
| 1431274_a_at | Hspa9a | heat shock protein 9A | 1.61 |
| 1416755_at | Dnajb1 | DnaJ (Hsp40) homolog, subfamily B, member 1 | 3.59 |
| | | MISCELLANEOUS | |
| 1460256_at | Car3 | carbonic anhydrase 3 | 2.339 |
| 1415841_at | Dync1i2 | dynein cytoplasmic 1 intermediate chain 2 | 1.705 |
| 1432344_a_at | Aplp2 | amyloid beta (A4) precursor-like protein 2 | 1.937 |
| 1416429_a_at | Cat | catalase | 1.82 |
| 1418306_at | Crybb1 | crystallin, beta B1 | 2.457 |
| 1448842_at | Cdo1 | cysteine dioxygenase 1, cytosolic | 3.266 |
| *1434503_s_at* | *Lamp2* | *lysosomal membrane glycoprotein 2* | *0.608* |
| *1416473_a_at* | *Nope* | *neighbor of Punc E11* | *0.452* |
| 1453527_a_at | Neurl | neuralized-like homolog (Drosophila) | 1.941 |
| 1451603_at | Rtbdn | retbindin | 2.32 |
| 1453724_a_at | Serpinf1 | serine (or cysteine) peptidase inhibitor, clade F, member 1 | 7.765 |
| *1448680_at* | *Serpina1a* | *serine (or cysteine) proteinase inhibitor, clade A, member 1a* | *0.396* |
| 1427285_s_at | Surf4 | surfeit gene 4 | 2.091 |
| 1424737_at | Thrsp | thyroid hormone responsive SPOT14 homolog (Rattus) | 2.685 |
| 1431609_a_at | Acp5 | add phosphatase 5, tartrate resistant | 3.91 |
| 1448538_a_at | D4Wsu53e | DNA segment, Chr 4, Wayne State University 53, expressed | 1.586 |
| *1452406_x_at* | | *erythroid differentiation regulator 1* | *0.619* |
| *1451286_s_at* | *Fus* | *fusion, derived from t(12;16) malignant liposarcoma (human)* | *0.605* |
| 1425552_at | Hip1r | huntingtin interacting protein 1 related | 1.75 |
| *1428091_at* | *Klhl7* | *kelch-like 7 (Drosophila)* | |
| 1429360_at | Klf3 | Kruppel-like factor 3 (basic) | 1.901 |
| 1449413_at | Mpv17l | Mpv17 transgene, kidney disease mutant-like | 1.988 |
| 1451667_at | C530043G21Rik | RIKEN cDNA C530043G21 gene | 1.5 |
| 1425865_a_at | Lig3 | ligase III, DNA, ATP-dependent | 2.693 |
| 1415994_at | Cyp2e1 | cytochrome P450, family 2, subfamily e, polypeptide 1 | 2.941 |
| 1417867_at | Cfd | complement factor D (adipsin) | 2.828 |
| 1451015_at | Tkt | transketolase | 2.256 |
| 1432344_a_at | Aplp2 | amyloid beta (A4) precursor-like protein 2 | 1.937 |
| 1419487_at | Mybph | Myosin binding protein H | 1.578 |
| | | MITOCHONDRIAL PROTEINS | |
| *1436750_a_at* | *Oxct1* | *3-oxoacid CoA transferase 1* | *0.574* |
| 1415897_a_at | Mgst1 | microsomal glutathione S-transferase 1 | 1.916 |
| *1434970_a_at* | *Mrpl15* | *mitochondrial ribosomal protein L15* | *0.61* |
| 1423109_s_at | Slc25a20 | solute carrier family 25 (mitochondrial carnitine/acylcarnitine translocase), member 20 | 1.865 |
| *1416014_at* | *Abce1* | *ATP-binding cassette, sub-family E (OABP), member 1* | *0.556* |
| | | OXYGEN CARRIERS | |
| 1448348_at | Gpiap1 | GPI-anchored membrane protein 1 | 1.83 |
| 1451203_at | Mb | myoglobin | 1.578 |
| *1428111_at* | *Slc38a4* | *solute carrier family 38, member 4* | *0.579* |
| 1428361_x_at | Hba-a1 | hemoglobin alpha, adult chain 1 | 1.632 |
| 1417184_s_at | Hbb-b2|Hbb-y | hemoglobin, beta adult minor chain|hemoglobin Y, beta-like embryonic chain | 1.626 |
| | | SIGNAL TRANSDUCTION | |
| *1416137_at* | *Anxa7* | *annexin A7* | *0.544* |
| 1455918_at | Adrb3 | adrenergic receptor, beta 3 | 3.83 |
| *1417163_at* | *Dusp10* | *dual specificity phosphtase 10* | *0.579* |
| 1452097_a_at | Dusp7 | dual specificity phosphatase 7 | 1.661 |
| 1419191_at | Hipk3 | homeodomain interacting protein kinase 3 | 1.694 |
| 1448152_at | Igf2 | insulin-like growth factor 2 | 1.635 |
| 1422313_a_at | Igfbp5 | insulin-like growth factor binding protein 5 | 1.772 |

TABLE 1-continued

Genes regulated by GW1516 treatment and exercise training

| FEATURE | LOCUS | DESCRIPTION | GW + Tr |
|---|---|---|---|
| 1428265_at | Ppp2r1b | protein phosphatase 2 (formerly 2A), regulatory subunit A (PR 65), beta isoform | 2.509 |
| *1438562_a_at* | *Ptpn2* | *Protein tyrosine phosphatase, non-receptor type 2* | *0.432* |
| 1449342_at | Ptplb | protein tyrosine phosphatase-like (proline instead of catalytic arginine), member b | 2.38 |
| 1422119_at | Rab5b | RAB5B, member RAS oncogene family | 1.603 |
| *1437016_x_at* | *Rap2c* | *RAP2C, member of RAS oncogene family* | *0.601* |
| 1425444_a_at | Tgfbr2 | transforming growth factor, beta receptor II | 2.13 |
| 1431164_at | Rragd | Ras-related GTP binding D | 2.101 |
| 1420816_at | Ywhag | 3-monooxygenase/tryptophan 5-monooxygenase activation protein, gamma polypeptide | 1.87 |
| | | STEROID BIOGENESIS | |
| 1418601_at | Aldh1a7 | aldehyde dehydrogenase family 1, subfamily A7 | 3.862 |
| 1426225_at | Rbp4 | retinol binding protein 4, plasma | 2.065 |
| *1455913_x_at* | *Ttr* | *transthyretin* | *0.026* |
| | | TRANSCRIPTION | |
| 1417794_at | Zfp261 | zinc finger protein 261 | 1.847 |
| 1424731_at | Nle1 | notchless homolog 1 (*Drosophila*) | 1.831 |
| 1454791_a_at | Rbbp4 | retinoblastoma binding protein 4 | 2.865 |
| 1460281_at | Asb15 | ankyrin repeat and SOCS box-containing protein 15 | 1.78 |
| 1449363_at | Atf3 | activating transcription factor 3 | 1.802 |
| 1418982_at | Cebpa | CCAAT/enhancer binding protein (C/EBP), alpha | 2.168 |
| 1417065_at | Egr1 | early growth response 1 | 2.577 |
| *1434831_a_at* | *Foxo3a* | *forkhead box O3a* | *0.634* |
| 1415899_at | Junb | Jun-B oncogene | 1.792 |
| 1421554_at | Lmx1a | LIM homeobox transcription factor 1 alpha | 4.106 |
| 1416959_at | Nr1d2 | nuclear receptor subfamily 1, group D, member 2(Reverb-b) | 1.794 |
| 1450749_a_at | Nr4a2 | nuclear receptor subfamily 4, group A, member 2 (NURR1) | 1.776 |
| 1460215_at | Rpol-4 | RNA polymerase 1-4 | 2.498 |
| *1417719_at* | *Sap30* | *sin3 associated polypeptide* | *0.551* |
| 1420892_at | Wnt7b | wingless-related MMTV integration site 7B | 4.449 |
| 1423100_at | Fos | FBJ osteosarcoma oncogene | 3.9 |
| | | TRANSPORT PROTEINS | |
| *1427222_a_at* | *Svp2* | *seminal vesicle protein 2* | *0.014* |
| *1456124_x_at* | *Svs5* | *seminal vesicle secretion 5* | *0.095* |
| 1425546_a_at | Trf | transferrin | 1.907 |
| 1423743_at | Arcn1 | archain 1 | 1.617 |
| 1451771_at | Tpcn1 | two pore channel 1 | 2.842 |
| 1416629_at | Slc1a5 | solute carrier family 1 (neutral amino acid transporter), member 5 | 1.939 |
| 1420295_x_at | Clcn5 | chloride channel 5 | 2.333 |
| 1417839_at | Cldn5 | claudin 5 | 1.545 |
| *1425260_at* | *Alb1* | *albumin 1* | *0.245* |
| 1434617_x_at | 1810073N04Rik | RIKEN cDNA 1810073N04 gene | 2.326 |

Data is average of N=3 samples in each group (p<0.05).

Surprisingly, the combination of GW1516 treatment and exercise established a unique gene expression pattern ("a GW+TR profile") that was neither an amalgamation nor a complete overlap of the two interventions (FIG. 6). This unique signature included 48 target genes (Table 2) not regulated by GW1516 and exercise alone and excluded 74 genes regulated by GW1516 or exercise alone (some of which are shown in Table 3). This signature for the combination of GW1516 treatment and exercise (Table 2) was highly enriched in genes encoding regulatory enzymes for energy homeostasis, angiogenesis, oxygen transport, signal transduction, transcription and substrate transport, which are processes that are involved in endurance adaptation. Particularly, a predominance of genes involved in oxidative metabolism, is selectively up-regulated by combined exercise and drug treatment (see unbolded genes in Tables 1 and 2). In addition, several stress-related genes activated by either intervention, including heat shock proteins, metallothioneins and other stress biomarkers (Table 3) are not changed by the combination possibly reflecting a potential lessening of exercise-based damage.

TABLE 2

Gene targets unique to combined GW1516 treatment and exercise training.

| DESCRIPTION | LOCUS | GW + Tr |
|---|---|---|
| ANGIOGENESIS | | |
| *CD55 antigen* | *Cd55* | *0.56* |
| CARBOHYDRATE METABOLISM | | |
| phosphoenolpyruvate carboxykinase 1, cytosolic | Pck1 | 3.518 |
| CYTOKINES | | |
| interferon, alpha-inducible protein 27 | Ifi27 | 1.714 |
| FAT METABOLISM | | |
| adipose differentiation related protein | Adrp | 2.009 |
| stearoyl-Coenzyme A desaturase 2 | Scd2 | 1.849 |
| acetyl-Coenzyme A acetyltransferase 2 | Acat2 | 1.625 |
| ATP citrate lyase | Acly | 2.606 |
| adiponectin, C1Q and collagen domain containing | Adipoq | 3.082 |
| diacylglycerol O-acyltransferase 2 | Dgat2 | 2.784 |

TABLE 2-continued

Gene targets unique to combined GW1516 treatment and exercise training.

| DESCRIPTION | LOCUS | GW + Tr |
|---|---|---|
| *gamma-glutamyl carboxylase* | *Ggcx* | *0.575* |
| lipase, hormone sensitive | Lipe | 3.032 |
| monoglyceride lipase | Mgll | 1.907 |
| resistin | Retn | 4.114 |
| CD36 antigen | Cd36 | 1.584 |
| fatty acid binding protein 4, adipocyte | Fabp4 | 2.189 |
| lipoprotein lipase | Lpl | 1.659 |
| HEAT SHOCK RESPONSE | | |
| haptoglobin | Hp | 1.679 |
| MITOCHONDRIAL PROTEINS | | |
| *3-oxoacid CoA transferase 1* | *Oxct1* | *0.574* |
| microsomal glutathione S-transferase 1 | Mgst1 | 1.916 |
| OTHERS | | |
| carbonic anhydrase 3 | Car3 | 2.339 |
| cysteine dioxygenase 1, cytosolic | Cdo1 | 3.266 |
| DNA segment, Chr 4, Wayne State University 53, expressed | D4Wsu53e | 1.586 |
| dynein cytoplasmic 1 intermediate chain 2 | Dync1i2 | 1.705 |
|  | *Fus* | *0.605* |
| Kruppel-like factor 3 (basic) | Klf3 | 1.901 |
| *lysosomal membrane glycoprotein 2* | *Lamp2* | *0.608* |
| *neighbor of Punc E11* | *Nope* | *0.452* |
| thyroid hormone responsive SPOT14 homolog (*Rattus*) | Thrsp | 2.685 |
| cytochrome P450, family 2, subfamily e, polypeptide 1 | Cyp2e1 | 2.941 |
| complement factor D (adipsin) | Cfd | 2.828 |
| transketolase | Tkt | 2.256 |
| OXYGEN CARRIERS | | |
| GPI-anchored membrane protein 1 | Gpiap1 | 1.83 |
| *solute carrier family 38, member 4* | *Slc38a4* | *0.579* |
| PROLIFERATION & APOPTOSIS | | |
| *RIKEN cDNA 1190002H23 gene* | *1190002H23Rik* | *0.543* |
| cell death-inducing DFFA-like effector c | Cidec | 4.771 |
| SIGNAL TRANSDUCTION | | |
| *annexin A7* | *Anxa7* | *0.544* |
| dual specificity phosphatase 7 | Dusp7 | 1.661 |
| homeodomain interacting protein kinase 3 | Hipk3 | 1.694 |
| insulin-like growth factor binding protein 5 | Igfbp5 | 1.772 |
| protein phosphatase 2 (formerly 2A), regulatory subunit A (PR 65), beta isoform | Ppp2r1b | 2.509 |
| protein tyrosine phosphatase-like (proline instead of catalytic arginine), member b | Ptplb | 2.38 |
| STEROID BIOGENESIS | | |
| retinol binding protein 4, plasma | Rbp4 | 2.065 |
| TRANSCRIPTION | | |
| CCAAT/enhancer binding protein (C/EBP), alpha | Cebpa | 2.168 |
| nuclear receptor subfamily 1, group D, member 2(Reverb-b) | Nr1d2 | 1.794 |
| TRANSPORT | | |
| transferrin | Trf | 1.907 |
| archain 1 | Arcn1 | 1.617 |
| solute carrier family 1 (neutral amino acid transporter), member 5 | Slc1a5 | 1.939 |
| RIKEN cDNA 1810073N04 gene | 1810073N04Rik | 2.326 |

TABLE 3

Gene targets regulated by GW1516 treatment or exercise training alone.

| FEATURE | LOCUS | DESCRIPTION | GW | Tr | GW + Tr |
|---|---|---|---|---|---|
|  | Hspb1 | heat shock protein 1 | 1.815 | 1.965 | — |
| 1451284_at | Hspb7 | heat shock protein family, 7 (cardiovascular) | 3.414 | 1.753 | — |
| 1422943_a_at | Dnaja1 | DnaJ (Hsp40) homolog, subfamily A, 1 | — | 1.545 | — |
| 1421290_at | Hsp110 | heat shock protein 110 | — | 1.587 | — |
| 1416288_at | Serpinh1 | serine (or cysteine) peptidase inhibitor, H, 1 | — | 2.198 | — |
| 1423566_a_at | Dnaja4 | DnaJ (Hsp40) homolog, subfamily A, 4 | 1.756 | 1.545 | — |
| 1417872_at | Mt1 | metallothionein 1 | 2.364 | — | — |
| 1424596_s_at | Mt2 | metallothionein 2 | 2.151 | — | — |
| 1416157_at | Cryab | crystallin, alpha B | 1.561 | 1.52 | — |
| 1423139_at | Crygf | crystallin, gamma F | 1.801 | 3.56 | — |
| 1448830_at | Smad3 | MAD homolog 3 (*Drosophila*) | 1.841 | 1.886 | — |
| 1450637_a_at | Ankrd1 | ankyrin repeat domain 1 (cardiac muscle) | 4.235 | — | — |
| 1416029_at | Tnfrsf12a | TNF receptor superfamily, 12a | 1.759 | 1.782 | — |
| 1426464_at | Jun | Jun oncogene | — | 1.521 | — |

Data is average of N=3 samples in each group ($p<0.05$)

Thirty-two percent of the GW+Tr-regulated genes encode enzymes of metabolic pathways such as fatty acid biosynthesis/storage (e.g., FAS, SCD 1 & 2), uptake [e.g., FAT/CD36, fatty acid binding proteins (FABP) and LPL] and oxidation [e.g., adiponectin, hormone sensitive lipase (HSL), PDK4, UCP3]; and carbohydrate metabolism [e.g., fructose bisphosphate 2 (FBP2), phosphoenolpyruvate carboxykinase 1 (PEPCK1), lactate dehydrogenase B], which along with oxygen transporters and mitochondrial proteins form the largest class of genes directly linked to muscle performance (Ikeda et al., Biochem. Biophys. Res. Commun. 296:395-400, 2002; Achten and Jeukendrup, Nutrition. 20:716-27, 2004; Hittel et al., J. Appl. Physiol. 98: 168-79, 2005; Civitarese et al., Cell Metab. 4:75-87, 2006; Nadeau et al., FASEB J. 17:1812-9, 2006; Kiens, Physiol. Rev. 86:205-43, 2006; Yamauchi et al., Nat. Med. 8:1288-95, 2006). Unexpectedly, established PPARa target genes fatty acyl-CoA oxidase and medium chain acyl-CoA dehydrogenase (MCAD) were not represented in the signature. All but four of these metabolic genes were induced, which indicated a general increase in oxidative capacity of skeletal muscle in exercise-trained subjects that received GW1516 treatment.

Other genes regulated in quadriceps muscle by the combination of exercise and GW1516 treatment encoded proteins involved in pathways such as angiogenesis (e.g., angiopoietin-like 4 protein/also a known regulator of lipid metabolism), (e.g., adrenergic receptor β3, insulin-like growth factor, insulin-like growth factor binding protein 5), transcription (e.g., C/EBP α, Reverb β, NURR1) and substrate transport (e.g., transferrin, chloride channel 5) (Nagase et al., J. Clin. Invest. 97:2898-904, 1996; Singleton and Feldman, Neurobiol. Dis. 8:541-54, 2001; Adams, J. Appl. Physiol. 93:1159-67, 2002; Centrella et al., Gene. 342: 13-24, 2004; Lundby et al., Eur. J. Appl Physiol. 96: 363-9, 2005; Mahoney et al., FASEB J. 19: 1498-500, 2005; Mahoney et al., Phys. Med. Rehabil Clin. N. Am. 16: 859-73, 2005; Ramakrishnan et al., J. Biol. Chem. 280:8651-9, 2005). Without wishing to be bound to a particular theory, such other genes are likely involved, at least in part, in muscle remodeling and increased endurance observed in GW1516-treated, exercise-trained subjects.

Interestingly, comparative expression analysis of the 48 gene subset of the endurance signature (Table 2), but not of either intervention alone, revealed a striking similarity to 'untrained' VP16-PPARδ transgenic mice. This observation confirms the primary dependence of the 48 genes on PPARδ and indicates that exercise-generated signals may function to synergize PPARδ transcriptional activity to levels comparable to transgenic over-expression. Therefore, exercise cues along with PPARδ agonist may function to hyper-activate receptor transcriptional activity to re-program of adult muscle.

Genes and/or proteins uniquely affected (e.g., up-regulated or down-regulated or not substantially regulated) by exercise in the presence of one or more pharmaceutical agents (e.g., PPARδ agonists) can be used as markers, for instance, of "drug doping" in exercise-trained subjects (e.g., athletes). It is expected that the unique set of 48 genes regulated by GW+Tr, but not GW1516 treatment or exercise training alone, can be used to identify exercised subjects who have received a variety performance-enhancing drugs.

Example 6

PPARδ directly interacts with exercise-activated kinases, p44/42 MAPK and AMPK. Exercise training is known to activate kinases, such as p44/42 MAPK and AMPK, which regulate gene expression in skeletal muscle (Chen et al., Diabetes, 52:2205-12, 2003; Goodyear et al., Am. J. Physiol, 271:E403-8, 1996). AMPK affects skeletal muscle gene expression and oxidative metabolism (Chen et al., Diabetes. 52: 2205-12, 2003, Reznick et al., J. Physiol. 574: 33-9, 2006). The interaction between exercise-regulated kinases and PPARδ signaling is described in this Example. The levels of phospho-p44/42 MAPK and phospho-AMPK a subunit and total AMPK were determined in protein homogenates of quadriceps muscle by Western blot. Antibodies specific for phospho-p44/42 MAPK, phospho- and total-AMPK αl antibodies were obtained from Cell Signaling. The phospho-specific AMPK αl antibody recognizes the key activating threonine in the activation loop.

Active forms of both kinases (phospho-p44/42 MAPK and phospho-AMPK α subunit) were expressed at higher levels in the quadriceps muscles of exercised mice relative to the sedentary controls (FIG. 7A). Previous reports claim that PPARδ is not required for activation of AMPK by GW1516 in cultured cells (Kramer et al., Diabetes. 54(4): 1157-63, 2005 and Kramer et al., J. Biol. Chem. 282(27): 19313-2, 2007). In contrast, it was observed that GW1516 failed to activate p44/42 or AMPK in either sedentary or trained muscles, which indicated that PPARδ-regulated effects are downstream to the exercise-induced signals that activate these kinases. Furthermore, AMPK appears to be constitutively active in muscles of VP16-PPARδ transgenic mice in absence of exercise or drug (FIG. 7B). These results indicate that synergy is AMPK and PPARδ co-dependent.

If synergy is AMPK and PPARδ co-dependent, selective co-activation of AMPK and PPARδ would induce gene expression changes that mimic those triggered by combined exercise and PPARδ as well as VP16-PPARδ over-expression. To demonstrate this, transcriptional changes induced in skeletal muscle by combined exercise and GW1516 treatment (as described in Example 5) were compared to that of combined AMPK activator (the cell permeable AMP analog AICAR; 250 mg/kg/day, i.p.) and GW1516 (5 mg/kg/day, oral gavage) treatment for 6 days. Genome analysis was performed using the methods described in Example 5.

Figure 8B:
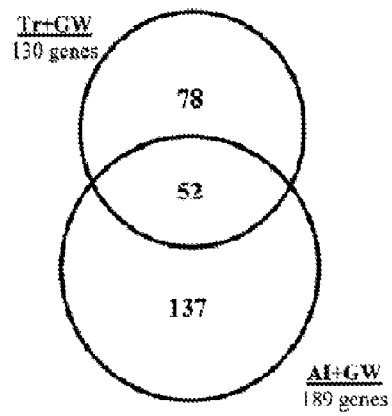

Simultaneous GW1516 and AICAR treatment for 6 days created a unique gene expression signature in the quadriceps of untrained C57B1/6J mice (FIG. 8A, which includes target genes associated with translation, protein processing, amino acid metabolism, fat metabolism, oxygen carriers, carbohydrate metabolism, signal transduction, transcription, transport, steroid biogenesis, heat shock response, angiogenesis, proliferation and apoptosis, cytokines, contractile proteins, stress, and others) that shares 40% of the genes with that of combined GW1516 treatment and exercise (FIG. 8B). Classification of the 52 genes common to the two signatures (combined PPARδ activation and exercise or PPARδ and AMPK co-activation) (listed in Table 4) revealed that the majority of the targets were linked to oxidative metabolism.

TABLE 4

Targets common to exercise-PPARδ and AMPK-PPARδ gene signatures.

| DESCRIPTION | LOCUS | Tr + GW | AI + GW |
|---|---|---|---|
| ANGIOGENESIS | | | |
| angiopoietin-like 4 | Angptl4 | 5.495 | 2.917 |
| APOPTOSIS | | | |
| cell death-inducing DFFA-like effector c | Cidec | 4.771 | 1.838 |
| cell death-inducing DNA fragmentation factor, alpha subunit-like effector A | Cidea | 49.625 | 1.842 |
| CARBOHYDRATE METABOLISM | | | |
| lactate dehydrogenase B | Ldhb | 2.541 | 1.917 |
| fructose bisphosphatase 2 | Fbp2 | 2.808 | 2.478 |
| FAT METABOLISM | | | |
| stearoyl-Coenzyme A desaturase 1 | Scd1 | 6.494 | 1.78 |
| fatty acid binding protein 3, muscle and heart | Fabp3 | 1.833 | 1.5 |
| pyruvate dehydrogenase kinase, isoenzyme 4 | Pdk4 | 2.27 | 2.486 |
| uncoupling protein 3 (mitochondrial, proton carrier) | Ucp3 | 2.943 | 2.792 |
| adiponectin, C1Q and collagen domain containin | Adipoq | 3.082 | 1.56 |
| diacylglycerol O-acyltransferase 2 | Dgat2 | 2.784 | 2.14 |
| solute carrier family 27 (fatty acid transporter), member 1 | Slc27a1 | 3.58 | 2.195 |
| lipase, hormone sensitive | Lipe | 3.032 | 1.746 |
| solute carrier family 25 (mitochondrial carnitine/acylcarnitine translocase), member 20 | Slc25a20 | 1.704 | 1.697 |

TABLE 4-continued

Targets common to exercise-PPARδ and AMPK-PPARδ gene signatures.

| DESCRIPTION | LOCUS | Tr + GW | AI + GW |
|---|---|---|---|
| CD36 antigen | Cd36 | 1.584 | 1.513 |
| phosphoenolpyruvate carboxykinase 1, cytosolic | Pck1 | 3.518 | 1.781 |
| fatty acid synthase | Fasn | 6.323 | 2.24 |
| fatty acid binding protein 4, adipocyte | Fabp4 | 2.189 | 1.81 |
| monoglyceride lipase | Mgll | 1.907 | 1.51 |
| acetyl-Coenzyme A acetyltransferase 2 | Acat2 | 1.625 | 1.563 |
| acetyl-Coenzyme A dehydrogenase, long-chain | Acadl | 2.549 | 1.992 |
| resistin | Retn | 4.114 | 1.756 |
| malonyl-CoA decarboxylase | Mlycd | 1.781 | 1.962 |
| transketolase | Tkt | 2.256 | 1.983 |
| ATP citrate lyase | Acly | 2.458 | 1.91 |
| HEAT SHOCK | | | |
| heat shock protein 90 kDa alpha (cytosolic), class A member 1 | Hsp90aa1 | 1.455 | 0.616 |
| DnaJ (Hsp40) homolog, subfamily B, member 1 | Dnajb1 | 3.59 | 0.604 |
| CYTOKINES | | | |
| interferon, alpha-inducible protein 27 | Ifi27 | 1.714 | 1.537 |
| OTHER | | | |
| sarcolipin | Sln | 0.363 | 4.576 |
| thyroid hormone responsive SPOT14 homolog (Rattus) | Thrsp | 2.685 | 1.766 |
| RIKEN cDNA 2310076L09 gene | 2310076L09Rik | 1.868 | 2.117 |
| myosin, heavy polypeptide 2, skeletal muscle, adult | Myh2 | 2.194 | 1.797 |
| surfeit gene 4 | Surf4 | 2.091 | 0.654 |
| acid phosphatase 5, tartrate resistant | Acp5 | 3.91 | 1.477 |
| serine (or cysteine) proteinase inhibitor, clade A, member 1a | Serpina1a | 0.396 | 3.891 |
| cysteine dioxygenase 1, cytosolic | Cdo1 | 3.266 | 1.678 |
| erythroid differentiation regulator 1 | | 0.619 | 1.805 |
| RIKEN cDNA 1810073N04 gene | 1810073N04Rik | 2.326 | 1.628 |
| superoxide dismutase 3, extracellular | Sod3 | 1.606 | 1.617 |
| complement factor D (adipsin) | Cfd | 2.828 | 1.5 |
| cytochrome P450, family 2, subfamily e, polypeptide 1 | Cyp2e1 | 2.941 | 1.743 |
| catalase | Cat | 1.728 | 1.902 |
| early growth response 1 | Egr1 | 2.577 | 0.65 |
| OXYGEN CARRIER | | | |
| hemoglobin, beta adult minor chain\|hemoglobin Y, beta-like embryonic chain | Hbb-b2\|Hbb-y | 1.626 | 1.503 |
| STEROID BIOGENESIS | | | |
| retinol binding protein 4, plasma | Rbp4 | 2.065 | 2.225 |
| SIGNAL TRANSDUCTION | | | |
| adreneyrgic receptor, beta 3 | Adrb3 | 3.83 | 1.56 |
| protein tyrosine phosphatase-like (proline instead of catalytic arginine), member b | Ptplb | 2.38 | 1.569 |
| dual specificity phosphatase 7 | Dusp7 | 1.661 | 1.672 |
| TRANSCRIPTION | | | |
| nuclear receptor subfamily 4, group A, member 2 | Nr4a2 | 1.776 | 0.437 |
| TRANSPORT | | | |
| solute carrier family 1 (neutral amino acid transporter), member 5 | Slc1a5 | 1.939 | 1.511 |
| two pore channel 1 | Tpcn1 | 2.842 | 1.487 |
| seminal vesicle secretion 5 | Svs5 | 0.095 | 2.243 |

Data is average of N=3 samples in each group (p<0.05).

Quantitative expression analysis of selective oxidative genes (eight of those listed in Table 4) was determined in quadriceps of mice treated with vehicle (V), GW 1516 (GW, 5 mg/kg/day), AICAR (AI, 250 mg/kg/day) and the combination of the two drugs (GW+AI) for 6 days using the methods described in Example 1. As shown in FIGS. 9A-H, several of these biomarkers including PDK4, SCD1, ATP citrate lyase, HSL, mFABP and LPL were induced in a synergistic fashion by GW1516 and AICAR in the quadriceps (FIGS. 9C-9H). Intriguingly, synergism was undetectable in UCP3 and mCPT I (FIGS. 9A and B). These genes were induced in quadriceps of untrained VP16-PPARδ mice, where AMPK is constitutively active (Table 5).

TABLE 5

Selective oxidative genes induced in muscle by combined PPARδ and AMPK activation as well as VP16-PPARδ over-expression

| Description | Locus | GW + AI | VP-PPARδ |
|---|---|---|---|
| ATP citrate lyase | Acly | 1.648 | 3.095 |
| carnitine palmitoyltransferase 1b, muscle | Cpt1b | 1.371 | 1.678 |
| fatty acid binding protein 3, muscle and heart | Fabp3 | 1.447 | 5.904 |
| fatty acid synthase | Fasn | 2.24 | 2.749 |
| lipoprotein lipase | Lpl | 1.113 | 1.72 |

TABLE 5-continued

Selective oxidative genes induced in muscle by combined PPARδ and AMPK activation as well as VP16-PPARδ over-expression

| Description | Locus | GW + AI | VP-PPARδ |
|---|---|---|---|
| lipase, hormone sensitive | Lipe | 1.746 | 2.203 |
| pyruvate dehydrogenase kinase, isoenzyme 4 | Pdk4 | 2.486 | 5.06 |
| stearoyl-Coenzyme A desaturase 1 | Scd1 | 1.78 | 7.353 |
| uncoupling protein 3 | Ucp3 | 2.792 | 4.107 |

Collectively, these results demonstrate that while interaction between AMPK and PPARδ may substantially contribute to re-programming of the skeletal muscle transcriptome during exercise, additional changes may involve cross-talk between other components of the exercise signaling network and PPARδ. In summary, PPARδ and exercise synergistically regulate running endurance. Although not bound by theory, kinase activation may influence PPARδ signaling during exercise in establishing an "endurance gene expression signature" that effectively enhances performance.

Example 7

AMPK increases transcription activation by PPARδ. The genetic synergism described in Example 6 indicates that AMPK directly regulates the transcriptional activity of PPARδ in skeletal muscles. To demonstrate this, an analysis of the effects of GW1516 and AICAR on gene expression in primary muscle cells isolated from wild type and PPARδ null mice was performed. Primary muscle cells were isolated from wild type and PPARδ null mice as previously described (Rando and Blau, J. Cell. Biol. 125(6): 1275-87, 1994). Skeletal muscle C2C12 cells were cultured in DMEM containing 20% serum and penicillin/streptomycin cocktail. For differentiation, cells at 80% confluence were switched to a differentiation medium (DMEM+2% serum) for 4 days to obtain differentiated myotubules. Cells were treated with vehicle, GW1516, AICAR, or GW1516+AICAR (GW: 0.1 µM; AICAR: 500 µM) for 24 hours. RNA expression of UCP3, PDK4, LPL, and HSL was determined using real time quantitative PCR as described in Example 1. As shown in FIGS. 10A-D, synergism is dependent on PPARδ and lost in the null cells. Similar synergistic regulation of gene expression by GW1516 and AICAR was also observed in differentiated C2C12 cells. These results show that AMPK activation may enhance ligand-dependent transcriptional effects of PPARδ in muscles. To more directly address this, reporter gene expression assays were utilized.

AD 293 cells were cultured in DMEM containing 10% serum and an antibiotic cocktail. Cells were transfected with one or more of CMX-Flag, CMX-Flag PPARδ, CMX-Tk-PPRE, or CMX-βGAL, or an hAMPK (α1 and α2 subunits, Origene) expression vector using Lipofectamine™ 2000 in accordance with the manufacturer's instructions. Anti-Flag antibody-conjugated beads were incubated overnight at 40C with lysates from transfected cells. Flag-tagged protein or protein complexes were immunoprecipitated by separating the beads from non-bound materials. The beads were washed in ice-cold lysis buffer followed by extraction in Laemmli buffer. For co-immunoprecipitation experiments SDS was excluded from the lysis buffer. Western blotting was performed with antibodies specific for the Flag tag or AMPK α subunit(s).

Figures 10A, 10B:
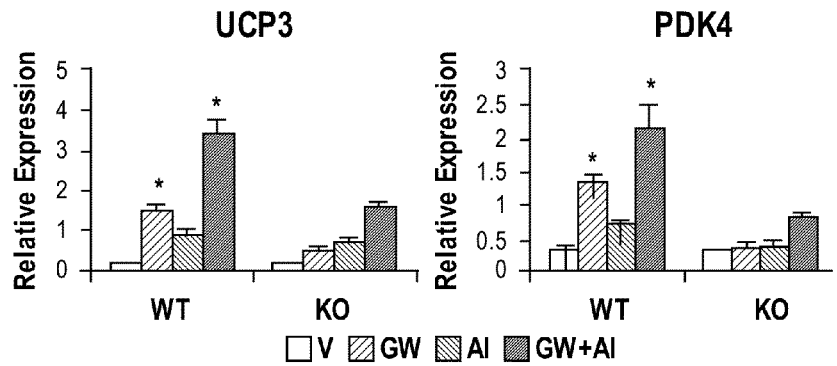
FIGS. 10A-L demonstrate the AMPK-PPARδ interaction. (A-D) show the expression of metabolic genes in wild type and PPARδ null (KO) primary muscle cells treated with V, GW, AI and GW+AI (bars from left to right) for 24 hours. In (E-F, J), AD293 cells were transfected with PPARδ+RXRα+ Tk-PPRE along with control vector, AMPK α1, cc2 and/or PGC 1α as indicated above. (E) Induction of basal PPARδ transcriptional activity by AMPK α1 or cc2. (F) Dose-dependent induction of PPARδ transcriptional activity is enhanced by AMPKα1 (closed circle) or AMPK cc2 (closed square) compared to control (open triangle). In (G-I, K), AD293 cells were transfected and processed as indicated. (G-H) Representative blot showing co-immunoprecipitation of transfected (G) or endogenous (H) AMPK with Flag-PPARδ. (I) Metabolic p32 labeling of PPARδ in AD293 cells transfected as described. (J) Synergistic regulation of basal (V) and ligand (GW) dependent PPARδ transcriptional activity by AMPK cc2 subunit and PGC 1α. (K) Co-immunoprecipitation of PPARδ but not AMPK α2 subunit with Flag-PGC1α. (L) Model depicting exercise-PPARδ interaction in re-programming muscle genome.
Figures 10C, 10D:
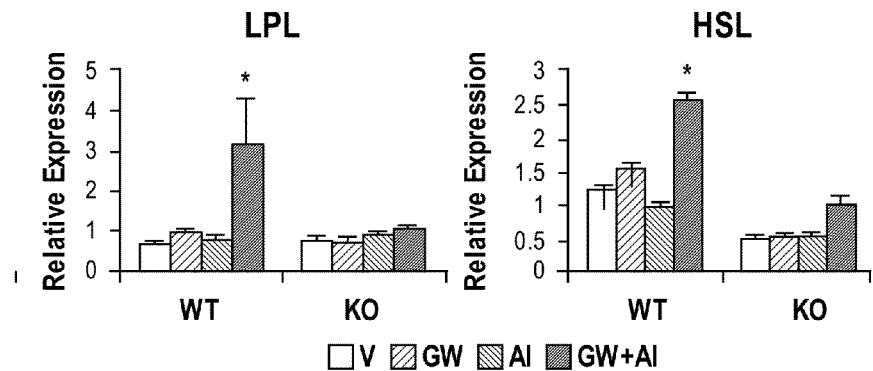
Figures 10E, 10F:
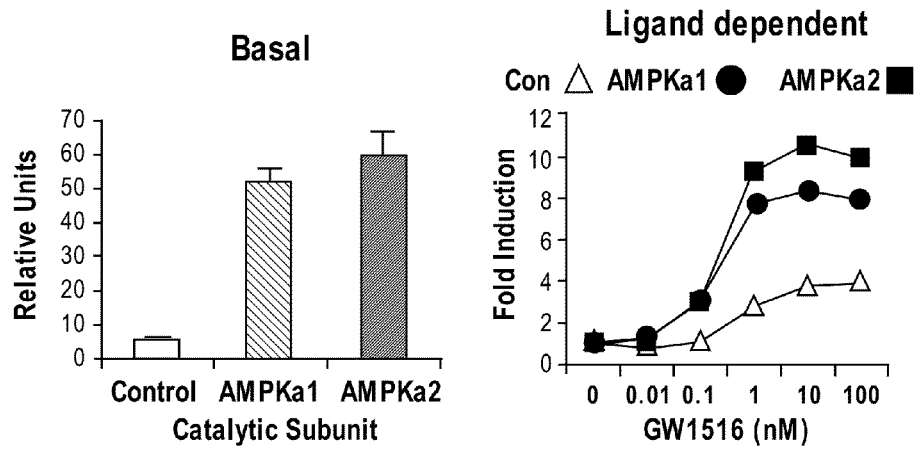
Figure 10G:
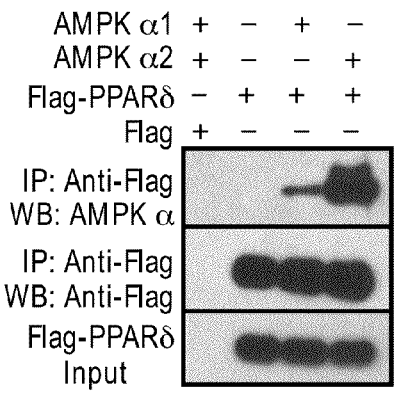
Figure 10H:
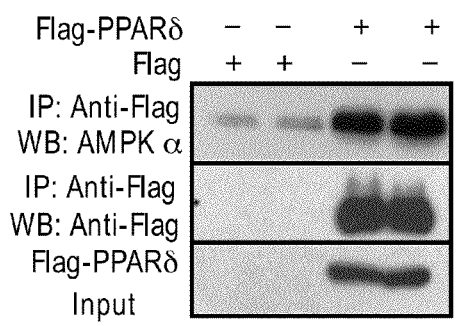

Co-transfection of either catalytic AMPK α1 or α2 subunits, but not control vector, with PPARδ increased the basal (FIG. 10E) and GW1516-dependent transcriptional activity (FIG. 10F) of PPARδ in inducing a PPRE-driven reporter gene in AD293 cells. AMPK over-expression or GW1516 treatment did not change reporter activity in transfections excluding the PPARδ expression vector negating the possibility of an effect via RXR. Additional results indicate that AMPK may modulate PPARδ transcriptional activity by directly interacting with the receptor. In AD293 cells co-transfected with Flag-PPARδ and with either catalytic AMPK α1 or α2 subunits, both of the subunits co-immunoprecipitated as a complex with Flag-PPARδ (FIG. 10G). Furthermore, Flag-PPARδ also co-immunoprecipitated endogenous AMPKα subunits from AD293 cells confirming a direct physical interaction between the nuclear receptor and the kinase (FIG. 10H). Despite physical interaction, AMPK failed to increase PPARδ phosphorylation.

While potential AMPK phosphorylation sites were found in PPARδ, none of these sites were phosphorylated by AMPK in in vitro kinase assays. This was further confirmed by measuring the p32 labeling of PPARδ in AD 293 cells in the presence or absence of AMPK. AD 293 cells were transfected with PPARδ and hAMPk (α1 or α2 subunit) expression vectors as described above. Forty-eight hours after transfection, the cells were washed three times with phosphate-free DMEM and incubated with 32P-orthophosphate in phosphate-free DMEM for 20 hours (100 µCi/5 ml). Cells were washed three times with ice-cold phosphate-free DMEM and lysed in ice-cold lysis buffer.

Figure 10I:
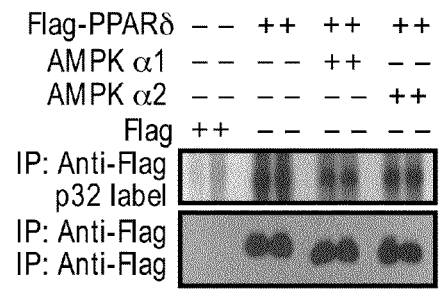
Figure 10J:
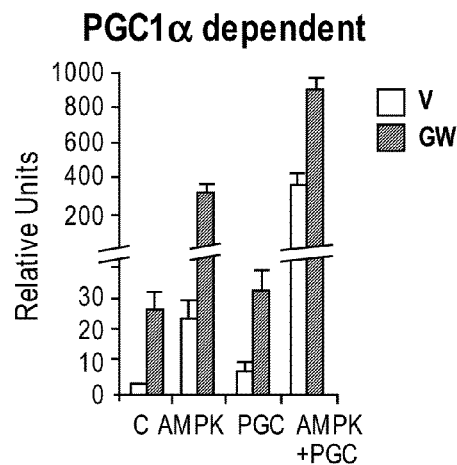
Figure 10K:
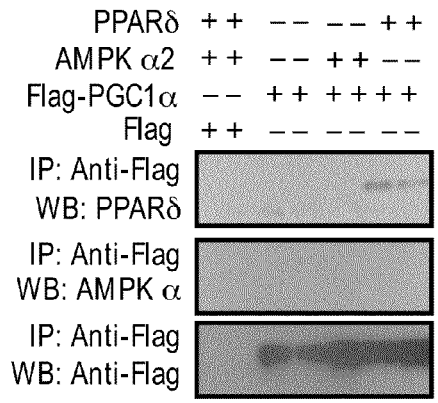

As shown in FIG. 10I, overall PPARδ phosphorylation is not increased by AMPK in vivo. However, co-transfection of AMPKcc2 and co-activator PGC1α (a known phosphorylation target of AMPK) co-operatively interact to further induce both the basal and ligand-dependent transcriptional activity of PPARδ (FIG. 10J). Strikingly, no significant physical interaction between Flag-PGC1α and AMPK (FIG. 10K) was detected, both of which independently interacted with PPARδ. Collectively, these observations indicate that AMPK may be present in a transcriptional complex with PPARδ where it can potentiate receptor activity via direct protein-protein interaction and/or by phosphorylating co-activators such as PGC1α.

These results indicate that AMPK directly interacts with PPARδ and dramatically increases basal and ligand-dependent transcription via the receptor. Despite physical interaction, AMPK does not phosphorylate PPARδ. AMPK and its substrate PGC1α synergistically increased PPARδ transcription, indicating indirect regulation of receptor by AMPK via co-regulator modification.

The conclusion that exercise-activated AMPK interacts with PPARδ in regulating gene expression in vivo is strengthened by the observation that treatment of animals with AICAR (AMPK activator) and GW1516 creates a gene signature in skeletal muscle that replicates up to 40% of the genetic effects of combined exercise and GW1516 treatment (see Table 4). Moreover, several candidate genes from this signature are synergistically induced by GW1516 and AICAR in wild type but not in PPARδ null primary muscle cells, demonstrating that the interactive effects of the two drugs are mediated through PPARδ. While 45% of the commonly regulated genes are linked to oxidative metabolism, additional common targets relevant to muscle performance include angiogenic, signal transduction and glucose sparing genes (Table 4). It is possible that the portion of the PPARδ-exercise signature that is independent of PPARδ-AMPK interaction (FIG. 8B) may depend on cross-talk between the receptor and other exercise signal transducers such as MAPK, calcineurin/NFAT and SIRT 1. These possibilities are summarized in FIG. 10L, where AMPK and additional components of the signaling network are proposed to interact with liganded PPARδ to generate a muscle endurance gene signature and enhanced endurance adaptation.

Figure 10L:
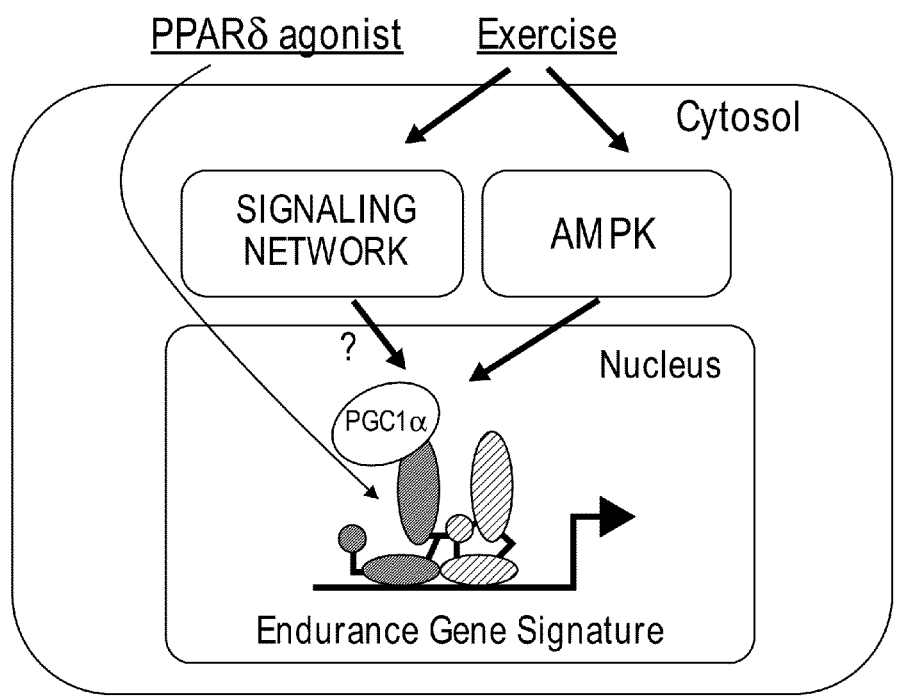

The data show that synthetic PPARδ activation alone induces a set of genomic changes that fail to alter the preset muscle architecture and endurance levels in adult mice. However, the combination of PPARδ activation with exercise brings about novel transcriptional changes, potentially via interaction with kinases such as AMPK (as depicted in FIG. 10L), re-setting the muscle transcriptome to a phenotype that dramatically enhances muscle performance.

Example 8

The data demonstrate that pharmacologic activation of PPARδ in adult mice can increase running endurance in conjunction with exercise signals. The central role for AMPK in this process is especially underscored by the observations that it is both robustly stimulated by exercise as well as constitutively active in muscles of VP16-PPARd transgenic mice that exhibit endurance without exercise. Further, AMPK can integrate multiple transcriptional programs by interacting not only with PPAR.delta. but also other transcriptional regulators of metabolism (e.g., PGClα, PPARα) (Hong et al., 2003; Leff, 2003; Bronner et al., 2004; Jaager et al., 2007). This raises the interesting question as to whether chemical activation of AMPK is sufficient to increase running endurance without exercise.

Figure 11:
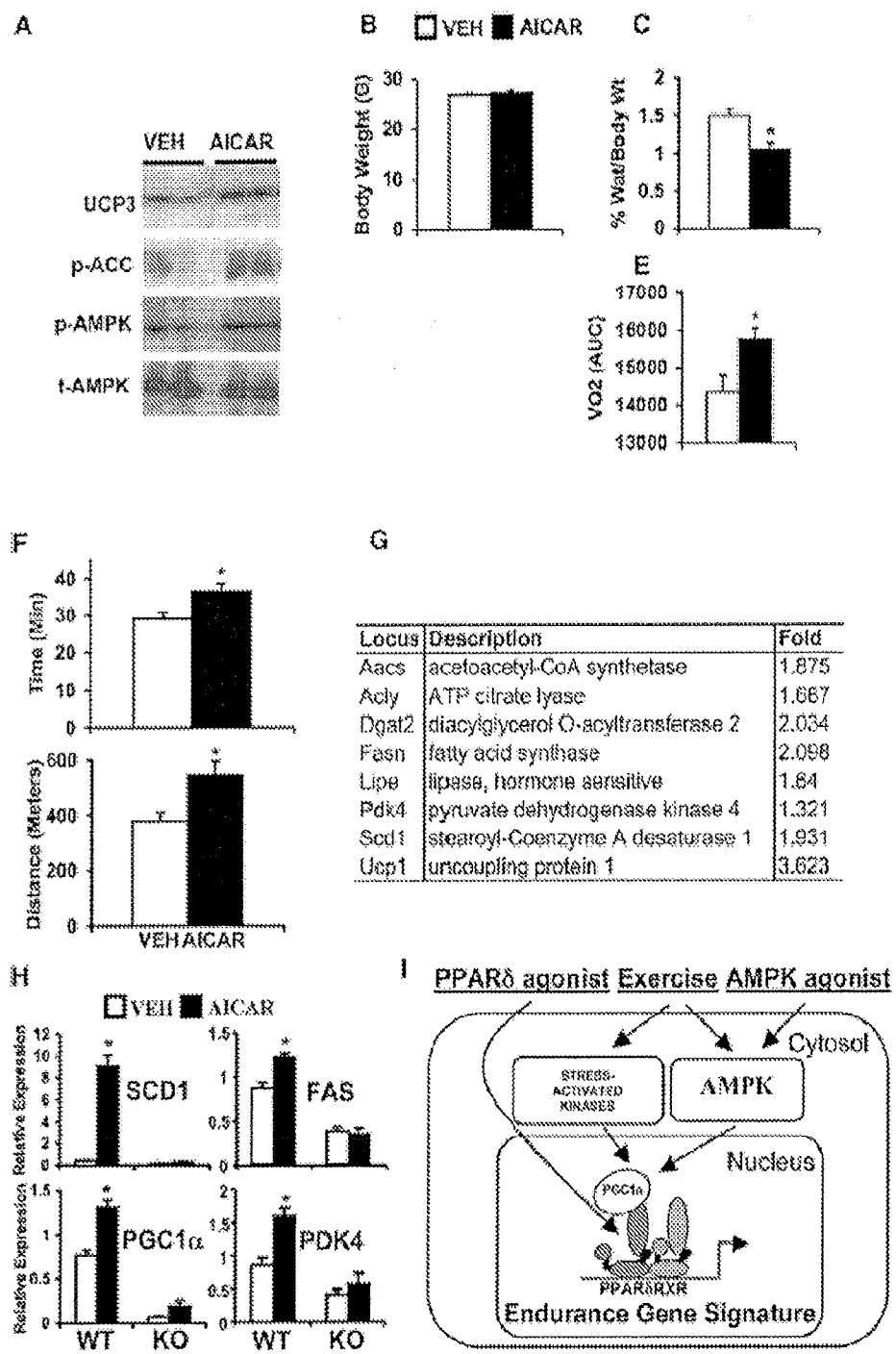
FIG. 11A-I shows that AICAR increases running endurance. (A-F) C57Bl/6J mice were treated with vehicle (open bars or thin lines) or AICAR (500 mg/kg/day, 4 weeks) (closed bars or thick lines). (A) Representative immunoblots showing levels of UCP3, phospho-acetyl CoA carboxylase (ACC), phospho-AMPK, and total-AMPK in quadriceps. (B) Average body weight. (C) Percent epididymal fat mass to body weight ratio. (D) Oxygen consumption rates (mg/kg/hr) measured over 12 hr period. (E) Data in (D) represented as AUC. (F) Running endurance measured as a function of time (upper panel) and distance (lower panel). (G) Representative oxidative genes induced by AICAR treatment (250 mg/kg/day, 6 days). (H) Expression of oxidative biomarkers (Scd1, Fasn, Ppargc1a, Pdk4) in wild-type and PPARd null primary myoblast treated with vehicle (open bars) or AICAR (closed bars) for 72 hr. (I) Model depicting the interaction between exercise and AMPK-PPARd in reprogramming muscle genome. Data in (B) and (C) (n=10), (D) and (E) (n=4), (F) (n=15-20), and (H) (n=9) are presented as mean±SEM, and * indicates statistical significance ($p<0.05$, unpaired student's t test).
Figures 11, 11D:
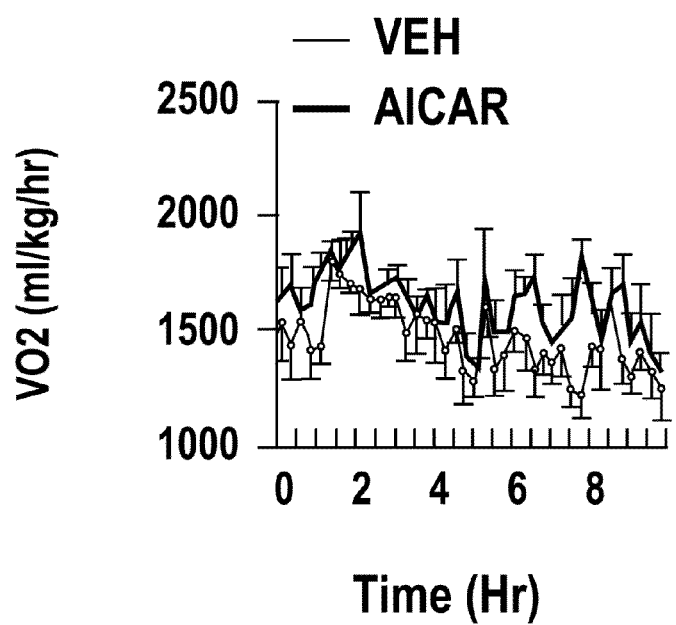

To test this idea C57B/6J mice were treated with AICAR (500 mg/kg/day) for 4 weeks. AICAR increased phosphorylation of AMPK a subunit and acetyl CoA carboxylase (ACC) and increased expression of UCP3 in quadriceps, confirming effective activation of AMPK signaling (FIG. 11A). Interestingly, 4 weeks of drug treatment decreased the ratio of epididymal fat mass to body weight and increased oxygen consumption without changing body weight (FIGS. 11B-11E), supporting the speculation that AICAR may positively regulate endurance. Indeed, in a treadmill endurance test, AICAR-treated mice ran longer (~23%) and further (~44%) than did vehicle-treated mice, revealing that increase in endurance can be achieved without exercise (FIG. 11F). Furthermore, global gene expression analysis of quadriceps revealed that AICAR treatment alone upregulated a set of 32 genes linked to oxidative metabolism (FIG. 11G and Table 6). Notably, 30 of these 32 genes were also upregulated in VP16-PPARδ transgenic mice, suggesting that stimulation of oxidative genes by AMPK may depend on PPARδ (Table 6).

TABLE 6

Oxidative genes induced by AMPK agonist AICAR as well as by transgenic over-expression of VP16-PPARδ in quadriceps of untrained mice. Data is average of N = 3 mice in each group (p < 0.5).

| Locus | Description | AICAR | VP-PPARd |
|---|---|---|---|
| Aacs | acetoacetyl-CoA synthetase | 1.875 | 2.771 |
| Acly | ATP citrate lyase | 1.687 | 2.429 |
| Adipoq | adiponectin | 2.043 | 2.122 |
| Ak2 | adenylate kinase 2 | 1.486 | 1.173 |
| Apoe | apolipoprotein E | 1.403 | 1.959 |
| Cd36 | CD36 antigen | 1.386 | 3.66 |
| Ces3 | carboxylesterase 3 | 1.516 | 1.869 |
| Cidea | cell death-inducing DNA fragmentation factor, alpha subunit-like effector A | 5.021 | 2.356 |
| Dgat2 | diacylglycerol O-acyltransferase 2 | 2.034 | 2.147 |
| Elovl6 | ELOVL family member 6 | 2.134 | 4.43 |
| Fabp4 | fatty acid binding protein 4, adipocyte | 1.709 | 1.23 |
| Fasn | fatty acid synthase | 2.098 | 2.749 |

TABLE 6-continued

Oxidative genes induced by AMPK agonist AICAR as well as by transgenic over-expression of VP16-PPARδ in quadriceps of untrained mice. Data is average of N = 3 mice in each group (p < 0.5).

| Locus | Description | AICAR | VP-PPARd |
|---|---|---|---|
| Lep | leptin | 2.047 | 3.579 |
| Lipe | lipase, hormone sensitive | 1.64 | 2.203 |
| Lpl | lipoprotein lipase | 1.386 | 1.285 |
| Mgll | monoglyceride lipase | 1.503 | 2.816 |
| Mgst1 | microsomal glutathione S-transferase 1 | 1.602 | 1.905 |
| Nrip1 | nuclear receptor interacting protein 1 | 1.474 | 1.887 |
| Pck1 | phosphoenolpyruvate carboxykinase 1 | 2.68 | 2.169 |
| Pcx | pyruvate carboxylase | 1.393 | — |
| Pdk4 | pyruvate dehydrogenase kinase, isoenzyme 4 | 1.321 | 5.06 |
| Pparg | peroxisome proliferator activated receptor gamma | 3.027 | 2.334 |
| Retn | resistin | 1.891 | 1.641 |
| Scd1 | stearoyl-Coenzyme A desaturase 1 | 1.931 | 7.353 |
| Sdhd | succinate dehydrogenase complex, subunit D | 1.529 | 1.349 |
| Sfxn1 | sideroflexin 1 | 1.713 | 1.494 |
| Slc25a5 | | 1.372 | 1.348 |
| Sult1a1 | sulfotransferase family 1A | 2.021 | 1.996 |
| Tspo | translocator protein | 1.441 | 2.133 |
| Ucp1 | uncoupling protein 1 | 3.623 | 0.695 |
| Ucp3 | uncoupling protein 3 | 1.258 | 4.107 |

To test this possibility, wild-type and PPARδ null primary muscle cells were used. Treatment of wild-type primary cells with AICAR (for 72 hr) increased expression of key oxidative biomarker genes (Scd1, fasn [FAS], Ppargc 1a, Pdk4) (FIG. 11H). In contrast, AICAR failed to increase the expression of the above genes in PPARδ null cells, demonstrating the requirement of the receptor for transcriptional effects of AMPK on oxidative genes.

The data show that the AMP-mimetic AICAR can increase endurance in sedentary mice by genetically reprogramming muscle metabolism in a PPARδ-dependent manner. The data also demonstrate that PPARδ agonist in combination with exercise synergistically induces fatigue resistant type I fiber specification and mitochondrial biogenesis, ultimately enhancing physical performance. These changes correlate with an unexpected but interesting establishment of a muscle endurance gene signature that is unique to the drug-exercise paradigm. Such a signature is an outcome of molecular crosstalk and perhaps a physical association between exercise-activated AMPK and PPARδ. These findings identify a novel pharmacologic strategy to reprogram muscle endurance by targeting AMPK-PPARδ signaling axis with orally active ligands.

The AMPK activator AICAR increased oxygen consumption and endurance in untrained adult mice in part by stimulating PPARδ-dependent oxidative genes. Despite a demonstrated role for PPARδ in endurance, 4 week treatment with a potent and selective agonist failed to alter either fiber type composition or endurance, revealing that direct and pharmacologic activation of PPARδ is insufficient to enhance running performance. In contrast, transgenic overexpression of activated PPARδ at birth preprograms the nascent myofibers to transdifferentiate into slow-twitch fibers, thus imparting a high basal endurance capacity to adult transgenic mice. Apparently, once fiber type specification is complete in adults, the potential plasticity of muscle to synthetic activation of a single transcriptional pathway is constrained.

Along these lines, the unexpected yet successful reprogramming of endurance in untrained adults with synthetic AMP-mimetic might be linked to the ability of AMPK to simultaneously target multiple transcriptional programs governed by its substrates such as PGC1a, PPARα and PPARδ, triggering a genetic effect akin to exercise (Hong et al., 2003; Leff, 2003; Bronner et al., 2004; Jager et al., 2007).

Interestingly, the recalcitrance of adult skeletal muscle endurance to manipulation by PPARδ agonist alone is relieved by combining drug treatment with exercise. Indeed, this strategy generates an endurance gene signature that is unique from either paradigm alone, reflecting a crosstalk between exercise and PPARδ signaling. Although exercise activates a cascade of signaling events, AMPK is likely central to this genetic adaptation for several reasons. First, AMPK is a metabolic sensor that detects low ATP levels (such as occur during exercise) and in turn increases oxidative metabolism (Mu et al., 2001; Reznick and Shulman, 2006). Second, long-term effects of AMPK are in part mediated via regulation of gene expression (Reznick and Shulman, 2006). Third, exercise induces activation and nuclear import of AMPK, where it can potentially interact with transcription factors.

And finally, transgenic mice defective for AMPK activation exhibit reduced voluntary exercise (Mu et al., 2001; Thomson et al., 2007), making it an attractive exercise cue that modulates receptor signaling.

The notion that exercise-activated AMPK interacts with PPARδ in regulating gene expression is supported by the demonstration that AMPK associates with PPARδ and dramatically increases basal and ligand-dependent transcription via the receptor. Despite physical interaction, AMPK does not induce PPARδ phosphorylation in metabolic labeling studies.

Interestingly, AMPK and its previously reported substrate PGC1a synergistically increased PPARδ transcription, suggesting indirect regulation of receptor function by AMPK via coregulator modification. Nevertheless, it could be a possible regulation of PPARδ by AMPK via direct protein-protein interaction.

Indeed, regulation of other transcription factors by AMPK via similar mechanisms has been previously demonstrated (Hong et al., 2003; Leff, 2003; Bronner et al., 2004). A physiological validation of AMPK-PPARδ interaction comes from the observation that GW1516 and AICAR (AMPK activator) synergistically induce several endurance-related genes in wild-type but not in PPARδ null primary muscle cells. More importantly, treatment of animals with AICAR and GW1516 creates a gene signature in skeletal muscle that replicates up to 40% of the genetic effects of combined exercise and GW1516 treatment. Notably, the shared genes between the two profiles are linked to oxidative metabolism, angiogenesis, and glucose sparing, pathways that are directly relevant to muscle performance.

Although not all genes regulated by either exercise or exercise-PPARδ interaction are AMPK dependent, two key findings assign a critical role for the kinase in promoting endurance compared to other known exercise signals (Bassel-Duby and Olson, 2006; Goodyear et al., 1996; Lagouge et al., 2006). First, AMPK is constitutively active in VP16-PPARδ transgenic muscles that exhibit endurance without exercise. Second, AMPK activation by AICAR was sufficient to increase running endurance without additional exercise signals. Strikingly, the majority of the oxidative genes (30 out of 32) upregulated by AICAR are active in super-endurance VP16-PPARδ mice and perhaps are the core set of genes required to improve muscle performance.

Interestingly, AICAR failed to induce oxidative gene expression in PPARδ null muscle cells, indicting the requirement of PPARδ, at least for regulation of oxidative metabolism by AMPK. Collectively, these findings demonstrate a molecular partnership between AMPK and PPARδ in reprogramming skeletal muscle transcriptome and endurance (FIG. 11I) that can be readily exploited by orally active AMPK drugs to replace exercise.

In humans, endurance exercise leads to physiological adaptations in the cardiopulmonary, endocrine, and neuromuscular systems (Jones and Carter, 2000; Lucia et al., 2001). Although the investigation focused on skeletal muscle, extramuscular effects of PPARd, AMPK, and exercise may also contribute to increased endurance. Although potentiation of extramuscular adaptations by PPARd and AMPK agonists remains to be studied, drug treatment can reduce epididymal fat mass, possibly conferring additional systemic benefits. It is noteworthy that PPARδ is important for normal cardiac contractility, as well as for the endocrine function of adipose tissue (Wang et al., 2003; Cheng et al., 2004). Similarly, the activation of AMPK by metformin is thought to mediate its ability to lower blood glucose levels (Shaw et al., 2005). In addition to increasing performance in athletes, exercise has beneficial effects in a wide range of pathophysiological conditions, such as respiratory disorders, cardiovascular abnormalities, type 2 diabetes, and cancer risk. The disclosure demonstrates that synthetic PPARδ activation and exercise—and, more importantly, AMPK activation alone—provide a robust transcriptional cue that reprograms the skeletal muscle genome and dramatically enhances endurance. The disclosure provides a strategy for reorganizing the preset genetic imprint of muscle (as well as other tissues) with exercise mimetic drugs has therapeutic potential in treating certain muscle diseases such as wasting and frailty as well as obesity where exercise is known to be beneficial.

Example 9

Enhancing exercise effect in a subject. This example describes methods that can be used to increase or enhance an exercise in a healthy mammalian subject. Although specific conditions are described, one skilled in the art will appreciate that minor changes can be made to such conditions.

Healthy adult human subjects perform aerobic exercise (e.g., running) for at least 30 minutes (e.g., 30-90 minutes) for at least 3-4 days per week (e.g., 3-7 days per week) for at least 2 weeks (e.g., at least 4-12 weeks). The exercise is performed at 40%-50% maximal heart rate, 500-60% maximal heart rate, 60%-70% maximal heart rate, or 75%-80% maximal heart rate, where maximum heart rate for a human subject is calculated as: 220 bps−(age of the subject).

During or after performing aerobic exercise as described above, the subjects are orally administered GW1516 [(2-methyl-4(((4-methyl-2-(4-trifluoromethylphenyl)-1,3-thiazol-5-yl)methyl)sulfanyl)phenoxy)acetic acid] at a dose of 1 to 20 mg per day, such as 2.5 or 10 mg per day. Subjects can continue to perform aerobic exercise while receiving GW1516. The subject can receive GW1516 for a period of at least 2 weeks, such as at least 4 weeks.

The exercise effect achieved in the treated subjects (e.g., running endurance) can be compared to such an effect in untreated subjects. Exercise effect can be measured using methods known in the art, such as measuring aerobic or running endurance (for example measuring distance run until exhaustion or amount of time to run a particular distance). In some instances, the exercise effect of interest is increased in treated subjects by at least 5%, such as at least 10% as compared to untreated subjects.

Example 10

Identifying performance enhancing substances in an exercise-trained subject. This example describes methods that can be used to identify performance-enhancing substances in an exercised-trained subject. A biological sample obtained from a healthy adult human is analyzed to determine if the subject is taking a PES (e.g., GW1516) by analyzing expression of one or more of the molecules (nucleic acids or proteins) listed in Table 2 or Table 4. Suitable biological samples include samples containing genomic DNA or RNA (including mRNA) or proteins obtained from cells of a subject, such as those present in peripheral blood, urine, saliva, tissue biopsy, or buccal swab. For example, a biological sample of the subject can be assayed for a change in expression (such as an increase or decrease) of any combination of at least four molecules (nucleic acids or proteins) listed in Table 2 or 4, such as any combination of at least 10, at least 20, at least 30, or at least 40 of those listed in Table 2 or 4, for example all of those listed in Table 2 or 4.

Methods of isolating nucleic acid molecules from a biological sample are routine, for example using PCR to amplify the molecules from the sample, or by using a commercially available kit to isolate mRNA or cDNA. However, nucleic acids need not be isolated prior to analysis. Nucleic acids can be contacted with an oligonucleotide probe that will hybridize under stringent conditions with one or more nucleic acid molecule listed in Table 2 or 4. The nucleic acids which hybridize with the probe are then detected and quantified. The sequence of the oligonucleotide probe can bind specifically to a nucleic acid molecule represented by the sequences listed in Table 2 or 4.

Increased or decreased expression of the molecules listed in Table 2 or 4 can be detected by measuring the cellular levels of mRNA. mRNA can be measured using techniques well known in the art, including for instance Northern analysis, RT-PCR and mRNA in situ hybridization. Details of mRNA analysis procedures can be found, for instance, in provided examples and in Sambrook et al. (ed.), Molecular Cloning: A Laboratory Manual, 2nd ed., vol. 1-3, Cold Spring Harbor Laboratory Press, Cold Spring Harbor, N.Y., 1989.

Oligonucleotides specific to sequences listed in Table 2 or 4 can be chemically synthesized using commercially available machines. These oligonucleotides can then be labeled, for example with radioactive isotopes (such as 32P) or with non-radioactive labels such as biotin (Ward and Langer et al., Proc. Natl. Acad. Sci. USA 78:6633-57, 1981) or a fluorophore, and hybridized to individual DNA samples immobilized on membranes or other solid supports by dot-blot or transfer from gels after electrophoresis. These specific sequences are visualized, for example by methods such as autoradiography or fluorometric (Landegren et al., Science 242:229 '-37', 1989) or colorimetric reactions (Gebeyehu et al., Nucleic Acids Res. 15:4513-34, 1987).

Analyzing Proteins in the biological sample can also be analyzed. In some examples, proteins are isolated using routine methods prior to analysis.

In one example, surface-enhanced laser desorption-ionization time-of-flight (SELDI-TOF) mass spectrometry is used to detect changes in differential protein expression, for example by using the ProteinChip™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586). SELDI is a solid phase method for desorption in which the analyte is presented to the energy stream on a surface that enhances analyte capture or desorption. Therefore, in a particular example, the chromatographic surface includes antibodies that recognize proteins listed in Table 2 or 4. Antigens present in the sample can recognize the antibodies on the chromatographic surface. The unbound proteins and mass spectrometric interfering compounds are washed away and the proteins that are retained on the chromato graphic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

In another examples, the availability of antibodies specific to the molecules listed in Table 2 or 4 facilitates the detection and quantification of proteins by one of a number of immunoassay methods that are well known in the art, such as those presented in Harlow and Lane (Antibodies, A Laboratory Manual, CSHL, New York, 1988). Methods of constructing such antibodies are known in the art. Any standard immunoassay format (such as ELISA, Western blot, or RIA assay) can be used to measure protein levels. Immunohistochemical techniques can also be utilized for protein detection and quantification. For example, a tissue sample can be obtained from a subject, and a section stained for the presence of the desired protein using the appropriate specific binding agents and any standard detection system (such as one that includes a secondary antibody conjugated to horseradish peroxidase). General guidance regarding such techniques can be found in Bancroft and Stevens (Theory and Practice of Histological Techniques, Churchill Livingstone, 1982) and Ausubel et al. (Current Protocols in Molecular Biology, John Wiley & Sons, New York, 1998).

For the purposes of detecting or even quantifying protein or nucleic acid expression, expression in the test sample can be compared to levels found in cells from a subject who has not taken a PES. Alternatively, the pattern of expression identified in the test subject can be compared to that shown in Table 2 or 4.

For example, if the test sample shows a pattern of expression similar to that in Table 2 or 4 (e.g., the genes shown as upregulated and downregulated in Table 2 or 4 are observed in the subject to be upregulated and downregulated, respectively), this indicates that the subject is taking a PES, such as a PPARδ agonist (e.g., GW1516). In contrast, If the pattern of expression identified in the test subject is different to that shown in Table 2 or 4 (e.g., the genes shown as upregulated and downregulated in Table 2 or 4 are observed in the subject to be not differentially expressed or show a different pattern of regulation), this indicates that the subject is not taking a PES, such as a PPARδ agonist (e.g., GW1516).

A significant increase in the non-bolded proteins listed in Table 2 in the cells of a test subject compared to the amount of the same protein found in normal human cells is usually at least 2-fold, at least 3-fold, at least 4-fold or greater difference. Substantial overexpression of the non-bolded proteins listed in Table 2 in the subject's sample can be indicative of the subject taking a PES. Similarly, a significant decrease in the bolded proteins listed in Table 2 in the cells of a test subject compared to the amount of the same protein found in normal human cells is usually at least 2-fold, at least 3-fold, at least 4-fold or greater difference.

Substantial underexpression of the bolded proteins listed in Table 2 in the subject's sample can be indicative of the subject taking a PES.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

We claim:

1. A method for improving muscle endurance in a subject independent of exercise, the method comprising administering to the subject an effective amount of an AMP kinase (AMPK) agonist, wherein the AMPK agonist is 5-amino-4-imidazolecarboxamide riboside (AICAR), and an effective amount of a PPARδ agonist, wherein the PPARδ agonist is (2-methyl-4(((4-methyl-2-(4-trifluoromethylphenyl)-1,3-thiazol-5-yl)methyl)sulfonyl)phenoxy) acetic acid (GW1516), thereby improving muscle endurance in a subject independent of exercise.

2. The use method of claim 1, wherein the subject has a muscle wasting disease or disorder.

3. The method of claim 1, wherein the subject is a racing mammal.

4. The method of claim 3, wherein the racing mammal is a horse, a dog, or a human.

5. The method of claim 1, wherein the subject is an adult.

6. The method of claim 1, wherein the subject is an exercise-trained subject.

7. The method of claim 1, wherein the PPARδ agonist is administered on the same day(s) on which the AMPK agonist is administered.

8. The method of claim 1, further comprising having the subject perform aerobic exercise.

9. The method of claim 1, wherein improved endurance comprises improved running distance or improved running time or a combination thereof 10. The method of claim 1, wherein fatty acid oxidation is increased in at least one skeletal muscle of the subject.

11. The method of claim 1, wherein body fat is reduced.

12. The method of claim 11, wherein the body fat is white adipose tissue.

13. The method of claim 1, wherein the individual has a neuromuscular disease.

14. The method of claim 1, wherein the individual does not participate in substantial exercise prior to experiencing improved muscular endurance following the administering step.

* * * * *